United States Patent
Griffin et al.

(10) Patent No.: US 12,370,193 B2
(45) Date of Patent: Jul. 29, 2025

(54) METHOD OF INHIBITING TREM-1

(71) Applicant: UNIVERSITY OF FLORIDA RESEARCH FOUNDATION, INCORPORATED, Gainesville, FL (US)

(72) Inventors: Patrick R. Griffin, Jupiter, FL (US); Mi Ra Chang, Jupiter, FL (US); Jason Fisherman, Brookline, MA (US); Peter Suzman, Newton, MA (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 812 days.

(21) Appl. No.: 17/491,834

(22) Filed: Oct. 1, 2021

(65) Prior Publication Data
US 2022/0117965 A1 Apr. 21, 2022

Related U.S. Application Data

(63) Continuation of application No. PCT/US2020/026526, filed on Apr. 3, 2020.

(60) Provisional application No. 62/828,805, filed on Apr. 3, 2019, provisional application No. 62/828,978, filed on Apr. 3, 2019.

(51) Int. Cl.
| | | |
|---|---|---|
| C07D 401/06 | (2006.01) | |
| A61K 31/496 | (2006.01) | |
| A61K 31/506 | (2006.01) | |
| A61P 3/00 | (2006.01) | |
| A61P 3/04 | (2006.01) | |
| A61P 29/00 | (2006.01) | |

(52) U.S. Cl.
CPC ............ *A61K 31/506* (2013.01); *A61P 3/04* (2018.01); *A61P 29/00* (2018.01)

(58) Field of Classification Search
CPC ....... C07D 401/06; A61K 31/496; A61P 3/00; A61P 29/00
See application file for complete search history.

(56) References Cited

U.S. PATENT DOCUMENTS

| 9,586,928 B2 | 3/2017 | Kamenecka et al. |
| 2008/0247955 A1 | 10/2008 | Kuai et al. |
| 2018/0085348 A1 | 3/2018 | Chen et al. |

FOREIGN PATENT DOCUMENTS

| WO | WO 2012/158784 A2 | 11/2012 |
| WO | 2017007712 A1 | 1/2017 |

OTHER PUBLICATIONS

"TREM-1 Pathway Activation in COVID-19 (CoviTrem1)," ClinicalTrials.gov Identifier: NCT04544891 (2020).
Amrun, S. et al., "TREM-1 Activation is a Potential Key Regulator in Driving Severe Pathogenesis of Enterovirus A71 Infection", Scientific Reports, 10:3810 | https://doi.org/10.1038/s41598-020-60761-5 (2020).
Brocklebank, V. et al., "Thrombotic Microangiopathy and the Kidney", Clin. J. Am. Soc. Nephrol., vol. 13, Feb. 2018, 300-317.
Campbell, G. et al., "TREM-1 Protects HIV-1-Infected Macrophages from Apoptosis Through Maintenance of Mitochondrial Function", Amer. Soc. Microbio., vol. 10, Iss. 6: 1-17 (2019). Downloaded from https://journals.asm.org/journal/mbio on Jan. 2, 2022.
Chang, M. et al., "Pharmacological Repression of RORγ is Therapeutic in the Collagen-Induced Arthritis Experimental Model", Arthritis Rheumatol., vol. 66, No. 3: 579-588 (2014).
Chang, M. R. et al., "Unique Polypharmacology Nuclear Receptor Modulator Blocks Inflammatory Signaling Pathways", ACS Chemical Biology, vol. 14: 1051-1062 (2019).
Channappanavar, R. et al., "Pathogenic Human Coronavirus Infections: Causes and Consequences of Cytokine Storm and Immunopathology", Seminars in ImmunoPathology, vol. 39 :529-539 (2017).
Cioni, B. et al., "Androgen Receptor Signalling in Macrophages Promotes TREM-1-Mediated Prostate Cancer Cell Line Migration and Invasion", Nature Communications, 11:4498 (2020), p. 1-17. https://doi.org/10.1038/s41467-020-18313-y.
De Stoppelaar, S. F. "Platelets: Versatile Effector Cells in Pneumonia and Sepsis", 's-Hertogenbosch: Uitgeverij BOXPress, UVA-DARE (Digital Academic Repository) University of Amsterdam, 183-192 (2015).
Edel, Y. et al., "Elevated Plasma Level of Soluble Triggering Receptor Expressed on Myeloid Cells-1 is Associated with Inflammation Activity and is a Potential Biomarker of Thrombosis in Primary Antiphospholipid Syndrome", Arthritis Research & Therapy, vol. 21, No. 10 (2019).
Gao, S. et al., "The Characteristics and Pivotal Roles of Triggering Receptor Expressed on Myeloid Cells-1 in Autoimmune Diseases", Autoimmunity Reviews, vol. 18, 2019, 25-35.
Hoang, T. et al., "Global Gene Expression profiling Identifies new Therapeutic Targets in Acute Kawasaki Disease", Genome Medicine, vol. 6, No. 102: 1-13 (2014).
Hotez, P. et al., "COVID-19 Vaccine Design: The Janus Face of Immune Enhancement", Nature Reviews | Immunology, https://doi.org/10.1038/ S41577-020-0323-4, 2020.
Joffre, J. et al., "Genetic and Pharmacological Inhibition of TREM-1 Limits the Development of Experimental Atherosclerosis", J. Am. Coll. Cardiology, vol. 68, No. 25, 2776-2793 (2016).
Jolly, L. et al., "Triggering Receptor Expressed on Myeloid Cells-1: A New Player in Platelet Aggregation", Thrombosis and Haemostasis, 117: 1772-1781 (2017).

(Continued)

*Primary Examiner* — Brenda L Coleman
(74) *Attorney, Agent, or Firm* — Wolf, Greenfield & Sacks, P.C.

(57) ABSTRACT

Disclosed herein are methods and uses of the polypharmacological modulator SR1903 and related compounds for inhibiting triggering receptor expressed on myeloid cells-1 (TREM-1) and treating diseases and conditions that are related to or mediated by TREM-1, such as inflammatory diseases, autoimmune diseases, metabolic disorders, and castration resistant prostate cancer (CRPC).

8 Claims, 25 Drawing Sheets

Specification includes a Sequence Listing.

(56) References Cited

OTHER PUBLICATIONS

Liu, T. et al., "Blocking Triggering Receptor Expressed on Myeloid Cells-1 Attenuates Lipopolysaccharide-Induced Acute Lung Injury via Inhibiting NLRP3 Inflammasome Activation", Scientific Reports, 6:39473 | DOI: 10.1038/srep39473, (2016), 1-12.

Marik, P. et al., "SIRS, qSOFA and New Sepsis Definition", J. Thorac. Dis., vol. 9, No. 4: 943-945 (2017).

Merrill, S. et al., "Complement-Driven Anemia: More Than Just Paroxysmal Nocturnal Hemoglobinuria", Hematology, 371-376 (2018).

Mohamadzadeh, M. et al., "Activation of Triggering Receptor Expressed on Myeloid Cells-1 on Human Neutrophils by Marburg and Ebola Viruses", J. Virol., vol. 80, No. 14, 2006, 7235-7244.

Moore, J. et al., "Cytokine Release Syndrome in Severe COVID-19", Science, 10.1126/science.abb8925 (2020), Apr. 17, 2020, 1-4.

Page, M. et al., "A Champion of Host Defense: A Generic Large-Scale Cause for Platelet Dysfunction and Depletion in Infection", Seminars in Thrombosis & Hemostasis, vol. 46, No. 3, (2020) 302-319.

Rivas, M. et al., "Kawasaki Disease: Pathophysiology and Insights from Mouse Models", Nature Reviews | Rheumatology, vol. 16, Jul. 2020, 391-405.

Roe, K. et al., "Triggering Receptor Expressed on Myeloid Cells-1 (TREM-1): A New Player in Antiviral Immunity?", Frontiers in Microbio., vol. 5, Art. 627, Nov. 26, 2014, 1-11.

Schultz, D. et al., "Carrageenan Containing Over-the-Counter Nasal and Oral Sprays Inhibit SARS-CoV-2 Infection of Epithelial Cultures", Downloaded from journals.physiology.org/journal/ajplung (073.119.016.060) on Mar. 5, 2021.

Solaimanzadeh, I. "Acetazolamide, Nifedipine and Phosphodiesterase Inhibitors: Rationale for Their Utilization as Adjunctive Countermeasures in the Treatment of Coronavirus Disease 2019 (COVID-19)", Cureus 12(3): e7343, DOI 10.7759/cureus.7343, Mar. 20, 2020, 1-6.

Tammaro, A. et al., "TREM-1 and its Potential Ligands in Non-Infectious Diseases: From Biology to Clinical Perspectives", Pharmac. & Therapeutics, vol. 177, 2017, 81-95.

Tang, X. et al., "Comparison of Hospitalized Patients with ARDS Caused by COVID-19 and H1N1", Chest, vol. 158, No. 1, 2020, 195-205.

Yeh, A. et al., "Hematopoietic Stem Cell Transplant-Associated Thrombotic Microangiopathy: Current Paradigm and Novel Therapies", Bone Marrow Transplantation, 2017, 1-9.

Zuo, Y. et al., "Neutrophil Extracellular Traps in COVID-19", JCI Insight, https://doi.org/10.1172/jci.insight.138999, 2020.

Extended European Search Report for EP App. No. 20784271.7 mailed Apr. 25, 2023.

Guntermann et al., Retinoic-acid-orphan-receptor-C inhibition suppresses Th17 cells and induces thymic aberrations. JCI Insight. Mar. 9, 2017;2(5):e91127. doi: 10.1172/jci.insight.91127. 16 pages.

Helix 2 LXRa LBD± SR1903

Red: Apo receptor
Blue: Liganded

Perturbation view
LXR +/- SR1903;
+/- GW3965

| Ingenuity Canonical Pathways | z-score | Molecules |
| --- | --- | --- |
| Dendritic Cell Maturation | -3.578 | IL1A,IL10,FCGR2A,IL36A,HLA-DQA1,CD83,IL6,HLA-DQB1,FCGR2B,TLR9,IL33,TLR4,COL5A3,CD80,IL1RN,IL12B,HLA-DRA,IL1B,CD86,CSF2,IL23A,HLA-DRB5 |
| TREM1 Signaling | -2.887 | TLR4,TREM1,IL10,TLR8,IL1B,CD86,CD83,IL6,FCGR2B,CSF2,TLR9,ITGAX |
| Acute Phase Response Signaling | -2.828 | IL33,IL1A,IL1RN,Saa3,CF8,IL36A,IL1B,CP,IL6 |
| LPS/IL-1 Mediated Inhibition of RXR Function | -2.449 | IL1A,IL36A,ABCG1,IL33,HS6ST1,TLR4,SCARB1,IL1RN,RARA,CHST3,PPARGC1B,CHST11,FABP4,IL1B,CHST10,RXRA |
| Role of IL-17F in Allergic Inflammatory Airway Diseases | -2 | MMP13,IL1B,IL6,CSF2 |
| IL-6 Signaling | -1.89 | IL33,IL1A,IL1RN,IL36A,IL1B,IL6,TLR9 |
| Role of NFAT in Regulation of the Immune Response | -1.732 | FCGR2A,HLA-DQA1,HLA-DQB1,TLR9,FCGR2B,CD80,SYK,HLA-DRA,ITPR3,CD86,NFATC2,MEF2C,GNB1L,HLA-DRB5 |
| Colorectal Cancer Metastasis Signaling | -1.732 | MMP3,SMAD3,TLR8,VEGFB,MMP13,IL6,TLR9,CCND1,TLR4,MSH2,PTGER2,PTGS2,GNB1L,MMP12 |
| Toll-like Receptor Signaling | -1.667 | IL33,TLR4,IL1A,IL1RN,IL12B,TLR8,IL36A,TNFAIP3,IL1B,IRAK3,TLR9 |
| p38 MAPK Signaling | -1.667 | IL33,IL1A,DDIT3,IL1RN,DUSP1,IL36A,IL1B,MEF2C,IRAK3 |
| HMGB1 Signaling | -1.633 | TLR4,IL1A,IL12B,IL1B,IL6,CSF2,TLR9 |
| Fcγ Receptor-mediated Phagocytosis in Macrophages and Monocytes | -1.342 | ACTA2,FCGR2A,SYK,PRKCH,CSF2 |
| NF-κB Signaling | -1.265 | IL33,TLR4,IL1A,IL1RN,TLR8,IL36A,TNFAIP3,IL1B,IRAK3,TLR9 |
| iCOS-iCOSL Signaling in T Helper Cells | -1.134 | CD80,ITPR3,HLA-DRA,HLA-DQA1,NFATC2,HLA-DQB1,TLR9,HLA-DRB5 |
| PKCθ Signaling in T Lymphocytes | -1 | MAP3K9,CD80,HLA-DRA,HLA-DQA1,NFATC2,CD86,HLA-DQB1,TLR9,HLA-DRB5 |
| Phospholipase C Signaling | -1 | HDAC9,FCGR2A,SYK,ITPR3,NFATC2,ARHGEF17,PRKCH,MEF2C,ARHGEF3,GNB1L,FCGR2B,HDAC5 |
| Gαi Signaling | -1 | CAV1,FPR2,GNB1L,FPR1,XCR1 |
| Wnt/β-catenin Signaling | -1 | GJA1,RARA,CD44,CCND1 |
| Cell Cycle: G1/S Checkpoint Regulation | -0.707 | HDAC9,CCNE1,RBL2,CCND2,SMAD3,CCND1,E2F2,HDAC5 |
| Leukocyte Extravasation Signaling | -0.707 | MMP3,CLDN12,ACTA2,TIMP1,CD44,MMP13,PRKCH,MMP12,TLR9 |
| cAMP-mediated signaling | -0.707 | CAMK1,DUSP1,FPR2,PDE4B,PTGER2,FPR1,ADRB2,XCR1 |
| Integrin Signaling | -0.447 | ACTA2,CAV1,TNK2,TLR9,ITGAX |
| Role of Pattern Recognition Receptors in Recognition of Bacteria and Viruses | -0.378 | IL1A,IL10,TLR8,CCL5,IL6,TLR9,TLR4,CLEC7A,IL12B,SYK,IL1B,PRKCH,CSF2 |
| Calcium-induced T Lymphocyte Apoptosis | -0.378 | ITPR3,HLA-DRA,HLA-DQA1,NFATC2,PRKCH,HLA-DQB1,HLA-DRB5 |
| CD28 Signaling in T Helper Cells | 0 | CD80,SYK,ITPR3,HLA-DRA,HLA-DQA1,NFATC2,CD86,HLA-DQB1,TLR9,HLA-DRB5 |
| GM-CSF Signaling | 0 | CSF2RB,CISH,TLR9,CSF2,BCL2A1,CCND1 |
| Cell Cycle Regulation by BTG Family Proteins | 0 | CCNE1,BTG1,CCND1,E2F2 |
| Role of BRCA1 in DNA Damage Response | 0 | RBL2,GADD45A,MSH2,E2F2 |
| Tec Kinase Signaling | 0 | TLR4,ACTA2,TNFSF10,PRKCH,GNB1L,TLR9 |
| IL-8 Signaling | 0.333 | CCND2,VEGFB,PRKCH,PTGS2,IRAK3,GNB1L,TLR9,CCND1,LIMK1,ITGAX |
| AMPK Signaling | 0.378 | PFKFB3,FASN,ACACA,MLYCD,GNB1L,TLR9,CCND1,ADRA1A,ADRB2 |
| Death Receptor Signaling | 0.447 | ACTA2,CRADD,TNFSF10,TNFSF15,LIMK1 |
| RhoGDI Signaling | 0.447 | ACTA2,CD44,ARHGEF17,ARHGEF3,GNB1L,LIMK1 |
| ILK Signaling | 0.447 | ACTA2,FLNC,VEGFB,PTGS2,TLR9,CCND1 |
| Role of NFAT in Cardiac Hypertrophy | 0.707 | HDAC9,CAMK1,ITPR3,PRKCH,MEF2C,IL6,GNB1L,TLR9,HDAC5 |
| B Cell Receptor Signaling | 0.816 | MAP3K9,FCGR2A,SYK,NFATC2,MEF2C,TLR9,BCL2A1,FCGR2B |
| Endothelin-1 Signaling | 0.816 | EDN1,ITPR3,PRKCH,ECE1,PTGS2,PTGER2,TLR9 |
| Signaling by Rho Family GTPases | 0.816 | MAP3K9,ACTA2,ARHGEF17,ARHGEF3,GNB1L,TLR9,LIMK1 |
| Cyclins and Cell Cycle Regulation | 1 | HDAC9,CCNE1,CCND2,CCND1,E2F2,HDAC5 |
| Pancreatic Adenocarcinoma Signaling | 1 | CCNE1,SMAD3,VEGFB,PTGS2,TLR9,CCND1,E2F2 |
| α-Adrenergic Signaling | 1 | ITPR3,PRKCH,PYGL,GNB1L,ADRA1A |
| Rac Signaling | 1 | CYFIP2,CD44,TLR9,LIMK1 |
| Protein Kinase A Signaling | 1 | PPP1R3D,DUSP1,FLNC,SMAD3,ITPR3,NFATC2,PYGL,PRKCH,PTGS2,PDE4B,GNB1L |
| HGF Signaling | 1.342 | MAP3K9,PRKCH,IL6,PTGS2,TLR9,CCND1 |
| mTOR Signaling | 1.342 | DDIT4,PRR5,VEGFB,PRKCH,GNB1L,TLR9 |
| Thrombin Signaling | 1.342 | CAMK1,ITPR3,PRKCH,ARHGEF3,GNB1L,TLR9 |
| Glioma Signaling | 1.633 | RBL2,CAMK1,PRKCH,TLR9,CCND1,E2F2 |
| PPARα/RXRα Activation | 1.633 | FASN,SMAD3,IL1B,MEF2C,IL6,RXRA |
| Production of Nitric Oxide and Reactive Oxygen Species in Macrophages | 1.633 | TLR4,MAP3K9,PPP1R3D,PRKCH,PCYOX1,TLR9 |
| Cardiac Hypertrophy Signaling | 1.633 | MAP3K9,MEF2C,IL6,GNB1L,TLR9,ADRA1A,ADRB2 |
| fMLP Signaling in Neutrophils | 2 | ITPR3,FPR2,NFATC2,PRKCH,GNB1L,FPR1 |
| NRF2-mediated Oxidative Stress Response | 2 | AKR7A2,ACTA2,SCARB1,MAF,PRKCH,TLR9,DNAJB9,CBR1 |
| Calcium Signaling | 2 | HDAC9,CAMK1,ACTA2,ITPR3,NFATC2,MEF2C,HDAC5 |
| Neuropathic Pain Signaling In Dorsal Horn Neurons | 2 | CAMK1,ITPR3,PRKCH,TLR9 |
| Nitric Oxide Signaling in the Cardiovascular System | 2.236 | ITPR3,CAV1,SLC7A1,VEGFB,PRKCH,TLR9 |
| eNOS Signaling | 2.236 | Hspa1b,ITPR3,CAV1,SLC7A1,VEGFB,PRKCH,TLR9 |
| Gαq Signaling | 2.236 | ITPR3,NFATC2,PRKCH,GNB1L,TLR9,ADRA1A |
| PPAR Signaling | 2.646 | IL33,IL1A,IL1RN,IL36A,IL1B,PTGS2,RXRA |
| LXR/RXR Activation | 2.714 | SCD,IL1A,IL36A,ABCG1,PCYOX1,IL6,IL33,TLR4,IL1RN,FASN,IL1B,ACACA,PTGS2,RXRA |

FIG. 10

SEQUENCE LISTING

```
<160> NUMBER OF SEQ ID NOS: 25

<210> SEQ ID NO 1
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 1

Ala Ser Lys His Lys Gln Leu Ser Glu Leu Leu Arg Ser Gly Ser Ser
1               5                   10                  15

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
gtaacccgtt gaaccccatt                                                 20

<210> SEQ ID NO 3
<211> LENGTH: 21
<212> TYPE: DNA
<213> ORGANISM: Artificial Sequence
```

```
<220> FEATURE:
<223> OTHER INFORMATION: Synthetic oligonucleotide

<400> SEQUENCE: 3
ccatccaatc ggtagtagcc g                                          21

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ttcatcgtcc tgggcatctt                                            20

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 5
cggattttgt atctgaggac gaa                                        23

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
gctggcattc gtgatggagt cgt                                        23

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
aggccaccag tgatgatgta actct                                      25

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
acccagaaga ctgtggatgg                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
acacattggg ggtaggaaca                                            20
```

```
<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tgagactccg ttctggcctc                                              20

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
ctcttcatgc ttggtacccg at                                           22

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
ccatcagggc tggaaaggtt                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
gggcaggcag taatcccttt                                              20

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
ctctgtttta tgctgttatg ggtga                                        25

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
ggtcaacagg agaatctccc ag                                           22

<210> SEQ ID NO 16
<211> LENGTH: 26
<212> TYPE: DNA
<213> ORGANISM: Artificial Sequence
<220> FEATURE:
<223> OTHER INFORMATION: Synthetic oligonucleotide
```

<400> SEQUENCE: 16
acctccactg ccagctgtgt gctgtc                                        26

<210> SEQ ID NO 17
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 17
tcatttctgc acttctgcat gtagactgtc cc                                 32

<210> SEQ ID NO 18
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 18
tagcctgtaa aagatttctg caaacc                                        26

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 19
tgacttgggc attgcaga                                                 18

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 20
ctgacgacgg agtttggg                                                 18

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
gctccaaaag cgagtaccag c                                             21

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
agtagaatcc gctctcctgc ag                                            22

<210> SEQ ID NO 23

```
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 23
cggaattcga gcttgaagga tgaggaaggc                                    30

<210> SEQ ID NO 24
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 24
aatccagagt ctgtcacttg aaggtcagtc                                    30

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
ccggagaccc cttagatcga                                               20
```

METHOD OF INHIBITING TREM-1

RELATED APPLICATIONS

This application is a continuation of International Application No. PCT/US2020/026526, which designated the United States and was filed on Apr. 3, 2020, published in English, which claims the benefit of U.S. Provisional Application No. 62/828,805 filed on Apr. 3, 2019 and U.S. Provisional Application No. 62/828,978 filed on Apr. 3, 2019. The entire contents of each of the above applications are incorporated by reference herein.

GOVERNMENT SUPPORT

This invention was made with government support under grants Nos. MH084512 and DK080261 awarded by the National Institutes of Health. The U.S. government has certain rights in the invention.

BACKGROUND OF THE INVENTION

Nuclear receptors (NRs) comprise a superfamily of ligand-dependent transcription factors, including receptors for thyroid hormones, steroid hormones, retinoids, fatty acids, sterols and oxysterols. These receptors display a conserved domain structure with a variable amino-terminal AB domain, a highly conserved two zinc finger DNA-binding domain (C domain), a hinge (domain D) and a carboxy-terminal ligand-binding domain (LBD; E domain) containing activation function 2 (AF2) critical for co-regulator interactions. The LBDs of the nuclear receptors are multifunctional and are predominately a-helical in nature, characteristic of all NRs. Small pharmacological compounds that bind within the ligand binding pocket (LBP) of the LBD have the potential to directly alter the conformational dynamics of the receptor[1]. These ligand-induced alterations in conformational dynamics modulate the receptors' ability to interact with coregulatory proteins (i.e., coactivators such as SRC2 or corepressors such as NCoR or SMRT). These coregulatory proteins remodel chromatin to facilitate engagement of basal transcription machinery, thus altering the transcriptional output of specific NR target genes. NRs bind to specific DNA sequences (receptor binding sequences) found throughout the genome including clusters in promoter and enhancer regions of genes under their control. Receptor binding sequences (RBSs) that are functional in vivo are referred to as response elements (REs)[2].

The three members of the ROR (RAR-related orphan receptor) NR1F subfamily of NRs, RORα, RORβ, and RORγ, have significant sequence similarities but display distinct patterns of expression and each ROR gene generates several isoforms, differing only in their amino termini as a consequence of alternative promoter usage and exon splicing. RORα is expressed in the liver, skeletal muscle, skin, lungs, adipose tissue, kidney, thymus and brain[30, 46]. RORβ has a more restricted pattern of expression and is limited to the central nervous system and bone[30, 47]. RORγ is most highly expressed in the thymus, but significant expression is also found in the liver, skeletal muscle, adipose tissue and kidney[48]. The RORγ2 isoform, referred to as RORγt, is exclusively expressed in a subset of immune cells and has garnered much attention due to its role in differentiation of TH17 cells[3]. Regardless, RORγ1 and RORγt have identical ligand-binding domains suggesting that most if not all RORγ targeting ligands modulate both isoforms.

The ROR NR1F subfamily has been the target of intense drug discovery efforts given that the RORγ2 isoform, referred to as RORγ, is exclusively expressed in a subset of immune cells garnering much attention due to its role in differentiation of $T_H17$ cells[3]. As previously shown in Chang et al. (2014)[4], administration of the small molecule selective RORγ inverse agonist SR2211 was efficient at pharmacological repression of the receptors activity affording a robust therapeutic effect in CIA mice. SR2211 is described in U.S. Pat. No. 9,586,928 and has the chemical structure shown below:

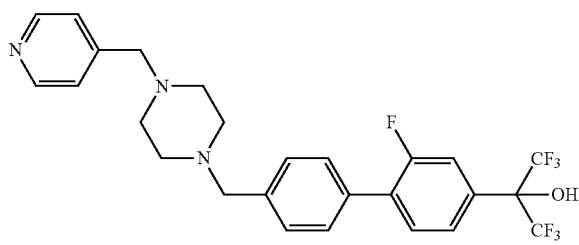 [SMILES: OC(c1ccc(-c2ccc(CN3CCN(Cc4ccncc4)CC3)cc2)c(F)c1)(C(F)(F)F)C(F)(F)F]

In the Chang et al. study, repression of $T_H17$ cell differentiation by SR2211 also resulted in induction of IFNγ production in draining lymph nodes of treated animals, an observation that is consistent with the relationship of $T_H17$ cells to $T_H1$ cells. It was also demonstrated that treatment of cells in culture or tissues ex vivo with SR2211 inhibited $T_H17$ cell differentiation, reduced IL-17 and IL-23R expression, reduced expression of inflammatory cytokines in activated macrophages, and stimulated systemic activation of $T_H1$ cells as inferred by the induction of IFNγ. That study along with the demonstration that RORγ small molecule repressors can block $T_H17$ cell development and autoimmunity led to an explosion of effort in this area with at least one compound currently in clinical trials[5-6].

There remains a need in the art for additional inhibitors of RORγ and methods of use thereof.

SUMMARY OF THE INVENTION

The present invention is based on the discovery that SR1903 (chemical structure shown in FIG. 1), which is a close chemical analog of SR2211, had nearly identical activity on RORγ but has a broadened nuclear receptor (NR) activity profile with modest agonism of LXR and mild repressive or inverse agonism of PPARγ; and further that SR1903 blocks Triggering Receptor Expressed on Myeloid cells 1 (TREM-1).

The invention is therefore directed to a method of inhibiting TREM-1 in a subject in need thereof comprising administering to said subject an effective amount of a compound having the formula (I):

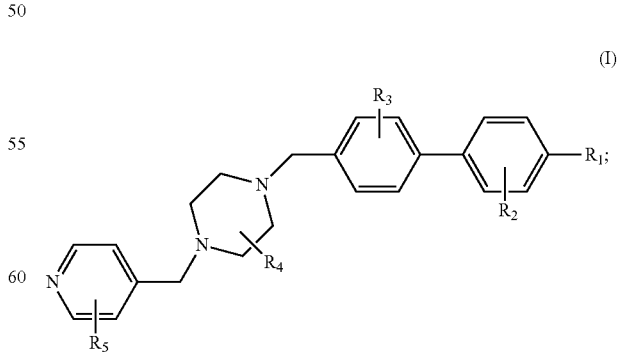

wherein:
R₁ is C1-C4 alkyl substituted with OR or C1-C4 fluoroalkyl substituted with OR;

$R_2$, $R_4$, and $R_5$ are each independently selected from the group consisting of hydrogen, halo, C1-C4 alkyl, and C1-C4 alkoxy;

$R_3$ is C1-C4 alkyl; and

R is hydrogen or C1-C4 alkyl; or a pharmaceutically acceptable salt thereof.

In certain aspects, the compound is SR1903. In specific embodiments, the subject or patient is suffering from TREM-1 mediated inflammation or chronic inflammation. In certain aspects, administration of the compound of Formula (I) or SR1903 preserves the thymus or protects against loss of thymocytes, for example, as compared to the administration of RORγ selective inverse agonist such as SR2211 and/or as compared to that before or without administration of the compound.

In an additional embodiment, the present disclosure provides a method for treating a subject suffering from a disease or condition that is related to triggering receptor expressed on myeloid cells-1 (TREM-1), comprising administering to the patient a therapeutically effective amount of the compound SR1903 or a pharmaceutically acceptable salt thereof:

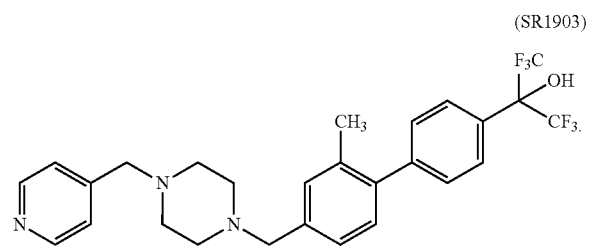

(SR1903)

In yet additional aspects, the invention is directed to a method of inhibiting TREM-1 in a subject in need thereof comprising administering to said subject an effective amount of a compound that is a RORγ inverse agonist and is also an inverse agonist of PPARγ and/or an agonist of LXR. In certain aspects, the compound is a RORγ inverse agonist, an inverse agonist of PPARγ and an agonist of LXR.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1A shows the chemical structures of SR1903, SR2211 and GW3965. FIG. 1B shows the results of Gal4-RORγ, Gal4-RORγ, Gal4-RORγ, Gal4-LXRα, and Gal4-PPARγ co-transfection assays in HEK293 cells comparing GW3965 to SR1903. FIG. 1C shows the results of Lanthascreen competition binding assay with DMSO only, rosiglitazone and SR1903 in 12-point dose-response. FIG. 1D is a graph showing PPARγ target genes (aP2 and CD36) expression in OP9 cells with and without MDI (IBMX, dexamethasone, insulin) treatment. OP9 cells were stimulated with MDI cocktail for 4 days or 1 uM Rosiglitazone, or MDI plus 5 uM SR1903. FIG. 1E shows in silico docking of SR1903 to PPARγ, RORγ and LXRβ LBD shows putative protein-ligand interactions driving observed polypharmacology. SR1903 is represented as orange sticks while PPARγ, RORγ, and LXRβ are depicted as blue ribbons respectively. Specific residues driving the interaction labelled and shown as sticks as well. SR1903 was docked to PPARγ in the antagonist conformation (PDB 6C5Q), RORγ in the antagonist conformation, and LXRβ in the agonist conformation.

FIG. 2A shows a heat map of log 2 fold change in expression of TREM-1 signaling pathway genes in LPS-stimulated RAW264.7 cells treated with SR1903 versus to LPS-stimulation alone. FIG. 2B are graphs showing TREM-1 gene expression by q-PCR. FIG. 2C is a graph showing TREM1 promoter regulation by LXRβ or PPARγ or RORγ±SR1903. FIG. 2D shows TREM-1 surface expression after 26 hr stimulation with LPS or 50 hr stimulation. All experiments were performed with 3 biological replicates and the median value of TREM-1 fluorescence was represented by the graph on the bottom.

FIG. 3A shows a heat map of log 2 fold change in LXR activation in LPS-stimulated RAW264.7 cells treated with SR1903 vs to LPS-stimulation alone. FIG. 3B are graphs showing inflammatory cytokines, non-inflammatory fatty acid synthesis genes, cholesterol efflux in LPS-stimulated RAW264.7 cells treated with SR1903. FIGS. 3C and 3D show log 2 fold change of SENP3 expression in RAW264.7 cells mRNAseq and q-PCR.

FIG. 4A is a graph showing that treatment with SR1903 (20 mg/kg) suppresses the clinical severity of collagen induced arthritis. Clinical score was monitored every day after boosting during 18 days. Vehicle (square, n=10), GW3965 (clear circle, n=10), T0901317 (clear square, n=10), or SR1903 (circle, n=10) were i.p injected. The dosage of all compounds was identical in each group. FIG. 4B shows the results of glucose tolerance test (GTT) after i.p. challenge with 1 g/kg of glucose. FIG. 4C shows serum concentrations of glucose, cholesterol, HDL (high density lipoprotein), LDL (low density lipoprotein), TAG (triacylglycerol), and FFA (free fatty acid). FIG. 4D shows circulatory insulin and leptin levels after overnight fasting and feeding condition. FIG. 4E shows the average difference in weight of SR1903- or vehicle-treated DIO mouse at study's end. lost body weight and NMR. FIG. 4F is a graph showing leptin sensitivity, as measured by the food intake after leptin administration on day 10, day 11, and day 12. FIG. 4G is a graph showing Socs3 gene expression in hypothalamus of vehicle or 1903 treated DIO mice or lean mice (n=3). Values are the mean±S.E.M. *, p<0.001; , p<0.01; *, p<0.05 statistically significant difference between vehicle and SR1903.

FIG. 5A shows mRNA expression of PPARγ and RORγ in adipogenesis of OP9 cells for 4 days with/without SR1903. FIG. 5B shows the formation of lipid droplet of OP9 cells. FIG. 5C shows induction of RORγ expression by Rosiglitazone and suppression of PPARγ expression by SR1903 during OP9 adipogenesis.

FIG. 6A are graphs showing HDX kinetics of representative peptic peptides derived from the PPARγ-LBD and LXRα-LBD in complex with SR1903. The top left of FIG. 6A shows differential HDX analysis of SR1903 showed evidence of direct interaction with decreased deuterium exchange within Helix 3 region of PPARγ LBD, a region of the receptor critical for ligand engagement. The top right of FIG. 6A shows SR1903 interaction with LXRα LBD resulted in an increase in deuterium exchange in H2 region of LXRα LBD suggesting that SR1903 displaces endogenous ligand in the purified protein. FIG. 6B shows differential HDX perturbation view for PPARγ LBD in the absence and presence of SR1903 or rosiglitazone control, and LXRα in the absence and presence of SR1903 or GW3965. Percentages of deuterium differences are color-coded according to the smooth color gradient key displayed at the bottom.

FIG. 9: Analysis of CIA mice administered either vehicle, GW3965, T0901317, or SR1903 (20 mg/kg) for 14 days (normal chow diet CIA mice).

FIG. 10: Canonical Pathway Analysis of RNA-sequencing data.

DETAILED DESCRIPTION OF THE INVENTION

Figure 1A:
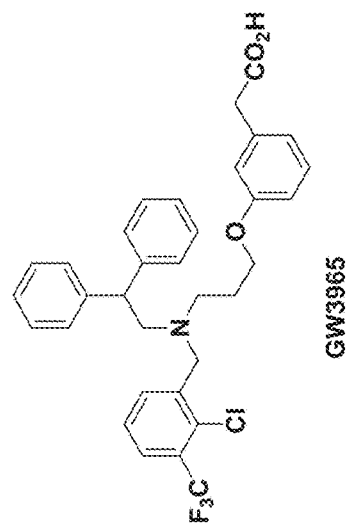
FIGS. 1A to 1E: Pan modulator with poly-pharmacology.
Figure 1A:
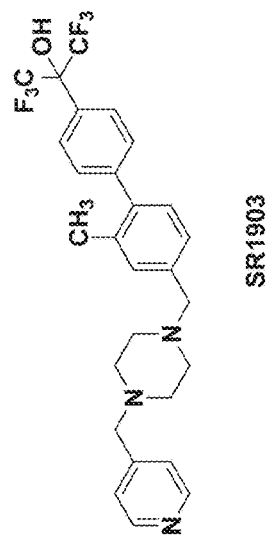
Figure 1A:
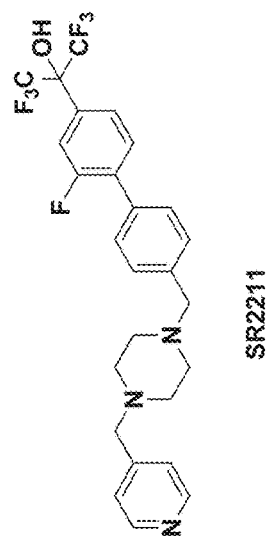

A description of preferred embodiments of the invention follows.

As used herein, the words "a" and "an" are meant to include one or more unless otherwise specified. For example, the term "a cell" encompasses both a single cell and a combination of two or more cells.

"Treating" or "treatment" as used herein covers the treatment of the disease or condition of interest in a mammal, preferably a human, having the disease or condition of interest, and includes, for example: preventing or delaying the onset of the disease or condition from occurring in a mammal, in particular, when such mammal is predisposed to the condition but has not yet been diagnosed as having it; inhibiting the disease or condition, i.e., arresting its development; relieving the disease or condition, i.e., causing regression of the disease or condition; and/or stabilizing the disease or condition. Treatment includes ameliorating or lessening the severity of symptoms of the disease or condition, and/or inhibition of further progression or worsening of those symptoms. The terms "treat", "treating" and "treatment" can also refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

An "effective amount" or a "therapeutically effective amount" of a compound described herein refers to an amount of the compound that is sufficient to achieve a specific effect or result, and/or treats the disease or condition and/or the symptoms therefore, for example, alleviating, in whole or in part, symptoms associated with the disorder or condition, or halts or slows further progression or worsening of those symptoms, or prevents or provides prophylaxis for the disorder or condition. In certain aspects, an effective amount is an amount sufficient to inhibit TREM-1 and/or inhibit TREM-1 gene expression. An effective amount can also be an amount that is sufficient to inhibit RORγ and/or PPARγ, and/or agonize an LXR. The term "effective amount" can also refer to an amount of a compound as described herein or other active ingredient sufficient to provide a therapeutic or prophylactic benefit in the treatment or prevention of a disease or to delay or minimize symptoms associated with a disease. Further, a therapeutically effective amount or an effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or is synergistic with another therapeutic agent. A therapeutically effective amount or an effective amount also is the minimum amount necessary to modulate or to inhibit TREM-1.

A "subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In certain preferred aspects, the subject is a human subject. A human subject can also be referred to as a "patient." In one embodiment, a patient is a human, such as a human infant, child, adolescent or adult. In the present disclosure, the terms "patient" and "subject" are used interchangeably.

In this description, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4- diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methyl sulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

As discussed above, Chang et al. showed that SR2211 treatment resulted in repression of $T_H17$ cell differentiation, induction of IFNγ, reduction of IL-17 and IL-23R expression, and reduced expression of inflammatory cytokines in activated macrophages. Lead optimization of SR2211 led to several interesting compounds including SR1903, a close chemical analog with nearly identical activity on RORγ. However, SR1903 was found to have a broadened NR activity profile with modest agonism of LXR and mild repressive or inverse agonism of PPARγ. Interestingly, SR1903 was found to potently block expression of Triggering Receptor Expressed on Myeloid cells 1 (TREM-1). TREM-1 is an orphan immunoreceptor expressed on macrophages and neutrophils and is a potent amplifier of pro-inflammatory innate immune responses although its endogenous ligand has yet to be identified[7].

Although it has been previously reported that TREM-1 expression is upregulated by PPARγ, there are no reports of pharmacologically targeting PPARγ to repress TREM-1[8-9]. Compounds that modulate the activity of LXR and PPARγ have been shown to have immunomodulatory activity. Agonists of LXR regulate macrophage inflammatory pathways and reduce inflammation in atherosclerotic plaques[10-11]. Modulators of PPARγ suppress pro-inflammatory cytokine production and drive M1 to M2 polarization of macrophages.[12] While agonists of PPARγ drive adipogenesis, antagonists of PPARγ have been shown to retain both anti-inflammatory activity and insulin sensitization properties of agonists without promoting fat accumulation[13]. The ability of SR1903 to downregulate TREM-1 may be due to its action on these receptors.

Nuclear receptors (NRs) function as ligand-modulated transcription factors controlling gene expression programs involved in numerous biological processes. The activity of NRs can be increased or decreased by administration of exogenous natural or synthetic ligands making them attractive drug targets for treatment of a wide range of diseases[1]. However, pleiotropic effects have limited the clinical utility of several approved NR modulators and ended clinical development of many more. This fact has spurred interest in developing functional selective NR modulators (also referred to as dissociated modulators), where the goal is to design ligands that modulate (activate or repress) a specific sub-set of disease-related genes. RORγ inverse agonists are currently under clinical development for treatment of various autoimmune diseases[38]. LXR agonists have been in clinical development for treatment of dyslipidemia and inflammatory diseases[39]. While PPARγ agonists and partial agonists have been approved and have been in clinical development for metabolic disease, inverse agonists of this receptor conceptually hold promise for a wide range of diseases including osteoporosis and cancer[14]. As such, we investigated the polypharmacological modulator SR1903 which functions as a potent RORγ inverse agonist with modest agonist activity on LXR and mild repression (inverse agonism) of PPARγ in a range of biophysical and cellular models.

Results presented herein demonstrate the anti-inflammatory and anti-diabetic properties of SR1903 in the collagen induced arthritis (CIA) and diet-induced obesity (DIO) mouse models, respectively. As expected, SR1903 afforded similar efficacy to that observed for SR2211 in the CIA model in terms of improvement in clinical scores[1]. However, unlike that observed in SR2211 treated mice[40], intrathymic cell number was enriched in SR1903 treated mice and secondary lymphoid organs such as lymph node and spleen had similar cell number to that of the vehicle-only control mice. Treatment of DIO mice with SR1903 resulted in reduction in fat mass resulting in reduced body weight and improvements in both insulin and leptin sensitivity. While food intake was reduced in the context of DIO, the compound had no impact on food consumption and body weight when administered to lean mice, and SR1903 had a null effect in a conditioned taste aversion behavioral paradigm.

Interestingly, some of the effects of this polypharmacological modulator appear to be synergistic. Treatment of macrophages with SR1903 resulted in nearly complete blockade of activation of TREM-1 expression and cell surface protein whereas treatment with the selective LRX agonist GW3965 only had modest impact on TREM-1 expression and little effect on cell surface protein levels. Excessive inflammation can lead to tissue and organ damage and as such, this observation suggests that SR1903 may serve as a potential therapeutic for innate immune disorders. While a link between PPARγ and TREM-1 has been suggested[9] and here we demonstrate the ability of PPARγ to repress TREM-1 expression, additional mechanistic studies are required to dissect the direct action of SR1903 on TREM-1 and the crosstalk between RORγ and PPARγ, and perhaps LXR. The observation that SR1903 treatment resulted in increased expression of SENP3 (SUMO1/Sentrin/SMT3 specific peptidase 3) suggests the action of this compound may be via modulation of the SUMO status of proteins where SUMO is known to play a role in the controlling nuclear receptor activity both positively and negatively. Future proteomic studies are required to dissect the role of sumoylation on the action of SR1903. Regardless, the data presented described below suggests that the targeted poly-pharmacological modulator SR1903 represents a strategy for treatment of inflammatory disease.

Given the role of PPARγ, LXR, and RORγ in immune regulation, and the distinct pharmacological profile of SR1903 from previously reported studies with RORγ modulators, the Examples below describe additional testing of SR1903. Pharmacological and pharmacokinetic studies demonstrate that the compound was very well tolerated following chronic administration which facilitated detailed analysis of SR1903 in murine models of autoimmune and metabolic disease. The results described below suggest that the polypharmacological modulator SR1903, unlike selective RORγ inverse agonists, preserves the thymus while retaining potent anti-inflammatory effects in animal models of autoimmune disease.

The present disclosure thus, in an embodiment, shows the polypharmacological modulator SR1903 preserves the thymus, unlike the selective RORγ inverse agonist SR2211 as shown in Chang et al. (2014)[4]. The compound SR1903, in various embodiments, retains potent anti-inflammatory effects in animal models of autoimmune disease.

In certain embodiments, the present invention is directed to methods of inhibiting TREM-1 in a subject in need thereof comprising administering an effective amount of a compound having Formula (I), such as SR1903, or a pharmaceutically acceptable salt thereof. The invention is also directed to a method of treating an inflammatory disease or condition, an autoimmune disease, obesity, and/or a metabolic disease or disorder in a subject in need thereof comprising administering to said subject an effective amount of a compound having Formula (I), such as SR1903, or a pharmaceutical salt thereof. The invention is also directed to the treatment of castration resistant prostate cancer.

The present invention is additionally directed to methods of inhibiting TREM-1 in a subject in need thereof comprising administering an effective amount of a compound that is a RORγ inverse agonist, and that is also an inverse agonist of PPARγ and/or an agonist of LXR; preferably, the compound is a RORγ inverse agonist, an inverse agonist of PPARγ and an agonist of LXR. The invention is also directed to a method of treating an inflammatory disease, condition, or disorder, an autoimmune disease, obesity, and/or a metabolic disease in a subject in need thereof comprising administering to said subject an effective amount of a compound that is a RORγ inverse agonist, and that is also an inverse agonist of PPARγ and/or an agonist of LXR; preferably, the compound is a RORγ inverse agonist, an inverse agonist of PPARγ and an agonist of LXR.

SR1903 is described in U.S. Pat. No. 9,586,928 (the contents of which are expressly incorporated by reference herein) as a RORγ inverse agonist. The chemical name of SR1903 is 1,1,1,3,3,3-hexafluoro-2-(2'-methyl-4'-((4-(pyridin-4-ylmethyl)piperazin-1-yl)methyl)-[1,1'-biphenyl]-4-yl) propan-2-ol and the chemical structure is shown above and in FIG. 1A.

The Examples below demonstrate that SR1903 possesses anti-inflammatory and anti-diabetic properties in the collagen-induced arthritis (CIA) and diet-induced obesity (DIO) mouse models, respectively. Obesity and rheumatic disease are mechanistically linked via chronic inflammation. The orphan receptor, TREM-1, is a potent amplifier of pro-inflammatory and non-infectious immune responses. The Examples show that SR1903 effectively blocks TREM-1 activation. As discussed above, SR1903 is different from close structural analogs (such as certain other compounds described in U.S. Pat. No. 9,586,928) in that it has modest agonist activity on LXR and weak repressive activity (or more specifically, inverse agonism) of PPARγ. RORγ, LXR, and PPARγ play essential roles in inflammation and metabolism. In the context of obesity, SR1903 aided in the maintenance of thymic homeostasis unlike selective RORγ inverse agonists. As shown herein, SR1903 was well-tolerated following chronic administration. SR1903 can thus be used for the treatment of metabolic and inflammatory disease, and/or for treating disease or conditions mediated or related to TREM-1, and/or for inhibiting TREM-1. In addition, the ability of SR1903 to block lipopolysaccharide (LPS) signaling indicates that the compound can be used to treat innate immune response disorders. The magnitude of the inflammatory response is amplified by the TREM-1 pathway, which is upregulated on neutrophils and monocytes that infiltrate infected tissues. The ability of the polypharmacological modulator SR1903 to block LPS-mediated signaling via blockade of TREM-1 induction suggests a small molecule therapeutic approach to target TREM-1 for the treatment of innate immune response disorders.

The invention includes a method of inhibiting TREM-1 in a subject in need thereof comprising administering to said subject an effective amount of a compound that has RORγ inverse agonist activity, LXR agonist activity, and PPARγ inverse agonist activity. In certain aspects, the compound is SR1903 or a compound with similar activity.

The phrases "related to triggering receptor expressed on myeloid cells-1," "mediated by triggering receptor expressed on myeloid cells-1" "related to TREM-1," "TREM-1 mediated," and the like in the context of diseases, disorders or conditions (for example, "a condition mediated by TREM-1" or a "condition related to TREM-1") are used interchangeably herein. The diseases and conditions that are encompassed include those diseases or conditions in which inhibition of TREM-1 is therapeutically useful, and/or where the activity of TREM-1 is detrimental. TREM-1 has, for example, been described as playing a role in inflammatory disorders of both infectious and non-infectious etiology (Roe et al., 2014. Triggering receptor expressed on myeloid cells-1 (TREM-1): a new player in antiviral immunity? *Front Microbiol.* 5: 627; the contents of which are expressly incorporated by reference herein). Thus, the compounds described herein are useful for treating inflammatory diseases or conditions that are pathogen-associated as well as those that are not pathogen-associated or have non-infectious etiology. The terms "disease," "disorder," and "condition" can be used interchangeably, for example, in reference to inflammatory diseases (or disorders) or metabolic diseases (or disorders).

The invention encompasses a method of inhibiting TREM-1 in a subject in need thereof comprising administering to said subject an effective amount of a compound having the formula (I):

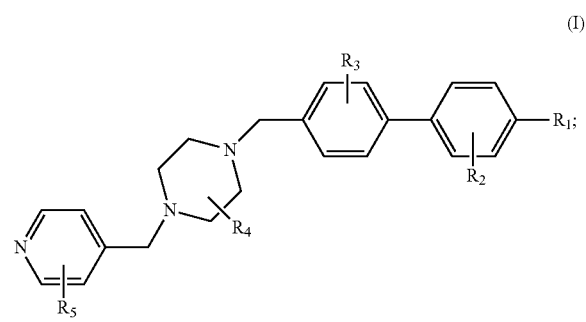

(I)

wherein:

$R_1$ is C1-C4 alkyl substituted with OR or C1-C4 fluoroalkyl substituted with OR;

$R_2$, $R_4$, and $R_5$ are each independently selected from the group consisting of hydrogen, halo, C1-C4 alkyl, and C1-C4 alkoxy;

$R_3$ is C1-C4 alkyl; and

R is hydrogen or C1-C4 alkyl; or a pharmaceutically acceptable salt thereof.

In certain aspects the compound, has the formula (Ia):

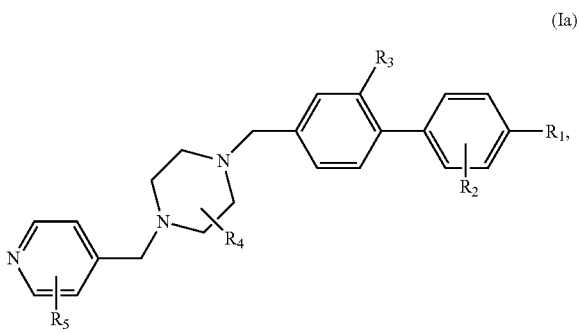

(Ia)

or is a pharmaceutically acceptable salt thereof. In certain specific aspects, $R_1$ is C1-C4 fluoroalkyl substituted with OH and/or $R_3$ is methyl. In preferred aspects, the compound is SR-1903, or a pharmaceutically acceptable salt thereof.

In certain aspects, the compound has the Formula (I) and has RORγ inverse agonist activity, LXR agonist activity, and PPARγ inverse agonist activity.

The present disclosure also provides in an embodiment a method for treating a subject suffering from a disease or condition that is related to triggering receptor expressed on myeloid cells-1 (TREM-1), comprising administering to the patient a therapeutically effective amount of the compound SR1903:

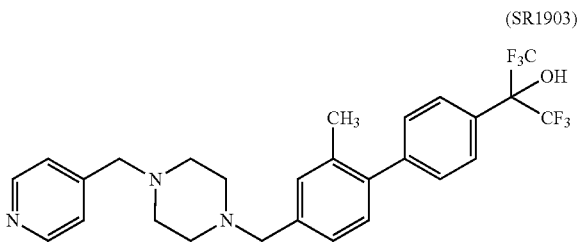 [SMILES: Cc1cc(CN2CCN(Cc3ccncc3)CC2)ccc1-c1ccc(C(O)(C(F)(F)F)C(F)(F)F)cc1]

(SR1903)

or a pharmaceutically acceptable salt thereof.

The methods and uses described herein can be further characterized, per various embodiments, by several surprising advantages. Thus, in an embodiment, administration of a compound of Formula (I) or SR1903 does not suppress the subject's immune response and/or preserves the subject's thymus and/or does not decrease intrathymic cell number. Convenient steps for verifying this entail measurements of the subject's T-cell count before and after administration of the compound of Formula (I) or SR1903. T-cell counts are readily established, for instance, by performing a routine blood test on the subject, such as a complete blood count (CBC) well-known to the skilled artisan. T-cell counts pre- and post-administration are substantially the same, such as within 10% or less of each other. In some embodiments, the T-cell counts are within 9%, 8%, 7%, 6%, 5%, 4%, 3%, 2%, 1% or less of each other.

In another embodiment, administration of the compound of Formula (I) or SR1903 surprisingly protects the subject from thymic involution. Thus, the compounds described herein can be used in methods of protecting a subject from thymic involution. In certain embodiments, the mass of the subject's thymus is measured before and after administration of the compound of Formula (I) or SR1903. In some instances, direct measurement of thymic mass in vivo may be impractical. Additional indices of thymic involution can be used, such as in a clinical setting. For example, quantitative measurement of overall thymic size can be assessed. Alternatively, or in addition, visual assessment with thymic scores provide a qualitative scoring of thymic involution. Any of these of indices are established, for example, by routing computed tomography (CT) scans of the subject's thymus. The pre- and post-administration masses, overall sizes, and/or qualitative scores of the thymus are substantially the same, such as within 10% or less of each other. In some embodiments, the pre- and post-administration indices are within 9%, 8%, 7%, 6%, 5%, 4%, 3%, 2%, 1% or less of each other.

In additional aspects, the conditions that can be treated according to the methods described herein include, for example, TREM-1 mediated inflammation and TREM-1 mediated metabolic disorders. The TREM-1 mediated inflammation can include, for example, an acute, sub-acute, or chronic inflammatory disorder, systemic inflammation, an innate immune response disorder, or an autoimmune disorder. The subject or patient, for example, can be suffering from chronic inflammation or a chronic inflammatory disease or disorder, including those of aging, inflammaging, and immunosenescence. Examples of chronic inflammatory diseases include, but are not limited to, rheumatic diseases, obesity, and/or a metabolic disease or inflammation secondary to metabolic syndrome and/or type II diabetes.

Non-limiting examples of inflammatory diseases or disorders and/or autoimmune diseases or disorders are inflammatory bowel disease (IBD), Crohn's disease (CD), ulcerative colitis (UC), irritable bowel syndrome, rheumatoid arthritis (RA), juvenile rheumatoid arthritis, ankylosing spondylitis, juvenile idiopathic arthritis (JIA), gout, Behcet's disease, psoriasis, psoriatic arthritis, lupus associated arthritis, systemic lupus erythematosus (SLE), lupus nephritis, type I diabetes, Grave's disease, multiple sclerosis (MS), autoimmune myocarditis, vasculitis, Kawasaki disease, coronary artery disease, chronic obstructive pulmonary disease, interstitial lung disease, autoimmune thyroiditis, scleroderma, systemic sclerosis, osteoarthritis, atopic dermatitis, lichen planus, vitiligo, graft versus host disease, Sjogrens's syndrome, autoimmune nephritis, Goodpasture's syndrome, chronic inflammatory demyelinating polyneuropathy, allergy, asthma, myasthenia gravis, diabetes mellitus (Type I or II), atherosclerosis, endotoxemia, exotoxemia such as poisoning or drug-induced (e.g., acetaminophen) liver injury, septicemia, sepsis, septic shock, multi-organ system failure, systemic inflammatory response syndrome (SIRS), vasculitis, vascular leak, renal failure, respiratory failure (including, for example, ARDS/SARS), hematologic dyscrasias, hemolytic anemias, coagulopathies including excessive clotting and bleeding, thrombotic microangiopathies, thrombocytopenia, disseminated intravascular coagulation (DIC), toxic shock syndrome, and autoimmune diseases that are a result of either acute, sub-acute, or chronic inflammation. The invention encompasses treatment of inflammatory disease or disorders related to infective and non-infective etiologies.

In certain specific aspects, the subject is suffering from rheumatoid arthritis, diabetes, obesity, inflammatory bowel disease, endotoxemia, septicemia, sepsis, septic shock, multi-organ system failure, systemic inflammatory response syndrome (SIRS), vasculitis, vascular leak, renal failure, respiratory failure (e.g., acute respiratory distress syndrome and/or severe acute respiratory syndrome), hematologic dyscrasias, hemolytic anemias, coagulopathies including excessive clotting and bleeding, thrombotic microangiopathies, thrombocytopenia, and disseminated intravascular coagulation. In certain aspects, the method is directed to the treatment of septic shock.

The invention encompasses treatment of systemic inflammation in a patient in need thereof. Systemic inflammation encompasses conditions characterized by a release of pro-inflammatory cytokines and an activated innate immune system which can be caused by biological factors, chemical factors, or by genetic factors. SIRS is a serious condition related to systemic inflammation, organ dysfunction, and organ failure. SIRS is nonspecific and can be caused by ischemia, inflammation, trauma, infection, or several insults combined. Thus, SIRS can be, but is not always, related to infection. In yet further aspects, the SIRS is cytokine release syndrome (CRS)/cytokine storm syndrome (CSS). The invention encompasses the treatment of multi-organ system failure, SIRS, respiratory failure, sepsis, septic shock, and systemic inflammation caused by any inciting factor or condition, including, but not limited, autoimmune response or disease, immune complex, allergen, tumor lysis syndrome, drug or toxin-induced, or physical/thermal stressors (e.g., exercise, cold, heat, trauma, or rhabdomyolysis), as well as those caused by a foreign pathogen or infection. In yet further aspects, the invention is directed to the treatment of ARDS and/or SARS induced by a respiratory infection, including, but not limited to, SARS CoV and SARS CoV-2/COVID-19 infections. In yet further aspects, the SIRS is cytokine release syndrome (CRS)/cytokine storm syndrome (CSS) associated with viral infections, including, but not limited to, SARS CoV and SARS CoV-2/COVID-19 infections.

The invention additionally encompasses the treatment of multi-system organ failure or organ damage, including, but not limited to, complement-driven anemia, hemodynamic collapse, for example, associated with microangiopathies, ARDS, hemolysis, capillary leak, disseminated intravascular coagulation (DIC), and paroxysmal nocturnal hemoglobinuria (PNH), for example. In certain aspects, the invention is directed to the treatment of thrombotic microangiopathies, including, for example, those associated with thrombotic thrombocytopenic purpura (TTP), hemolytic uremic syndrome (HUS), atypical hemolytic uremic syndrome (aHUS), posttransplant TMAs or transplant-associated TMAs, and hemolysis, elevated liver function tests, HELLP syndrome (hemolysis, elevated liver enzymes, and low platelets), DIC, drugs, malignancy, scleroderma-associated renal crisis, systemic lupus erythematosus (SLE), and malignant hypertension. Additional complement-driven anemias are described, for example, in Merrill et al. (2018). Complement-driven anemia: more than just paroxysmal nocturnal hemoglobinuria. *Hematology Am Soc Hematol Educ Program.* 30(1): 371.

The inflammatory bowel disease (IBD) can, for example, be IBD refractory to anti-TNF treatment, such as refractory Crohn's disease.

In certain specific embodiments, the subject or patient is suffering from a disease or condition selected from autoimmune disorders, inflammatory diseases, metabolic disorders, sepsis, viral immunity, and castration resistant prostate cancer (CRPC).

In additional specific embodiments, the subject or patient is suffering from an autoimmune disorder. Examples of autoimmune disorders include, in various embodiments, Hashimoto's thyroiditis, Pernicious anemia, Addison's disease, Type I diabetes, Rheumatoid arthritis, Systemic lupus erythematosus. Dermatomyositis, Sjogren syndrome, Lupus erythematosus, Multiple sclerosis, Myasthenia gravis, Reactive arthritis, Grave's disease, Crohn's disease, and Lupus.

In additional embodiments, the subject or patient is suffering from an inflammatory disease or disorder.

In yet another embodiment, the subject or patient is suffering from a metabolic disorder. For instance, in accordance with various embodiments, the disease or disorder is diabetes or obesity. Metabolic disorders also include metabolic syndrome and dyslipidemia.

Optionally in combination with any other embodiment described herein, per another embodiment, the subject or patient is suffering from castration resistant prostate cancer (CRPC).

In yet additional aspects, the invention is directed to the treatment of pathogen-associated inflammation or pathogen-associated infection and associated conditions resulting from reactive inflammation. The pathogen-associated infection can, for example, be a bacterial, parasitic, fungal, or viral infection. In certain aspects, the invention is directed to the treatment of virus or viral infection-associated inflammation. Inflammatory responses to certain viral infection can be protective/regulated inflammation or pathogenic/dysregulated inflammation (Channappanavar et al. (2017). Pathogenic human coronavirus infections: causes and consequences of cytokine storm and immunopathology. Semin Immunopathol 39(5): 529-539). The compounds of the invention can be used to treat virus-associated pathogenic/dysregulated inflammation. The role of TREM-1 in viral infection has been described, for example, in Roe et al., 2014. Triggering receptor expressed on myeloid cells-1 (TREM-1): a new player in antiviral immunity? *Front Microbiol.* 5: 627 and Amrun et al., 2020. TREM-1 activation is a potential key regulator driving severe pathogenesis of enterovirus A71 infection. *Sci Rep* 10: 3810; the contents of each of which are expressly incorporated by reference herein. Amrun et al., for example, showed that reduced TREM-1 expression mitigates enterovirus A71 (EV-A71) infection. Roe et al. posited that TREM-1 signaling may promote inflammation and tissue damage and thus contribute to disease pathogenesis of acute viral infections, including influenza and alphaviruses. In certain specific aspects, the invention is directed to treatment of inflammation associated with viral infection, including acute viral infection. Non-limiting examples of viruses include orthomyxoviruses (influenza virus), filoviruses (Ebola and Marburg viruses), flaviviruses (DENV, WNV, and TBEV), alphaviruses (CHIKV), and coronaviruses (highly pathogenic coronaviruses include, for example, severe acute respiratory syndrome CoV (SARS-CoV), Middle East respiratory syndrome CoV (MERS-CoV) and SARS-CoV-2/COVID-19). For example, inflammation associated with hCoVs includes elevated pro-inflammatory cytokine/chemokine responses resulting in acute lung injury (ALI), and acute respiratory distress syndrome (ARDS) (Channappanavar et al. (2017). Pathogenic human coronavirus infections: causes and consequences of cytokine storm and immunopathology). The compounds described herein can be used to treat cytokine storm, acute lung injury, and/or ARDS, including those associated viral infection, including, but not limited to, highly pathogenic coronaviruses.

With respect to blockade of RORγ function, the literature identifies a risk of thymic alterations and a risk of T-cell lymphoma development as a result of sustained pharmacological inhibition of RORγ. In addition, it has been reported that thymic aberrations resulted after prolonged treatment of rats with a RORγ inhibitor which were similar to those observed in RORγ/RORγt mice prior to development of thymic T-cell lymphoma (Guendisch U, Weiss J, Ecoeur F, et al. Pharmacological inhibition of RORγt suppresses the Th17 pathway and alleviates arthritis in vivo. *PLoS One*. 2017; 12(11):e0188391. Published 2017 Nov. 20. doi: 10.1371/journal.pone.0188391). It would therefore be advantageous to provide a compound which inhibits RORγ but preserves the thymus while retaining anti-inflammatory effects.

The compounds described herein including SR1903 have been identified as preserving thymic function, for example, as measured by intrathymic cell number compared to the effect of selective RORγ inverse agonists such as SR2211. In addition, the compounds described herein are useful in reducing, delaying, or mitigating age- or obesity-related thymic involution. With respect to obesity, obesity has been described as accelerating thymic aging and/or accelerating thymic involution. With respect to aging, involution of the thymus and a decrease in the number of naïve CD4+ and CD8+ T cells are biomarkers of immunosenescence in humans (Salminen et al. (2019), Immunosenescence: the potential role of myeloid-derived suppressor (MDSC) in age-related immune deficiency, Cell. Mol. Life Sci. (2019). https://doi.org/10.1007/s00018-019-03048-x; the contents of which are expressly incorporated by reference herein). The compounds and methods described herein can be used for the treatment of chronic low-grade inflammation associated with the aging process, or inflammaging. In certain aspects, the compounds and methods described herein are used to enhance an immune response in a subject exhibiting inflammaging or immunosenescence. Indicators of immunosenescence are a decrease in the numbers of naïve $CD4^+$ and $CD8^+$ T cells, an imbalance in the T cell subsets, a decrease in T cell receptor (TCR) repertoire and signaling, and a decrease in B cell lymphopoiesis and a reduction in antibody production (Salminen et al.).

The compounds can also be used to treat or reduce thymic involution, including for example, obesity- or age-related thymic involution.

The compounds described herein preserve thymic function, for example, thymic function is preserved as compared to selective RORγ inverse agonists. A selective RORγ inverse agonist can be a compound that is inactive with respect to modulation of a nuclear receptor other than RORγ (such as LXR and/or PPARγ); or the modulation of the ROR takes place at a concentration ineffective for modulation of a nuclear receptor other than a RORγ (such as LXR and/or PPARγ). A selective RORγ inverse agonist can be inactive with respect to modulation of another nuclear receptor, such as LXRC or LXRB, or the modulation of a ROR can be selective at some concentration with respect to modulation of another nuclear receptor, such as an LXR or PPARγ, providing an effect free of side effects resulting from modulation of a non-target nuclear receptor. An example of a selective RORγ inverse agonist is SR2211. In certain aspects, the selective RORγ inverse agonist is one that does not inhibit TREM-1. As described above, preservation of thymic function and/or lack of suppression of an immune response can be determined by measuring a subject's T-cell count before and after administration of the compound as described herein. In yet other aspects, the effect on thymic function is measured, for example by measuring T-cell count, is compared with that of a selective RORγ inverse agonist.

In yet additional aspects, the invention is directed to a method of treating obesity and/or a metabolic disease or disorder comprising administering an effective amount of a compound of Formula (I), such as SR1903, wherein thymic function is preserved, for example, as measured by intrathymic cell number. As described below, intrathymic cell number was enriched in SR1903-treated mice and secondary lymphoid organs such as lymph node and spleen had similar cell number to that of the vehicle-only control mice. In certain aspects, intrathymic cell number is compared to that before administration of the compound of Formula (I) (such as SR1903) and/or the effect of selective RORγ inverse agonists such as SR2211.

In yet additional aspects, the invention is directed to a method of reducing obesity-related thymic involution comprising administering to a subject in need thereof an effective amount of a compound of Formula (I), such as SR1903.

Certain modulators of RORγ, including inverse agonists, are described in U.S. Pat. No. 9,586,928. Compounds that can be used to inhibit TREM-1 as described herein include compounds that have RORγ inverse agonist activity, LXR agonist activity, and PPARγ inverse agonist activity and can, for example, be selected from the compounds described in U.S. Pat. No. 9,586,928. An example of such a compound is SR1903.

It is within ordinary skill to evaluate a compound, such as those described herein or in U.S. Pat. No. 9,586,926, for effectiveness in modulation of RORγ, including for example, inverse agonism of RORγ in various cellular and biochemical assays using the procedures, for example, in U.S. Pat. No. 9,586,926 or described in the scientific literature. It is also within ordinary skill to evaluate a compound, such as those described herein or in U.S. Pat. No. 9,586,926, for effectiveness in modulation of the nuclear receptors LXRα and LXRβ in various cellular and biochemical assays using the procedures described in U.S. Pat. No. 9,586,926 or described in the scientific literature. It is additionally within the purview of the skilled person to evaluate a compound, such as those described herein or in U.S. Pat. No. 9,586,926, for effectiveness in modulation and/or repression and/or inverse agonism of PPARγ using the procedures described, for example, in U.S. Pat. Nos. 8,957,093, 9,309,227, 9,051, 265, and 10,016,394, and PCT Application Publication Nos. WO2013078233 and WO2013078237, the contents of each of which are expressly incorporated by reference herein, or as described in the scientific literature.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

A "small molecule" refers to an organic compound, including an organometallic compound, of a molecular weight less than about 2 kDa, that is not a polynucleotide, a polypeptide, a polysaccharide, or a synthetic polymer composed of a plurality of repeating units.

As to any of the groups described herein, which contain one or more substituents, it is understood that such groups do not contain any substitution or substitution patterns which are sterically impractical and/or synthetically non-feasible. In addition, the compounds of this disclosed subject matter include all stereochemical isomers arising from the substitution of these compounds.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium (1H), deuterium (2H), or tritium (3H) in any combination. Similarly, any carbon atom or set thereof in a molecule can be any of the isotopic form of carbons, such as 11C, 12C, or 14C, or any nitrogen atom or set thereof in a molecule can be any of the isotopic forms of nitrogen, such as 13N, 14N, or 15N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or 14C radiolabeled sample where only some fraction of the set of molecules making up the macroscopic sample contains a radioactive atom. It is also understood that many elements that are not artificially isotopically enriched themselves are mixtures of naturally occurring isotopic forms, such as 14N and 15N, 32S and 34S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, 14C and 3H can be prepared using neutrons generated in a nuclear reactor. Following nuclear transformation, 14C and 3H are incorporated into precursor molecules, followed by further elaboration as needed.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like. For example, the group —C(OH)(CF$_3$)$_2$ is a hydroxy-substituted haloalkyl (i.e., fluoroalkyl) group within the meaning herein. A fluoroalkyl group can be fully or partially fluorinated.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like. A fluoroalkoxy group can be fully or partially fluorinated.

A "hydroxyhaloalkyl" as the term is used herein refers to an alkyl group bearing at least one hydroxy group and at least one halo group. For example, a 1-hydroxy-1-trifluoromethyl-2,2,2-trifluoroethyl group is a hydroxyhaloalkyl group within the meaning herein.

The term "($C_x$-$C_y$)perfluoroalkyl" wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$. A perfluoroalkyl group encompasses a fully fluorinated fluoroalkyl group.

The term "($C_x$-$C_y$)perfluoroalkylene," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkylene, more preferred is —($C_1$-$C_3$)perfluoroalkylene, most preferred is —$CF_2$—.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein. Lists of many suitable salts are also found in *Remington's Pharmaceutical Sciences,* 17th ed., Mack Publishing Company, Easton, Pa., (1985), 1418, and the disclosure of which is incorporated herein by reference.

The invention includes pharmaceutically acceptable salts of the compound of Formula (I). In addition, hydrates, solvates, prodrugs, and metabolites are encompassed.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemical agents within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985. As used herein, the term "prodrug" refers to any pharmaceutically acceptable form of compound of the invention which, upon administration to a patient, provides a compound of the invention. Pharmaceutically acceptable prodrugs refer to a compound that is metabolized, for example hydrolyzed or oxidized, in the host to form a compound of the invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

As used herein, the term "metabolite" refers to any compound produced in vivo or in vitro from the parent drug of the invention, or any of its prodrugs that are converted biologically to a parent drug of the invention and then to a further biotransformation product of the parent drug.

The present invention further embraces the use of isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds described herein and intermediates may be isolated from their reaction mixtures and purified by standard techniques such as filtration, liquid-liquid extraction, solid phase extraction, distillation, recrystallization or chromatography, including flash column chromatography, or HPLC.

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

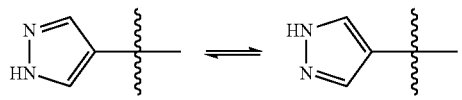 [SMILES: *c1cn[nH]c1 ; *c1cn[nH]c1]

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

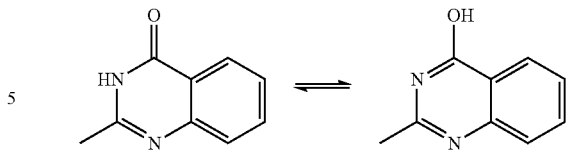

is an example of tautomerism. Accordingly, a structure depicted herein as one tautomer is intended to also include the other tautomer.

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated as having an (R) absolute configuration, and if the descending rank of the other groups proceeds counterclockwise, the molecule is designated as having an (S) absolute configuration. In the example in the Scheme below, the Cahn-Ingold-Prelog ranking is A>B>C>D. The lowest ranking atom, D is oriented away from the viewer. The solid wedge indicates that the atom bonded thereby projects toward the viewer out of the plane of the paper, and a dashed wedge indicates that the atom bonded thereby projects away from the viewer out of the plan of the paper, i.e., the plane "of the paper" being defined by atoms A, C, and the chiral carbon atom for the (R) configuration shown below.

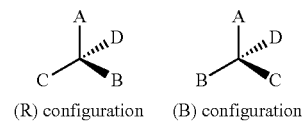

(R) configuration    (B) configuration

A carbon atom bearing the A-D atoms as shown above is known as a "chiral" carbon atom, and the position of such a carbon atom in a molecule is termed a "chiral center." Compounds of the invention may contain more than one chiral center, and the configuration at each chiral center is described in the same fashion.

There are various conventions for depicting chiral structures using solid and dashed wedges. For example, for the (R) configuration shown above, the following two depictions are equivalent:

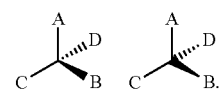

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Another aspect of an embodiment of the invention provides compositions of the compounds of the invention, alone or in combination with another medicament. As set forth herein, compounds of the invention include stereoisomers, tautomers, solvates, prodrugs, metabolites, pharmaceutically acceptable salts and mixtures thereof. Compositions containing a compound of the invention can be prepared by conventional techniques, e.g. as described in Remington: *The Science and Practice of Pharmacy,* 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

In various embodiments, the invention provides a dosage form adapted for administration to a patient afflicted with a condition described herein, wherein the dosage form comprises a capsule, a tablet, a liquid or dispersed oral formulation, or a formulation adapted for parenteral administration.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Generally, the initial therapeutically effective amount of SR1903, or a compound of Formula (I), or a pharmaceutically acceptable salt thereof that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 0.1 mg to about 1000 mg of SR1903 or a compound of Formula (I), or a pharmaceutically acceptable salt thereof. In another embodiment, such dosage forms contain from about 50 mg to about 500 mg of SR1903, or a compound of Formula (I), or a pharmaceutically acceptable salt thereof. In yet another embodiment, such dosage forms contain from about 25 mg to about 200 mg SR1903, or a compound of Formula (I), or a pharmaceutically acceptable salt thereof. In still another embodiment, such dosage forms contain from about 10 mg to about 100 mg of SR1903, or a compound of Formula (I), or a pharmaceutically acceptable salt thereof. In a further embodiment, such dosage forms contain from about 5 mg to about 50 mg of SR1903, or a compound of Formula (I), or a pharmaceutically acceptable salt thereof. In any of the foregoing embodiments the dosage form can be administered once a day or twice per day, for example.

The compositions of the present disclosure can be administered orally, topically, parenterally, by inhalation or spray or rectally in dosage unit formulations. The term parenteral as used herein includes subcutaneous injections, intravenous, intramuscular, intrasternal injection or infusion techniques. Suitable oral compositions as described herein include without limitation tablets, troches, lozenges, aqueous or oily suspensions, dispersible powders or granules, emulsion, hard or soft capsules, syrups or elixirs. In another embodiment, also encompassed are pharmaceutical compositions suitable for single unit dosages that comprise SR1903, or a compound of Formula (I), or a pharmaceutically acceptable salt thereof and a pharmaceutically acceptable carrier.

The compositions of the present disclosure that are suitable for oral use may be prepared according to any method known to the art for the manufacture of pharmaceutical compositions. For instance, liquid formulations of the compounds of the present disclosure contain one or more agents selected from the group consisting of sweetening agents, flavoring agents, coloring agents and preserving agents in order to provide pharmaceutically palatable preparations of SR1903, or a compound of Formula (I), or a pharmaceutically acceptable salt thereof.

For tablet compositions, SR1903, or a compound of Formula (I), or a pharmaceutically acceptable salt thereof in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, SR1903, or a compound of Formula (I), or a pharmaceutically acceptable salt thereof is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending SR1903 or a pharmaceutically acceptable salt thereof in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide SR1903 or a pharmaceutically acceptable salt thereof in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compound SR1903, or a compound of Formula (I), or a pharmaceutically acceptable salt thereof may also be administered in the form of suppositories for rectal administration. These compositions can be prepared by mixing the compound with a suitable non-irritating excipient which is solid at ordinary temperatures but liquid at the rectal temperature and will therefore melt in the rectum to release the compound. Exemplary excipients include cocoa butter and polyethylene glycols.

Compositions for parenteral administrations are administered in a sterile medium. Depending on the vehicle used and concentration the concentration of SR1903, or a compound of formula (I) or a pharmaceutically acceptable salt thereof in the formulation, the parenteral formulation can either be a suspension or a solution containing dissolved compound. Adjuvants such as local anesthetics, preservatives and buffering agents can also be added to parenteral compositions. Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

The compounds of the invention can be administered to a mammal, especially a human in need of such treatment, prevention, elimination, alleviation or amelioration of a malcondition, disease, disorder, or condition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 g to about 1250 mg, preferably from about 250 g to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively, dosage forms can be administered less frequently than daily, such as every other day, or weekly, if found to be advisable by a prescribing physician.

The invention is illustrated by the following examples which are not meant to be limiting in any way.

EXAMPLES

Example 1: Targeted Polypharmacology Blocks Inflammatory Signaling Pathways

Figure 1B:
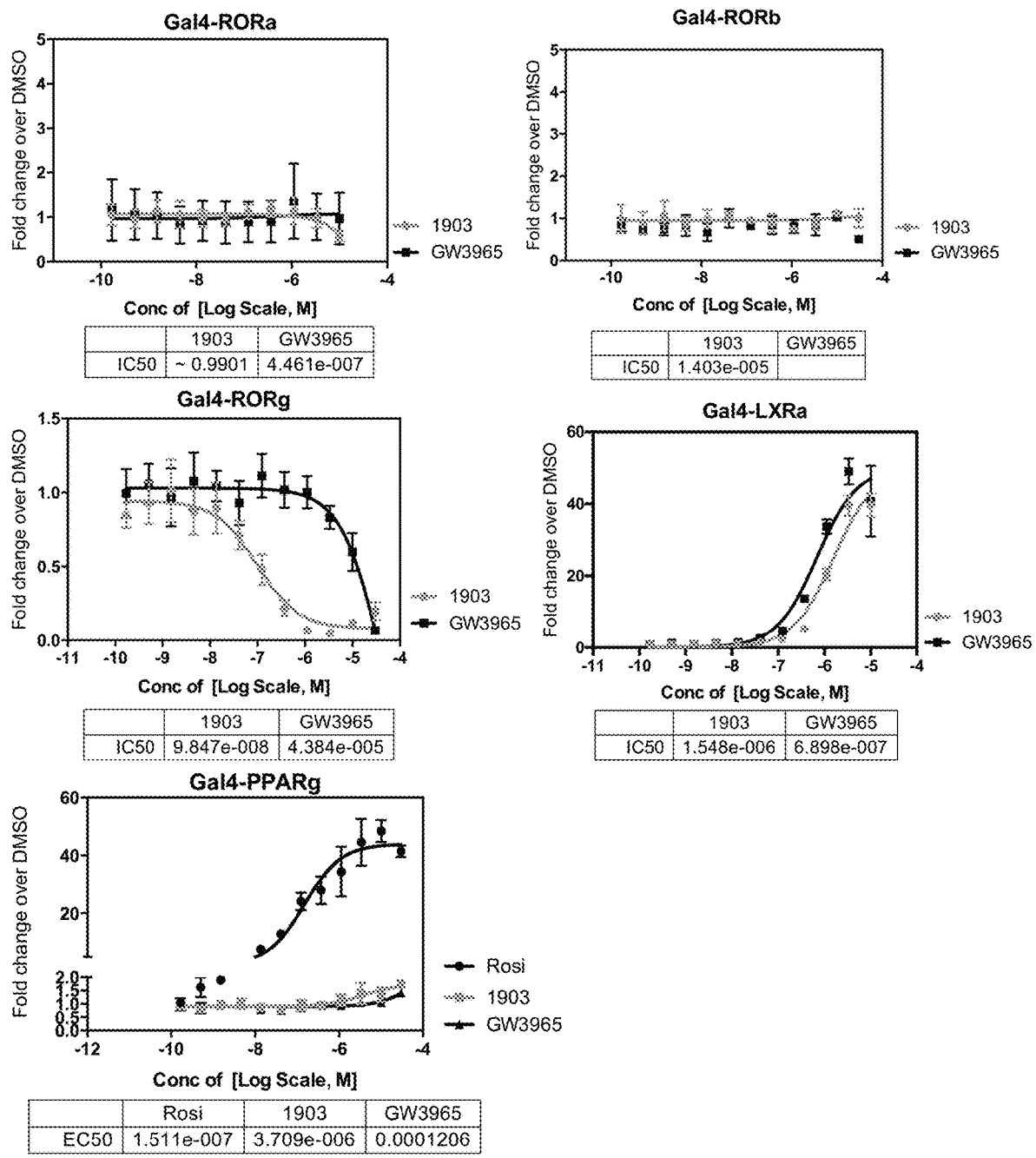

Following the discovery that the LXR agonist T0901317 functions as an inverse agonist of RORα and RORγ, SAR studies led to the development of potent and isoform selective modulators including the RORγ inverse agonists SR2211 and SR1903. Despite similar chemical structures of these compounds (FIG. 1A) and similar potency on RORγ, studies in LPS-stimulated macrophages suggested divergence in functional activity for these compounds. Based on these results, both molecules were screened in an assay containing additional nuclear receptors, revealing reduced specificity of SR1903 compared to SR2211 with activity on LXR and PPARγ receptors. As shown in FIG. 1B, SR1903 is considerably more potent on RORγ than the well characterized LXR agonist GW3965 ($IC_{50}$ 43 μM) with an $IC_{50}$ value of ~100 nM in a cell-based promoter-reporter Gal4 assay format, and both compounds lack activity on RORα and RORβ in the same assay format. Also as shown in FIG. 1B, further evaluation demonstrated that SR1903 possessed comparable LXR agonist activity to that for GW3965 with $EC_{50}$ values of 689 nM and 154 nM, respectively.

Figure 1D:
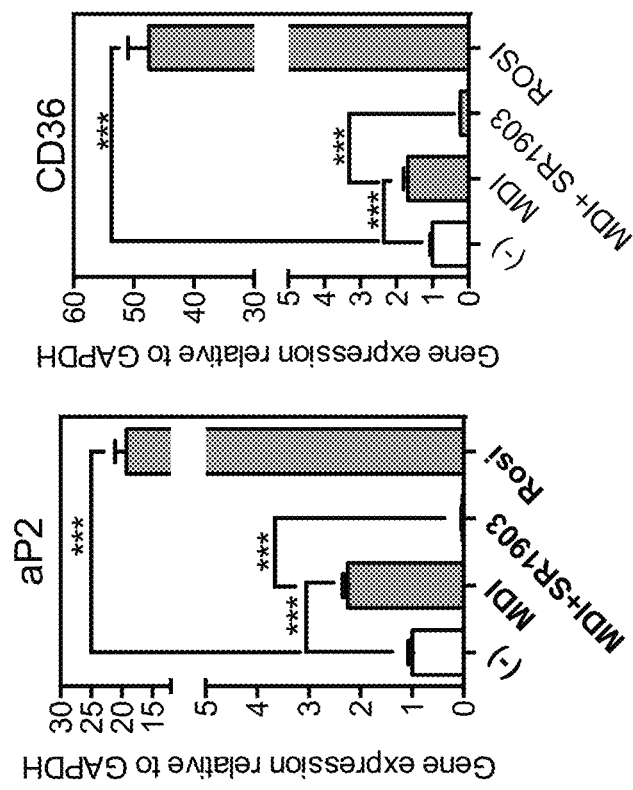
Figure 1C:
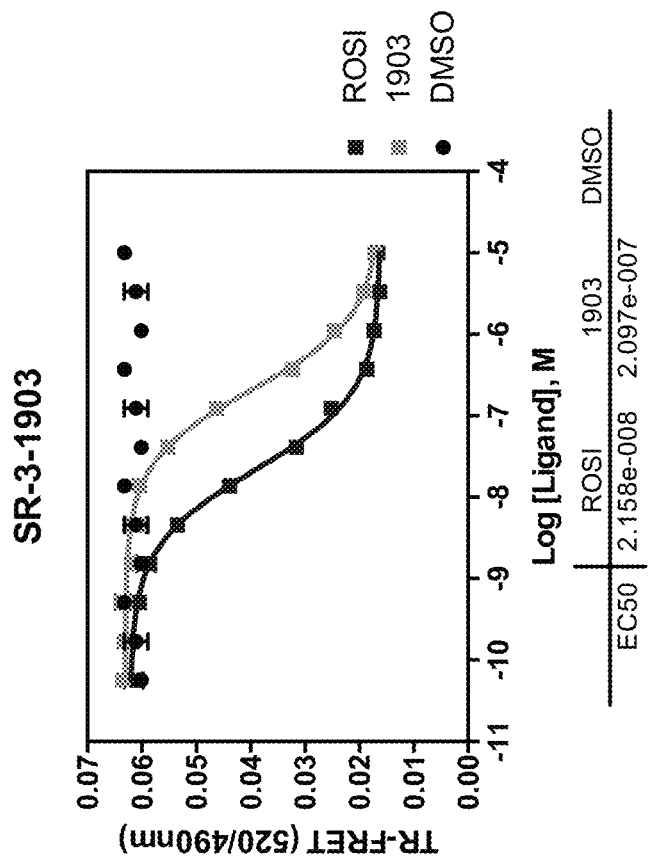

As shown in FIG. 1D, expression of the PPARγ target genes aP2 (FABP4) and the scavenger receptor CD36 were significantly repressed by SR1903 (99% and 87% repression, respectively, as compared to MDI treatment alone) in OP9 mesenchymal stem cells that are differentiated towards adipocytes (induced by MDI; methylisobutylxanthine+dexamethasone+insulin), indicating that SR1903 is an inverse agonist of PPARγ. Further analysis of SR1903 in a lanthascreen based competitive binding assay demonstrated that SR1903 had modest binding affinity for PPARγ (FIG. 1C) with an $IC_{50}$ value of 209 nM. Analysis of SR1903 in a Gal4 assay format for PPARγ activation demonstrated that while the compound binds the receptor, the compound lacks the ability to activate it, indicating that it likely functions as an antagonist or inverse agonist (FIG. 1B). The compound's profile in this assay was similar to that observed with treatment of well characterized PPARγ antagonists and inverse agonists[13-14].

Figure 6A:
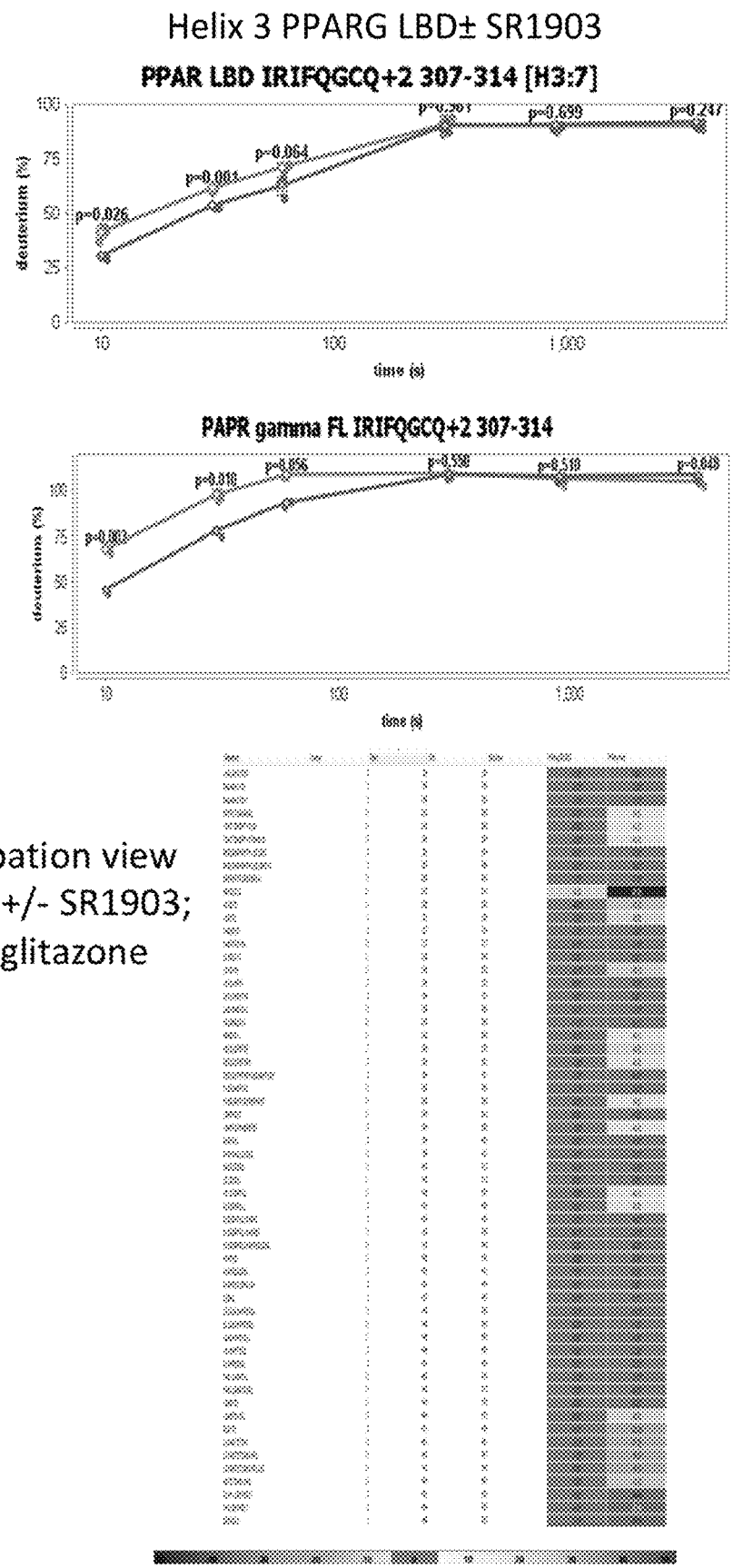
FIGS. 6A and 6B.
Figure 6B:
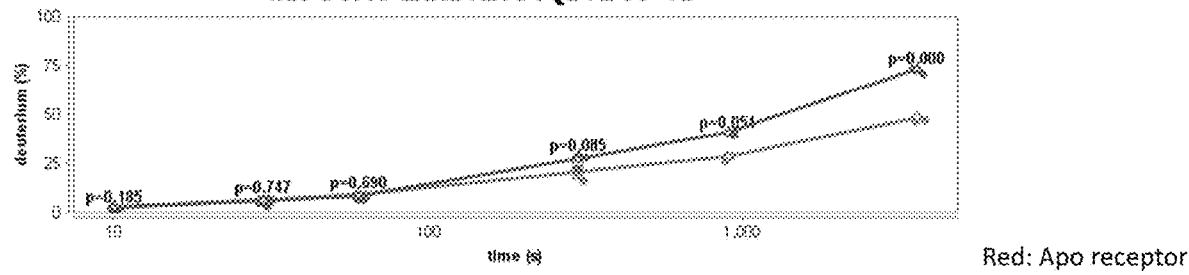
Figure 6B:
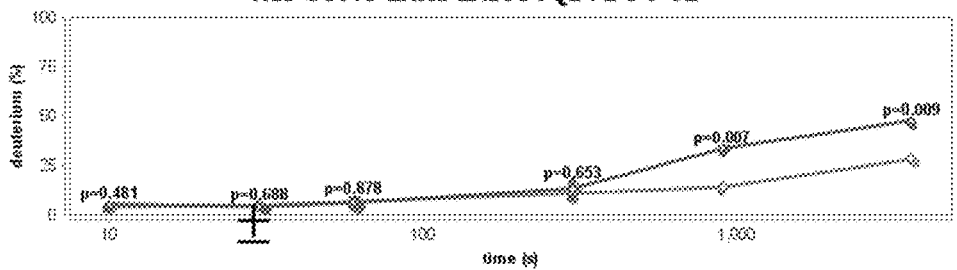
Figure 6B:
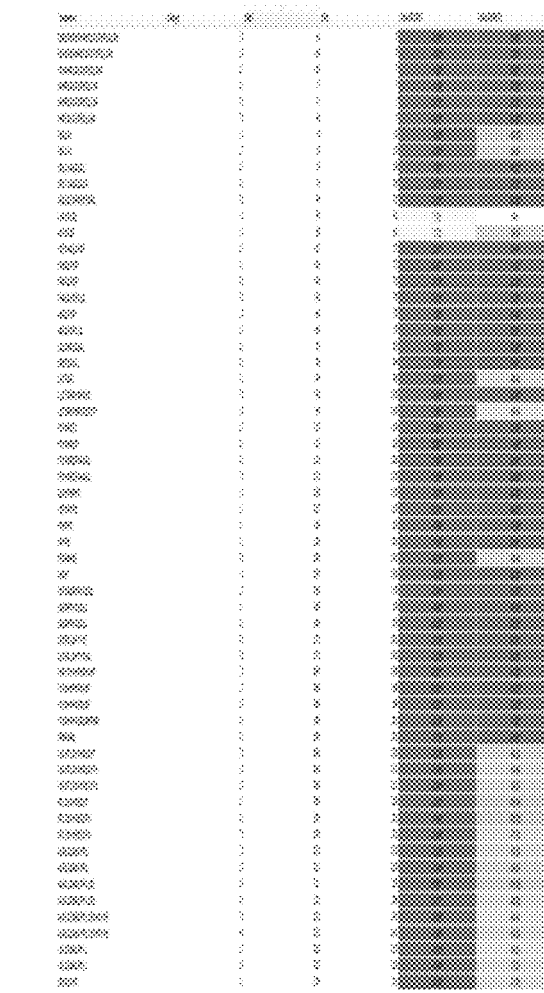
Figure 7:
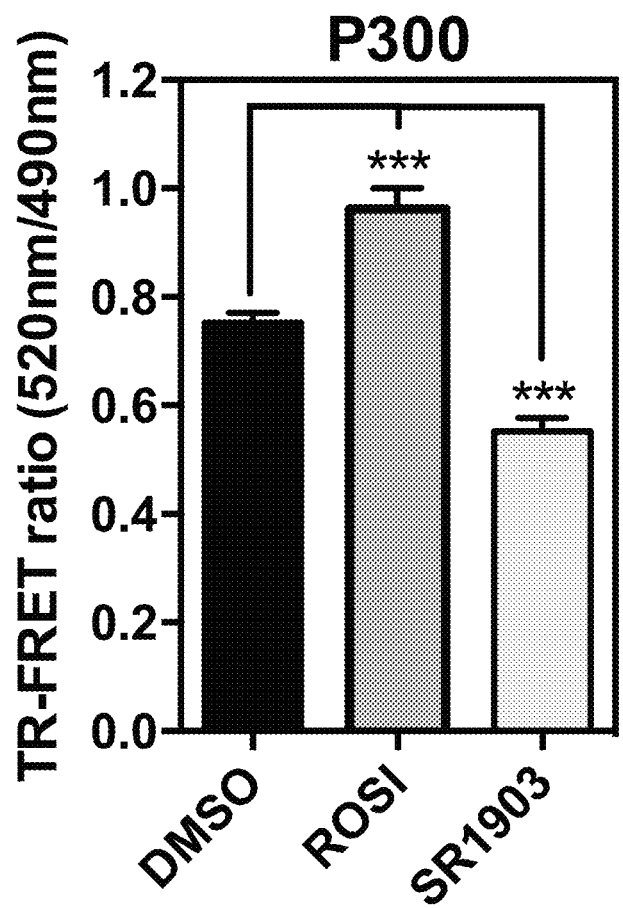
FIG. 7: NR box peptide recruitment assay. A TR-FRET-based interaction assay was used. Tb-anti-His antibody (10 nM; Invitrogen) and indicated ligand (1 uM) were incubated in complete TR-FRET PPAR assay buffer (Invitrogen) containing 10 nM purified His-PPARγ2 for 1 hr at room temperature. 450 nM FITC-labeled peptides p300 (sequence: ASKHKQLSELLRSGSS (SEQ ID NO: 1) was added and incubated for additional two hours (hrs) at room temperature (in dark). The FRET signal was measured by excitation at 340 nm and emission at 520 nm for fluorescein and 490 nm for terbium in Perkin Elmer ViewLux ultra HTS microplate reader. The fold change over DMSO was calculated by 520 nm/490 nm ratio. Each sample condition has four replicates. Graphs were plotted in GraphPad Prism as fold change of FRET signal for each compound over DMSO-only control.

Consistent with a direct interaction with PPARγ, differential HDX analysis of the receptor in the absence and presence of SR1903 revealed stabilization to deuterium exchange within helix 3, a region of the receptor that forms one surface of the ligand binding pocket (FIG. 6A; top left) that is critical for ligand binding. Stabilization of H12 (the activation helix) was not observed consistent with the compound's lack of agonist activity on PPARγ. Furthermore, SR1903 was tested in a lanthascreen based receptor NR-box peptide interaction assay using a peptide representative of a PPARγ coactivators (p300). Consistent with the reporter assay results, SR1903 disrupted PPARγ interaction with coactivator peptide p300 whereas the PPARγ agonist rosiglitazone increased the interaction with the p300 peptide (FIG. 7). Similar to that observed with PPARγ, differential HDX analysis of LXRα LBD in the absence and presence of SR1903 indicates that the compound makes a direct interaction with the receptor (FIG. 6A, top right) resulting in displacement of isolated endogenous ligand.

Figure 1E:
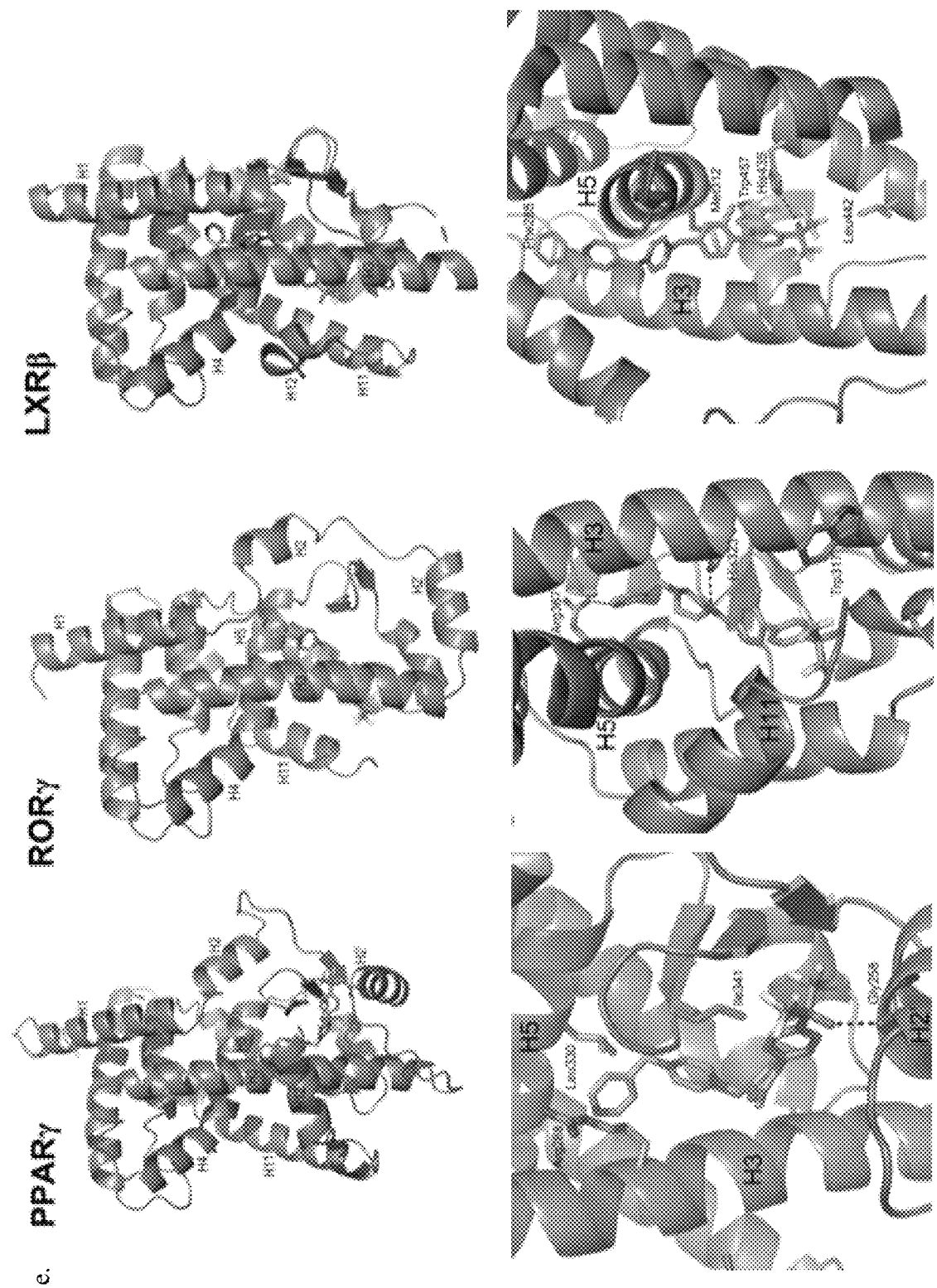

In silico docking of SR1903 with PPARγ, RORγ, and LXRβ LBDs was performed in order to elucidate plausible structural mechanisms of polypharmacology by the compound when in complex with the receptor. One mechanism of antagonism in PPARγ is through trapping helix 12 in the antagonist conformation which enables binding of corepressors[15-16]. Given the non-activating properties of SR1903 with PPARγ, the antagonist conformation of PPARγ was chosen as the scaffold receptor for docking. SR1903 docked between helix 3 and the β-sheet in the ligand binding pocket distal to the AF2 coactivator binding surface (FIG. 1E, left panels). This is consistent with the binding modes of SR10171 and SR11023 which do not interact with components of the AF2 surface, leaving H12 unrestrained and able to interact with ligands in the binding pose exhibited by SR1903 in the docked structure. Specifically, SR1903 forms a 3.0 Å hydrogen bond with the backbone oxygen of Gly258 as well as hydrophobic interactions with residues of the ligand binding pocket including Arg288, Leu330, and Ile341 (FIG. 1E, left bottom panel). The combination of a single hydrogen bond and several hydrophobic interactions is consistent with the ligand binding modes exhibited by SR10171 and SR11023, suggesting some conservation in this class of non-activating ligands of PPARγ.

The docking model of SR1903 with RORγ (FIG. 1E, middle panels) suggests that the mechanism of RORγ deactivation occurs through repositioning of W317 to prevent nucleation of H12. This mode of antagonism is shared with several other RORγ inverse agonists including the benzylsulfonamide class of RORγ modulators[17] and digoxin[18]. Specifically, the pyridine group of SR1903 is predicted to make a H-bond to R367, and the biaryl ring system makes hydrophobic contacts with H3 and the β-sheet region (FIG. 1E, middle bottom panel).

The binding mode of SR1903 revealed a putative mechanism of LXR agonism that is shared with the LXR agonist T0901317 (FIG. 1E, right panels)[19]. Specifically, the carbinol group of SR1903 provides a H-bond to H435 stabilizing the Histidine-Tryptophan switch that stabilizes H12 and AF2[20]. Also, the methyl group induces a twist in the biaryl ring system preventing them from being co-planer. This is predicted to lead to additional hydrophobic contacts within the pocket formed by H3, H5 and H11 leading to activation of LXR. These observations are consistent with previous findings that hydrophobic contacts in this region are key structural determinants for selectivity between the LXRs and RORs. Thus, this docking model helps explain the change in selectivity from that observed for SR2211 (lacking the methyl group) where the addition of the methyl group promotes LXR binding and subsequent activation through the carbinol group.

Figure 1F:
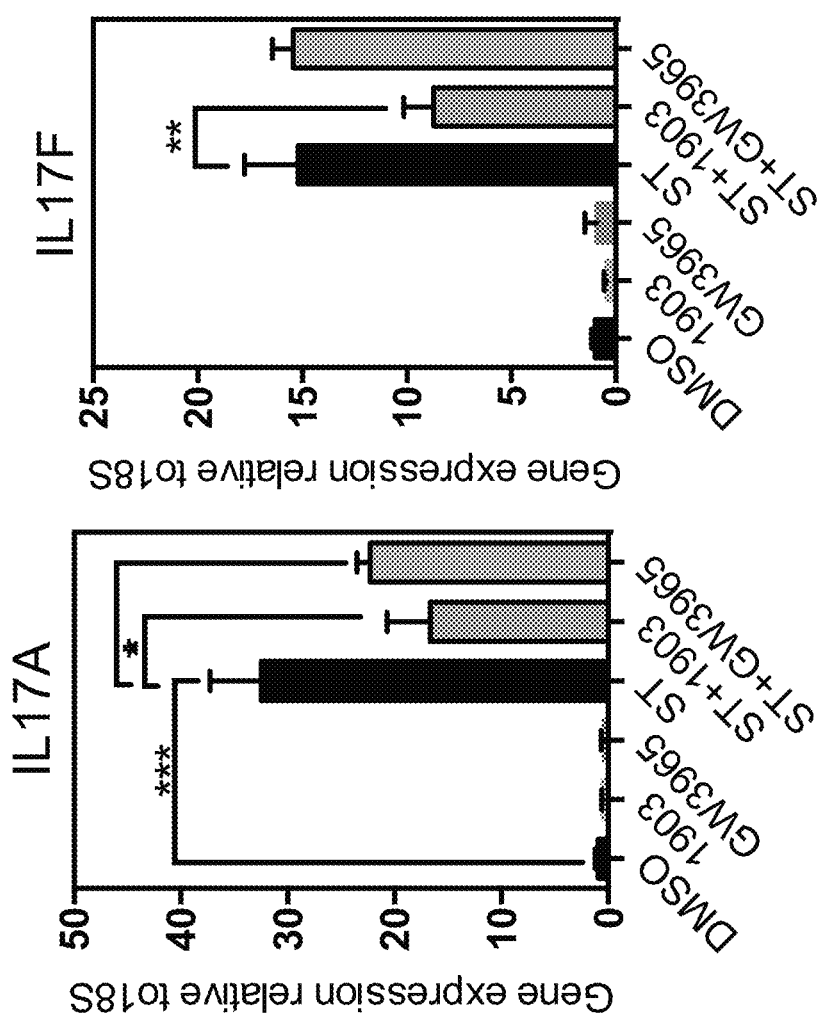
FIG. 1F are graphs showing RORγ target genes (IL17A and IL17F) expression in EL4 cells. 504 SR1903 and GW3965 were incubated overnight followed by PMA/ionomycin stimulation for 6 hrs.

To confirm the ability of SR1903 to repress endogenous RORγ target genes, PMA and ionomycin stimulated EL4 cells were treated with compound at 10 μM. Both IL17A and IL17F were repressed by SR1903 treatment as shown in FIG. 1F. Interestingly, similar effects were observed with the selective LXR agonist GW3965 on IL17A, but the compound lacked the ability to repress IL17F. Together along with additional data below, these results support that SR1903 functions as a potent RORγ inverse agonist, an agonist of LXR, and an inverse agonist of PPARγ.

Figure 2A:
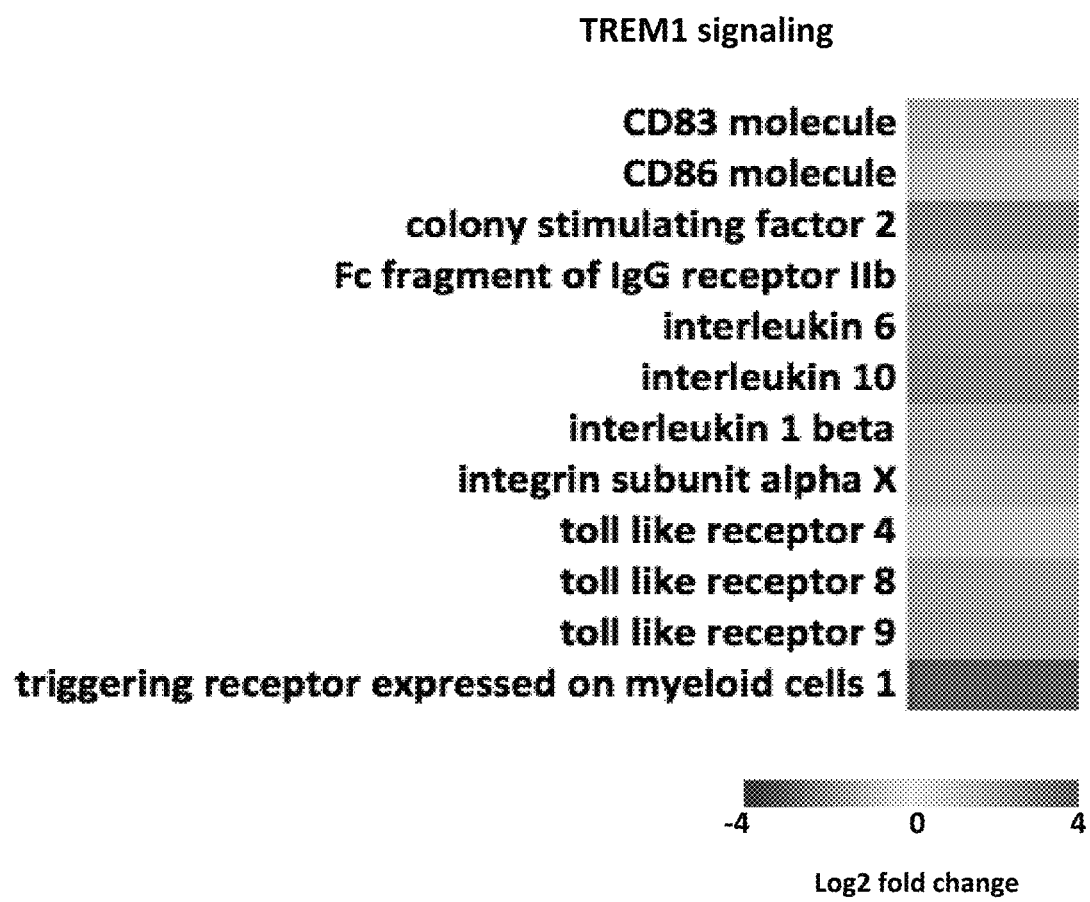
FIGS. 2A-2D: LPS signaling was repressed by the polypharmacological modulator SR1903.
Figure 2B:
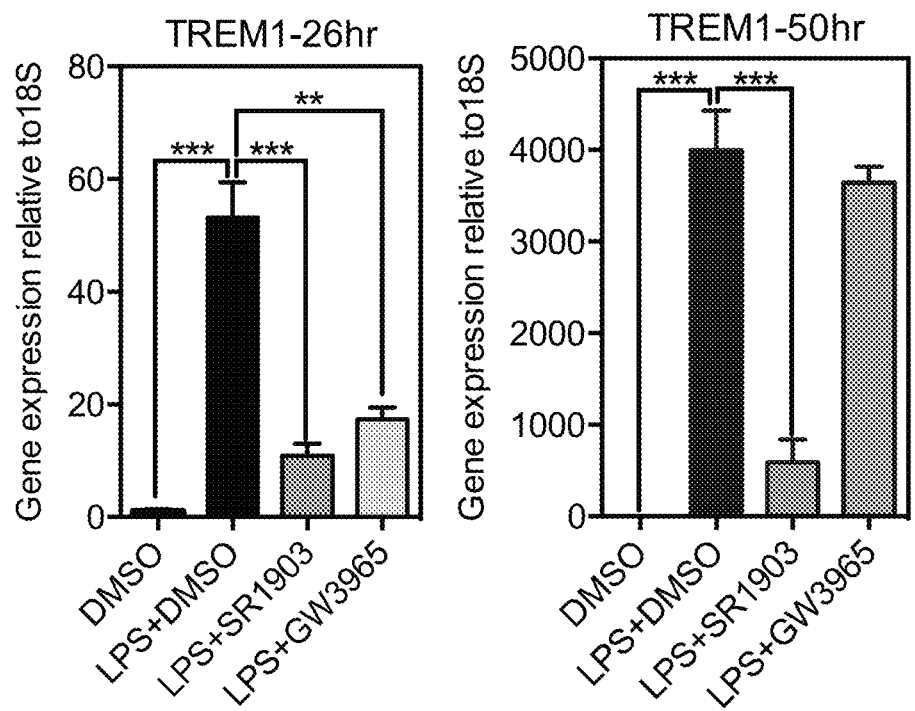

The nuclear receptors LXR and RORγ play key roles in modulating signaling pathways in immune cells. Macrophages, which are specialized differentiated mononuclear phagocytic cells, perform key roles in antimicrobial defense, autoimmunity, and inflammatory diseases[21]. Previously, it has been shown that the expression of RORγ is induced in innate immune cells upon infection[22] and in cultured RAW264.7 cells stimulated with LPS[1], whereas LXRs are regulators of cholesterol homeostasis and negatively regulate TLR signaling in macrophages[23]. To evaluate the effects of SR1903 on inflammatory signaling pathways in macrophages, expression profiling by RNA sequencing was performed on LPS-stimulated RAW264.7 cells treated with 10 μM compound compared to cells treated with DMSO-only. As shown in FIG. 2A and FIG. 10, LPS stimulation robustly increased the expression of triggering receptor expressed on myeloid cells 1 (TREM1) signaling, a protein that amplifies macrophage inflammatory responses triggered by infection[24] while SR1903 treatment significantly suppressed its expression. This observation was confirmed by qPCR where FIG. 2B shows that the induction of TREM-1 gene expression by LPS was significantly repressed by SR1903 and GW3965 treatment following 26 hr exposure. Only SR1903 maintained repression over the 50 hr treatment.

Figure 2C:
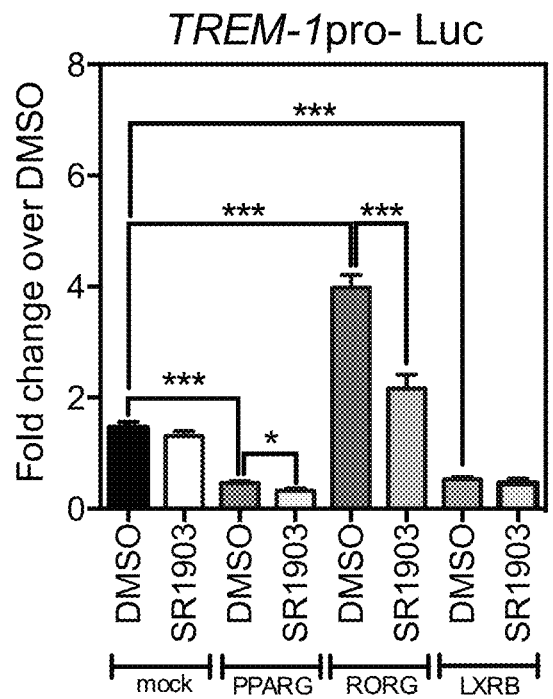

To determine if TREM1 gene expression is regulated by LXR, PPARγ or RORγ, we subcloned 3 kb murine TREM1 promoter region into pGL3 basic reporter vector. This TREM1-promoter reporter (luciferase) was co-transfected into cells with PPARγ, RORγ, or LXRβ each followed by treatment with SR1903 or DMSO. As shown in FIG. 2C, TREM1 promoter activity was induced ~4 fold by co-expression with RORγ compared with the mock vector co-transfection group, and this activity was attenuated by ~50% with SR1903 treatment. Unlike that observed with RORγ, co-expression with PPARγ and LXRβ repressed TREM1 activity and treatment with SR1903 had little effect. These results indicate that SR1903, in one embodiment, is capable of blocking activation of macrophages, a property that is useful in treatment of innate inflammatory disorders.

Figure 2D:
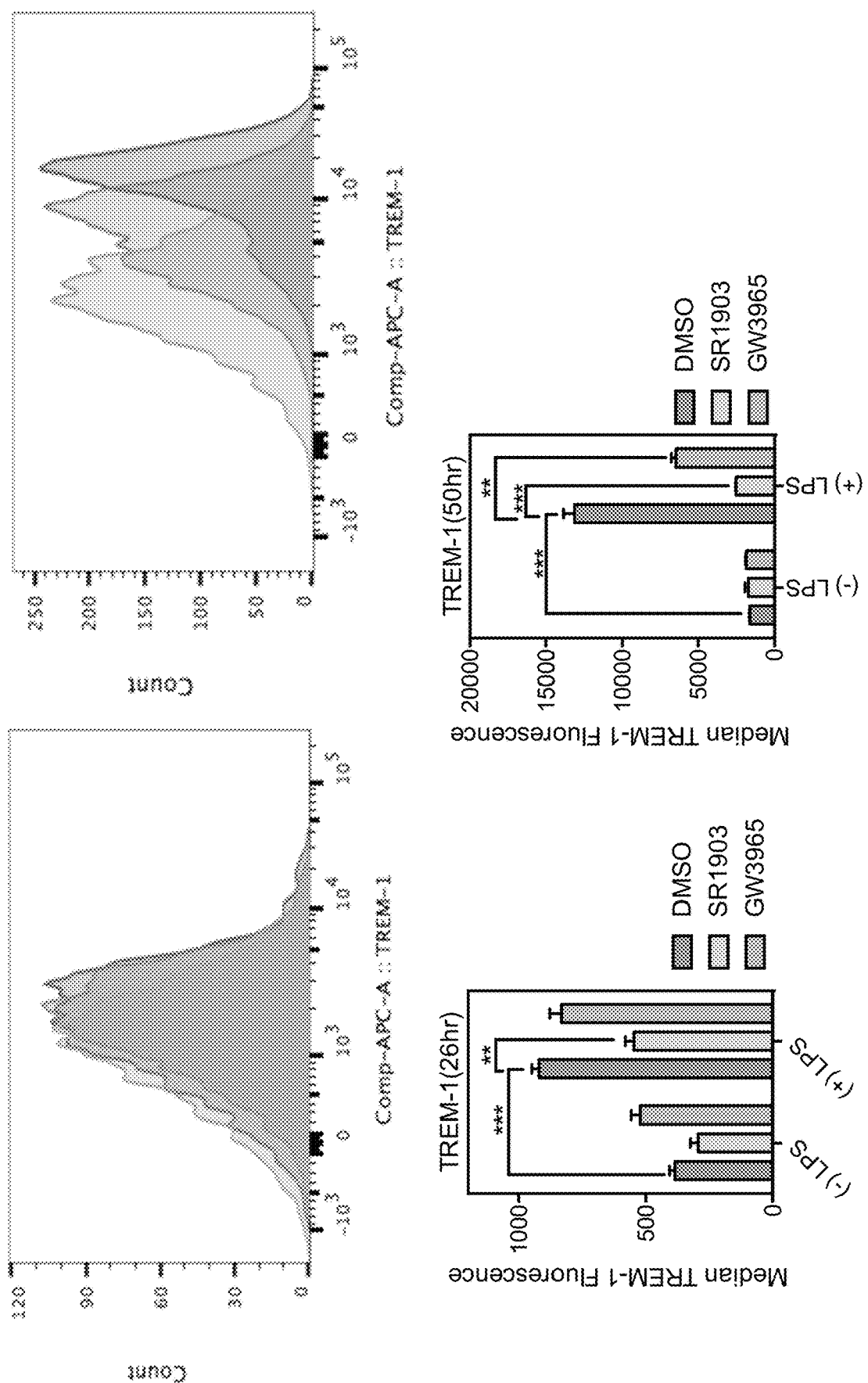

To determine whether LXR agonist treatment impacts TREM1 protein expression, LPS-stimulated RAW264.7 cells were treated with SR1903 or GW3965, or DMSO alone for 26 and 50 hr and following treatment, cells were subjected to FACS analysis to detect TREM1 protein levels. As shown in FIG. 2D there was a slight difference in the level of TREM1 cell surface expression at 26 hr between compound treatment and DMSO only. However, following 50 hr incubation, there was a significant difference between treatments with robust increase in TREM1 protein levels for LPS-only treated cells. While both compounds impacted cell surface expression of TREM1, GW3965 only modestly dampened the LPS-induced increase, yet SR1903 completely blocked the LPS effect.

Figure 3A:
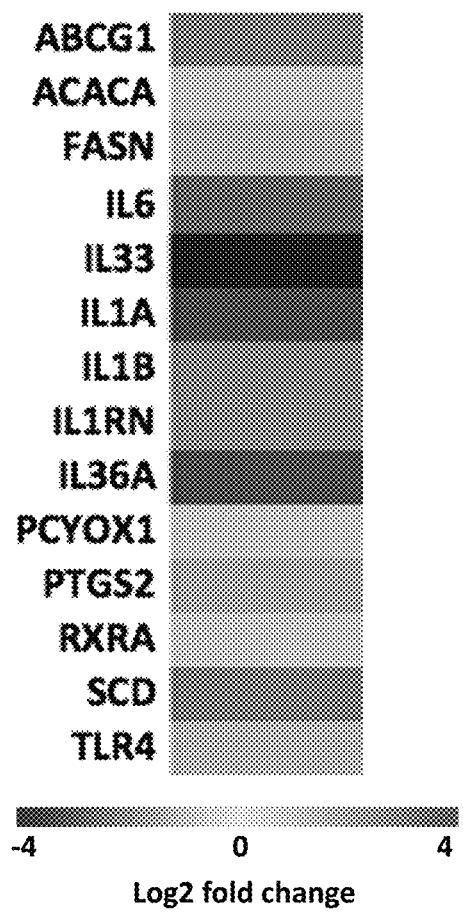
FIGS. 3A-3D: Comparison with LXR agonist.
Figure 3B:
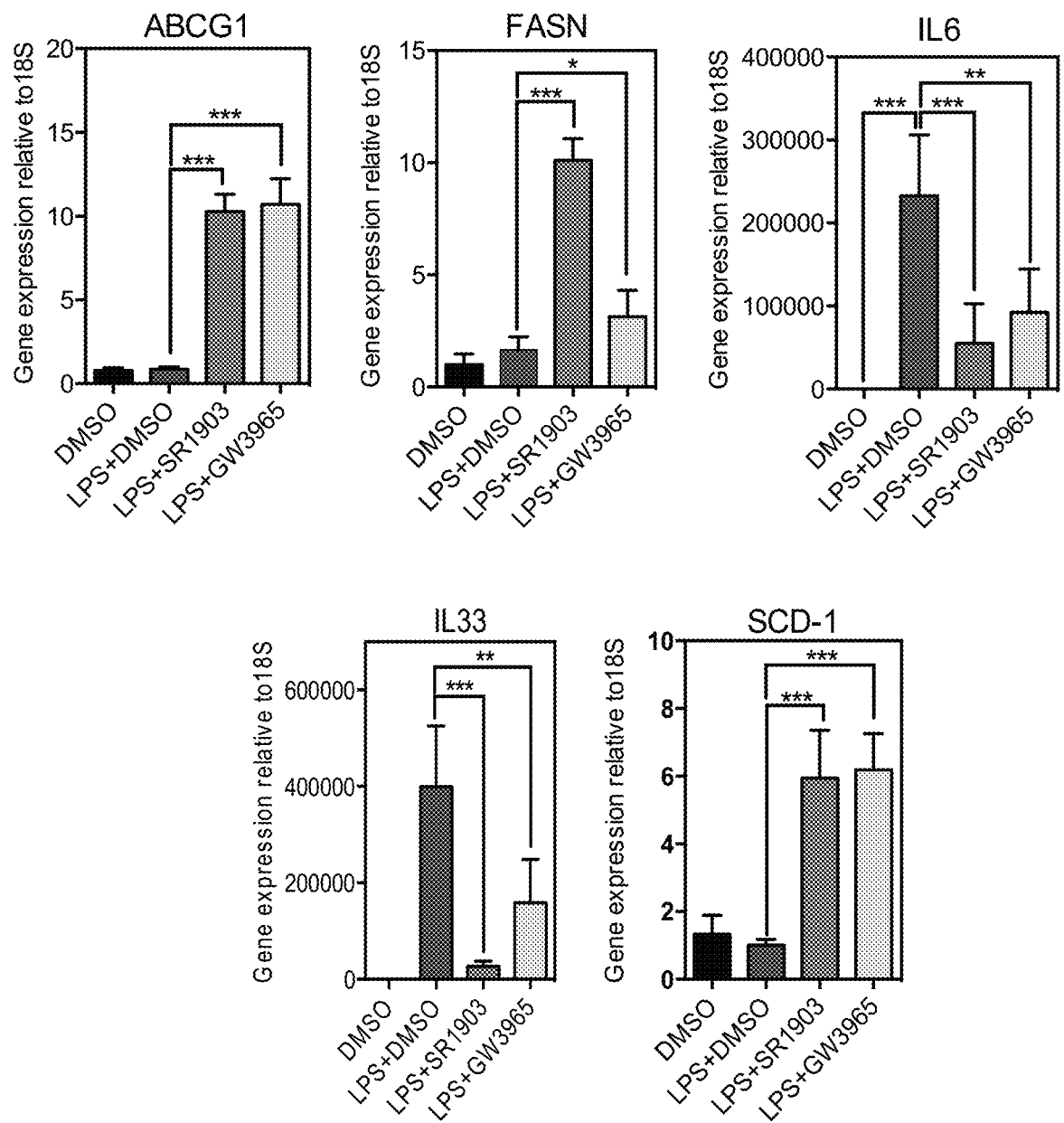

RNA sequencing data was inspected to confirm that SR1903 activates endogenous LXR target genes in LPS-stimulated RAW264.7 cells. As shown in FIG. 3A, treatment of macrophages with SR1903 increased the expression of several LXR target genes including ABCG1 and SCD, proteins involved in cholesterol efflux from macrophages. The expression of ACACA (Acety-CoA Carboxylase I) and FASN (fatty acid synthase I), genes involved in lipid metabolism, were also increased with SR1903. Additionally, the expression of IL6 and IL33, cytokines repressed by LXR activation, were robustly dampened with SR1903 treatment (FIG. 3A). This observation was confirmed using qPCR on LPS-stimulated RAW264.7 cells (FIG. 3B). Enhancement of cholesterol efflux inhibits macrophage foam cell formation which should improve metabolic parameters and suppress inflammatory responses via TLR2, TLR3, and TLR4 by decreasing formation of cholesterol-enriched lipid rafts[25-26].

Figure 3C:
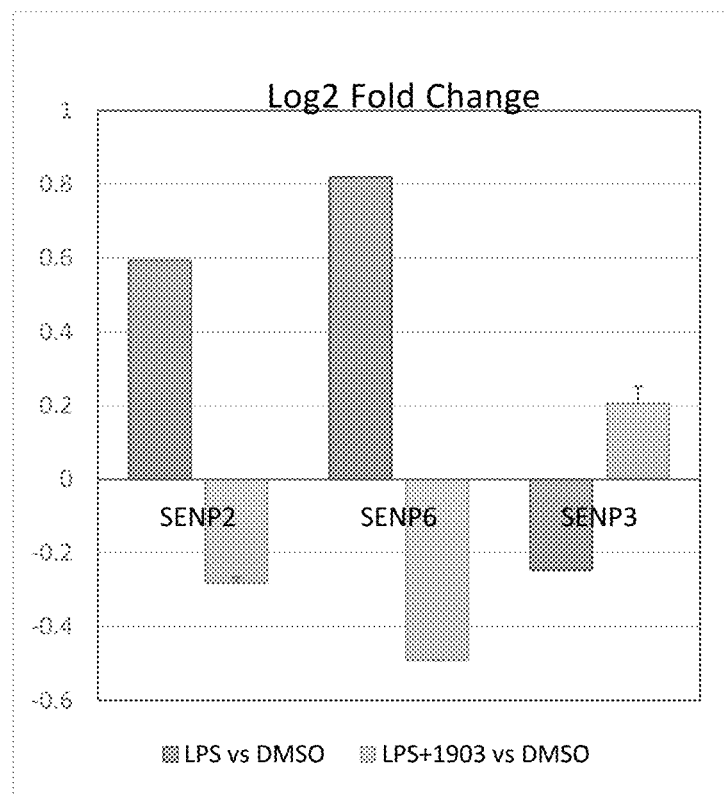
Figure 3D:
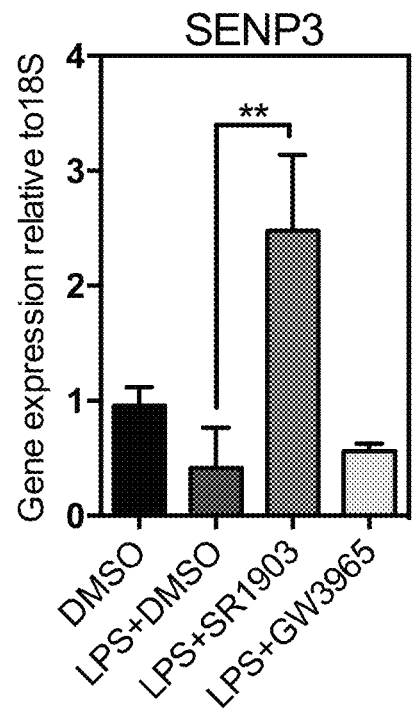

Previously it has been shown that LXR activity is controlled in part by sumoylation[27]. Interestingly, RNA sequencing analysis revealed that treatment of LPS-stimulated RAW cells with SR1903 differentially modulated the expression of various SENP (SUMO specific protease) isoforms (FIG. 3C). Modulation of SENP3 was confirmed by qPCR in similarly treated cells (FIG. 3D). SENP isoforms regulate the SUMOylation status of a wide range of proteins including NRs[28-29]. Via their hydrolase activity, SENPs cleave the pro form of SUMO at its C-terminus to expose two glycine residues which is critical for SUMO to then be conjugated to substrate proteins. Using their isopeptidase activity, SENPs also catalyze de-conjugation of SUMO from modified proteins. This activity is crucial for recycling of SUMO from substrate proteins. Treatment of LPS stimulated RAW cells increased the expression of SENP3 while the expression of SENP2 and SENP6 was repressed. These results indicate that SENP2 and SENP6 are capable of functioning as positive regulators for macrophage activation (pro-inflammatory) whereas SENP3 functions as a negative regulator (anti-inflammatory).

Figure 4A:
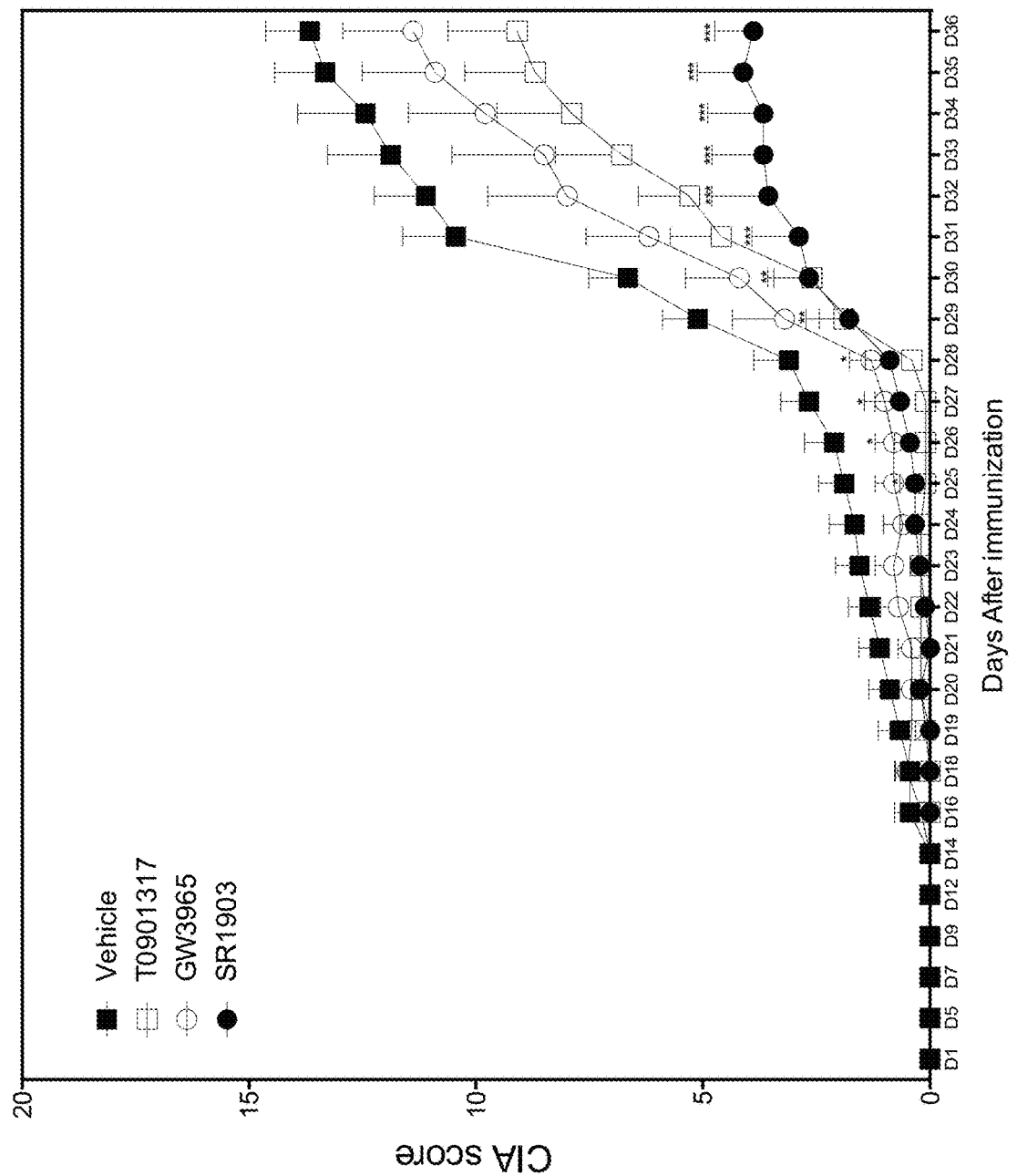
FIGS. 4A-4G: Comparison with LXR agonist and SR1903 on the onset of arthritis in mice with collagen-induced arthritis (CIA) and in vivo efficacy of SR1903 in a mouse model of metabolic disease (DIO) and chronic inflammation.
Figure 8:
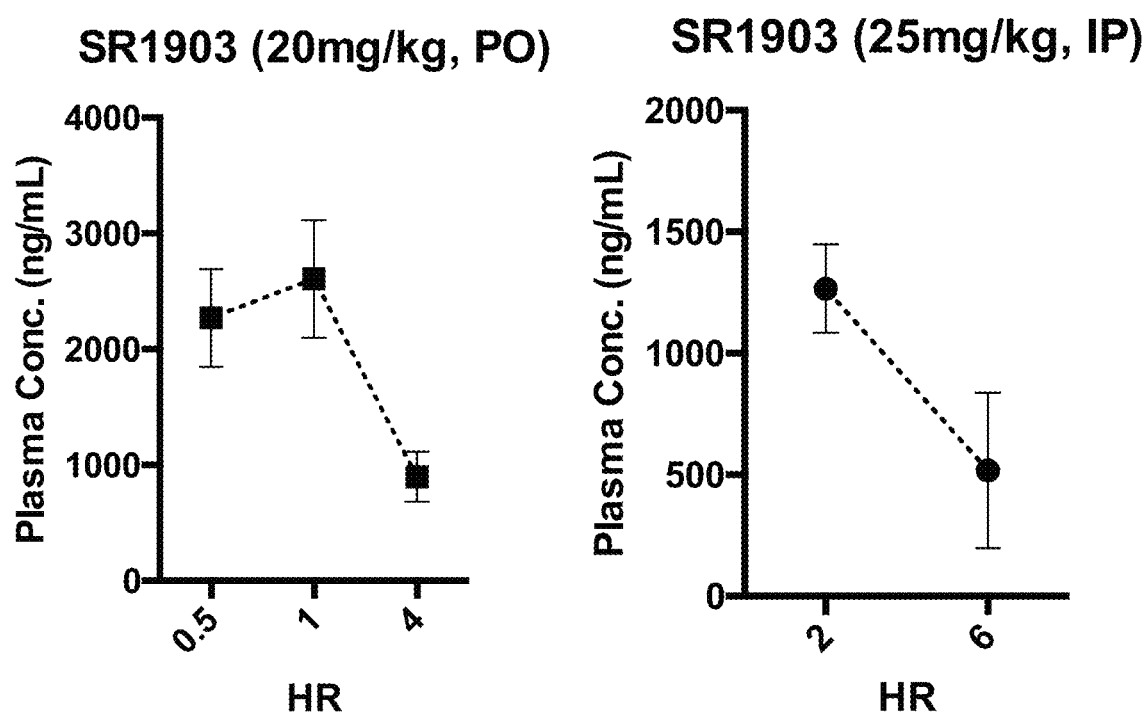
FIG. 8: Pharmacokinetic data for SR1903 in mice. Compound was formulated in 10/10/80 DMSO/Tween80/Water and administered to mice at either 20 mg/kg by oral gavage or at 25 mg/kg via intraperitoneal injection. Blood was drawn at the indicated times and plasma was generated. Following solid phase extraction, drug levels were quantitated using LC-MSMS.
Figures 9A, 9B, 9C, 9D, 9E:
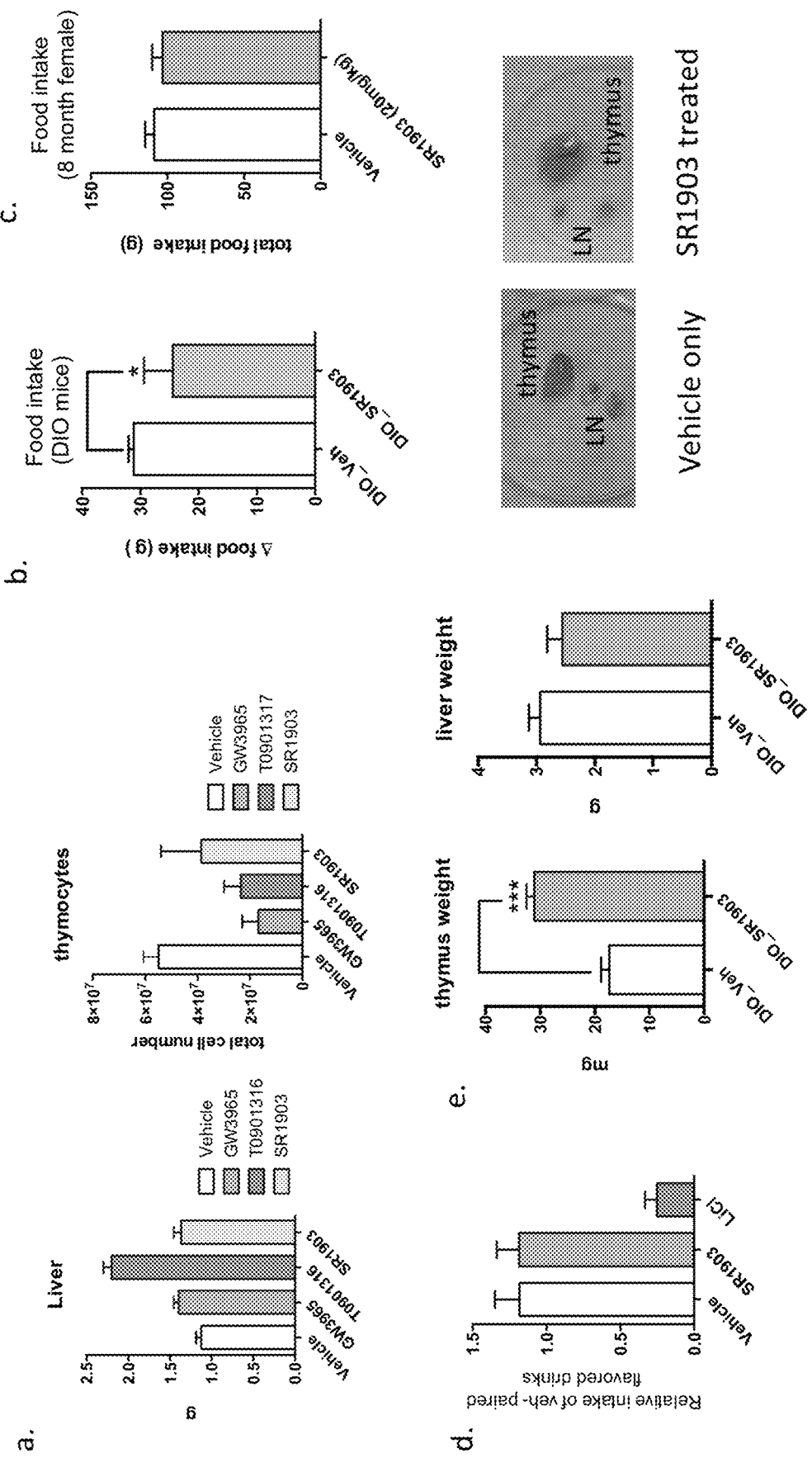
FIG. 9A shows liver weight and total thymocytes number.
FIG. 9B shows total food intake from vehicle and SR1903 treated DIO mice for 14 days.
FIG. 9C shows total food intake from vehicle and SR1903 treated normal chow mice (8-month old female).
FIG. 9D shows the results of conditioned taste aversion (CTA) assay with 20 mg/kg SR1903 and LiCl (0.15M).
FIG. 9E shows thymus and liver weights and picture of thymus and lymph node from vehicle treated DIO mice and SR1903 treated DIO mice.

To investigate if SR1903 possesses similar anti-inflammatory efficacy to that previously observed with SR2211, SR1903 was evaluated in the collagen-induced arthritis mouse model[30]. Given the polypharmacology exhibited by SR1903, CIA mice were also treated with GW3965, a selective LXR agonist and the polypharmacologic modulator T0901317, a modestly potent RORγ inverse agonist with potent LXR agonist activity[31]. Briefly, DBA/1J mice were injected with chicken type II collagen on day 1 and then each animal received a boost injection of collagen on Day 21. Compound treatment, initiated on day 3-post boost injection, was administered intraperitoneally at 20 mg/kg twice-a-day for a total of 16 days. Pharmacokinetic studies revealed that similar plasma exposure for SR1903 at this dose twice-a-day would be sufficient to have compound levels above its $IC_{50}$ (FIG. 8). As shown in FIG. 4A, at the conclusion of the study (Day 34), vehicle-only treated mice had an average clinical score of 13.6±2.9 whereas compound treatment groups all demonstrated a reduction in arthritis clinic score. However, SR1903 was the only treatment that resulted in a statistically significant reduction in clinical score at D34 (avg 3.8±2.5) with only very modest effects observed for the selective LXR agonist GW3965. In contrast to mice treated with T091317, treatment of mice with either SR1903 or GW3965 did not cause enlargement of the liver suggesting the negative effect on liver for T091317 is compound related. Furthermore, CIA mice treated with SR1903 had enhanced thymocyte differentiation and survival compared to mice treated with either the selective LXR agonist GW3965 or the dual LXR agonist/RORγ inverse agonist T0901317 (FIG. 9A). This result was unexpected given that it has been shown previously that either repression of RORγ or agonism of LXR or PPARγ causes T cell apoptosis. These results indicate that a balance of potent RORγ inverse agonism with weak PPARγ repression and modest LXR agonism not only has a robust anti-inflammatory effect with efficacy on improving arthritis symptoms, but also protects against loss of thymocytes.

Figure 4B:
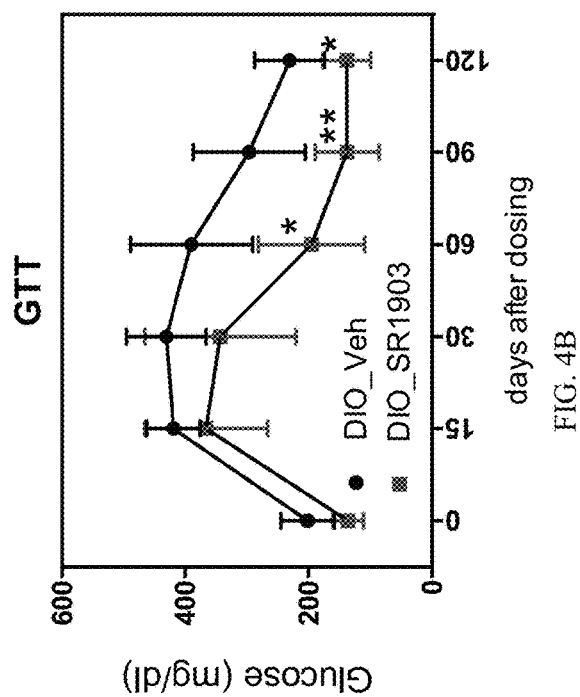
Figure 4C:
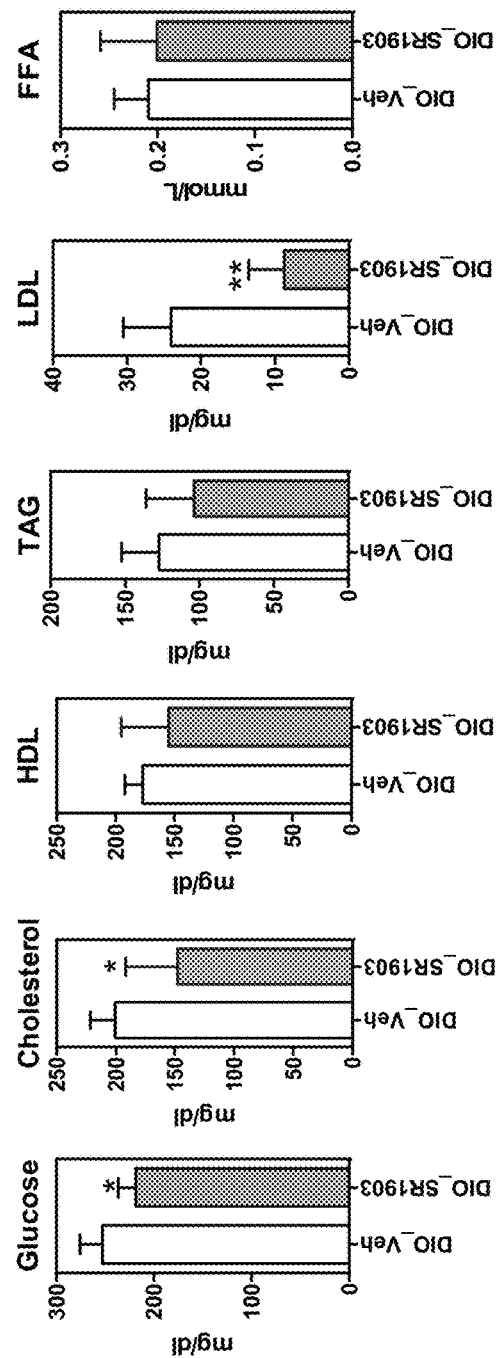

Previous studies with the RORγ inverse agonist SR1555 ($IC_{50}$~1.5 μM) suggested that modulation of this receptor could have beneficial effects on metabolic parameters by induction of fatty acid oxidation in fat pads and improved metabolic parameters (fasting glucose and insulin, cholesterol, triglycerides and free fatty acid levels)[32]. These observations were consistent with effects observed in mice when RORγ expression was genetically impaired[33]. Since SR1903 is significantly more potent as an inverse agonist of RORγ compared to SR1555 and engenders modest agonist activity on LXR and repressive action on PPARγ, the compound was administered to diet-induced obese (DIO) mice to evaluate its impact on metabolic parameters. Briefly, approximately 50 g DIO mice were treated with SR1903 at 20 mg/kg i.p. for 14 days. At the conclusion of the study, a glucose tolerance test was performed and as shown in FIG. 4B there was a statistically significant improvement in glucose excursion. Blood chemistry analysis revealed that SR1903 treatment improved fasting glucose levels and reduced total cholesterol and LDL, whereas no effect was observed on HDL, TAG, and FFA (FIG. 4C).

Figure 4D:
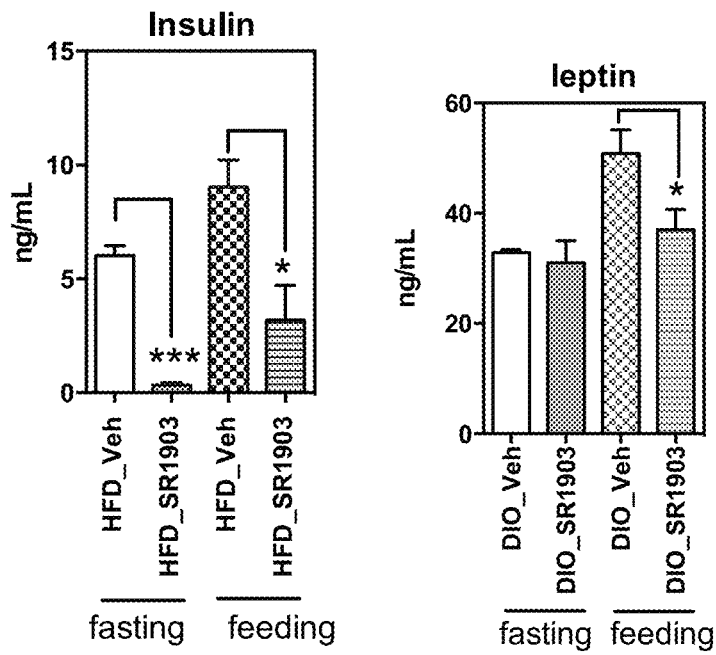
Figure 4E:
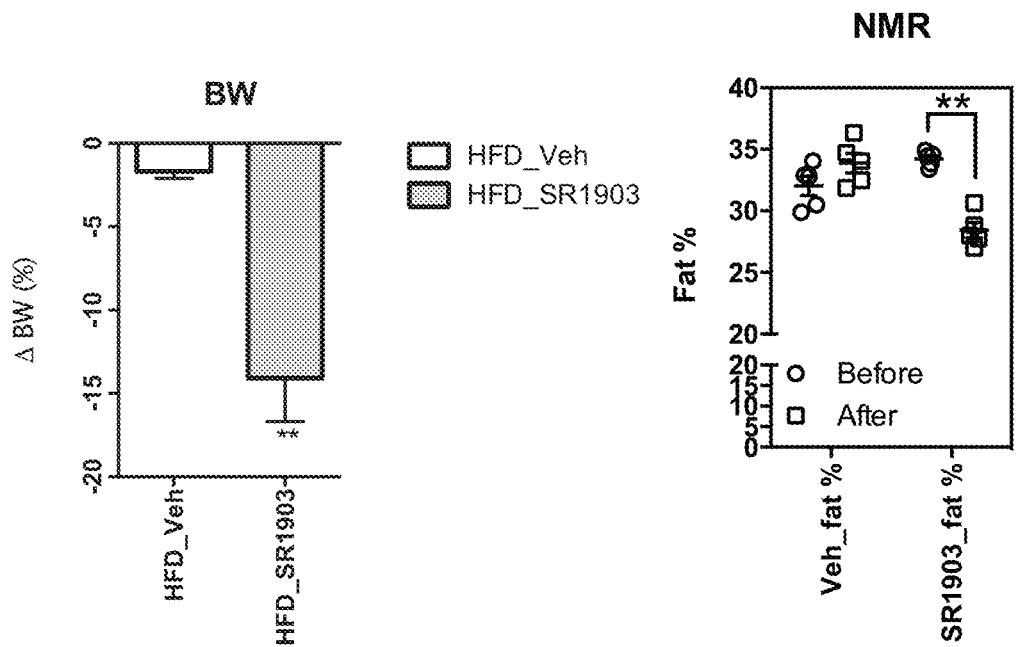
Figure 4F:
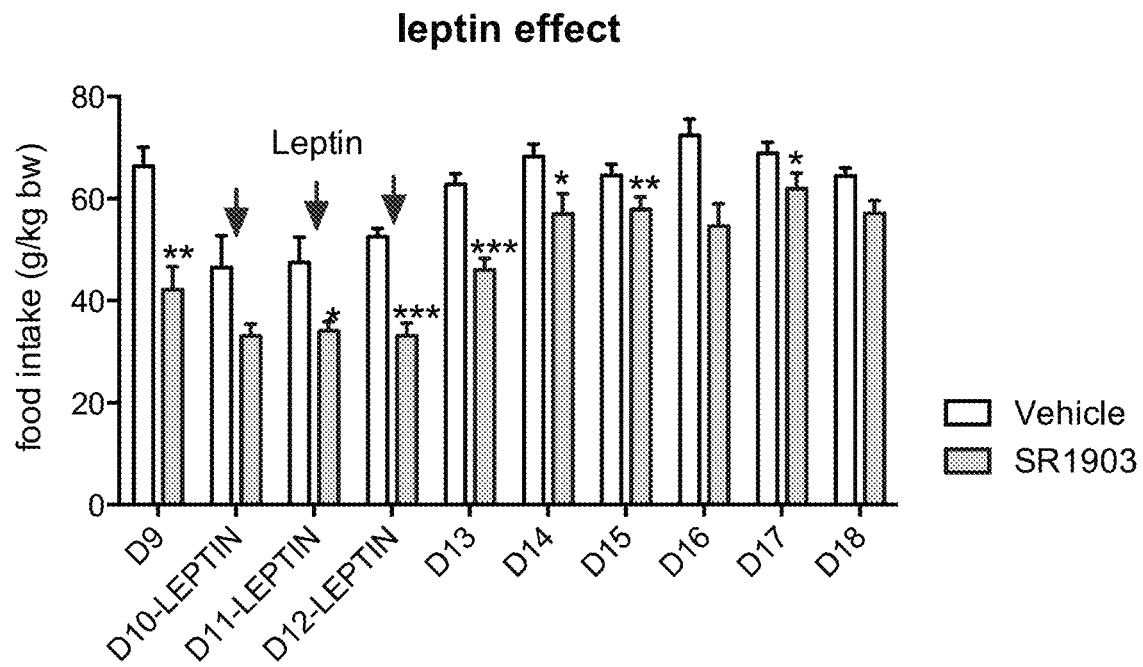
Figure 4G:
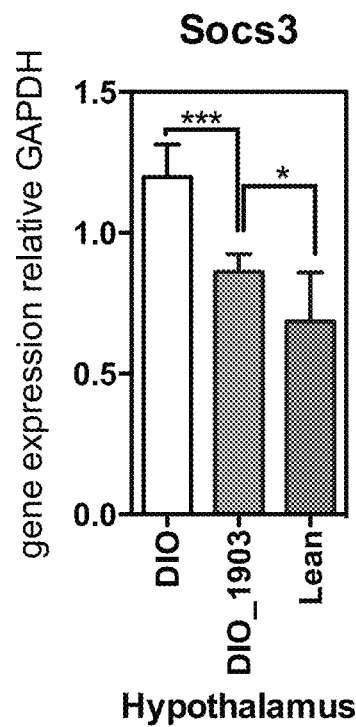

As shown in FIG. 4D, SR1903 treatment improved both fasting and fed insulin levels. While compound treatment did not alter fasting leptin levels, the hormone was statistically reduced when measured in freely feeding mice as compared to vehicle treated animals. Similar to that as shown in Chang et al. 2011[32] for treatment of DIO mice with a selective RORγ inverse agonist SR1555, 14 days of treatment with SR1903 resulted in ~15% body weight reduction accompanied by a ~17% reduction of fat mass as determined by NMR (FIG. 4E). To investigate whether the reduction in body weight in SR1903 treated DIO mice compared with vehicle treated DIO mice could be attributed to difference in caloric intake, we measured food intake (FIG. 9B). While SR1903 reduced food intake in DIO mice, treatment with compound in lean mice had no effect on food intake (FIG. 9C) ruling out a general toxic effect of the compound. More importantly, SR1903 had no effect on mice treated with compound when evaluated in a conditioned taste aversion paradigm[34] (FIG. 9D). In an effect to better understand the impact of the compound on caloric intake, DIO mice treated with SR1903 were subjected to a leptin sensitivity test. Leptin resistance in DIO mice was reduced by SR1903 treatment as shown in FIG. 4F. Consistent with this observation Socs3 (suppressor of cytokine signaling-3) expression was repressed in the hypothalamus of DIO mice following SR1903 treatment (FIG. 4G). Hypothalamic Socs3 has been shown to be a negative regulator of leptin receptor signaling[35].

Figure 9F:
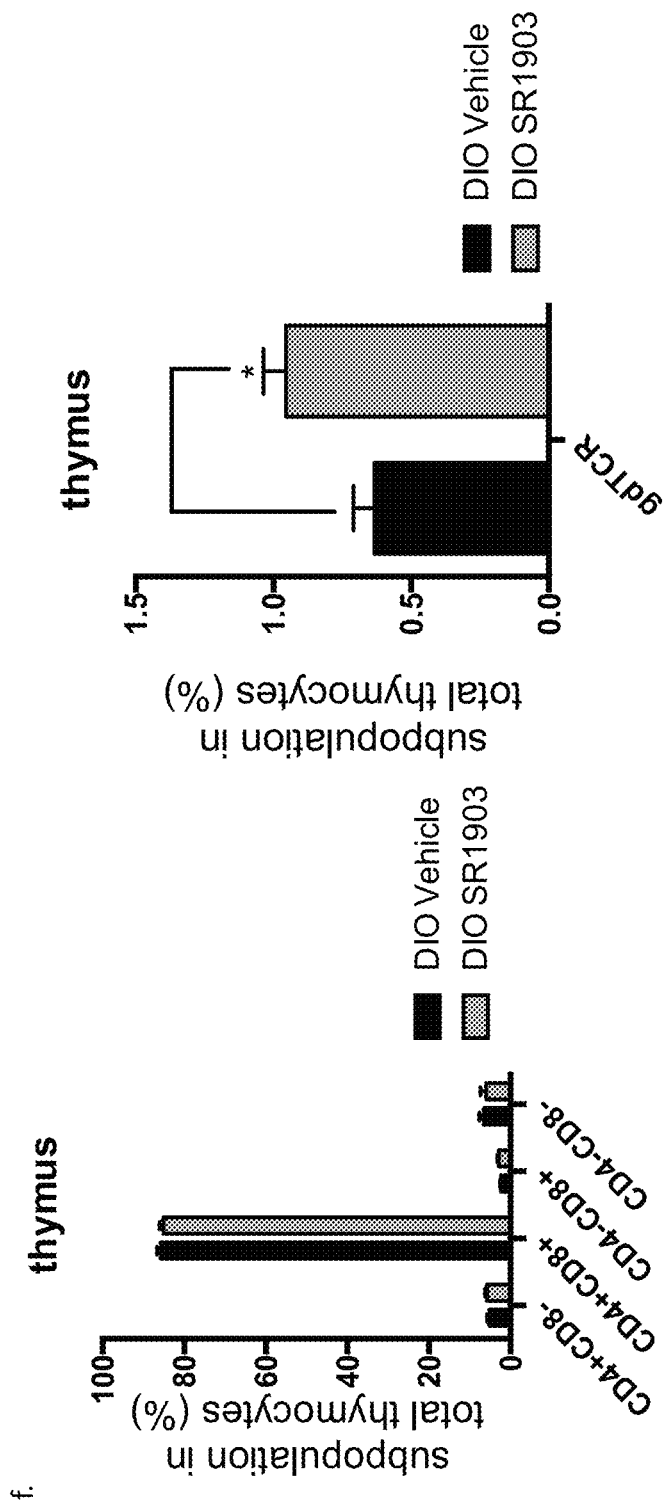
FIG. 9F shows the percentage of αβT cell subpopulations and γδT cells in thymocytes.

In mice, the involution of thymus is detectable within one year of age[36] and the rate of involution is accelerated in obesity[37]. To investigate whether the anti-obesity effect of SR1903 in mice impacts thymic involution, thymi from 22-week-old DIO mice treated for 14 days with SR1903 (20 mg/kg) or vehicle only were analyzed. SR1903 treated DIO mice were protected from obesity related thymic involution as indicated by an increase in thymus weight and preservation of thymocytes (FIG. 9E). As shown in FIG. 9F, comparison of T cells from SR1903 treated and vehicle treated DIO mice demonstrated the compound had no effect on differentiation of αβTCR⁺CD4⁺ and αβTCR⁺CD8⁺ cells; whereas there was an increase in λδT cell differentiation.

Figure 5A:
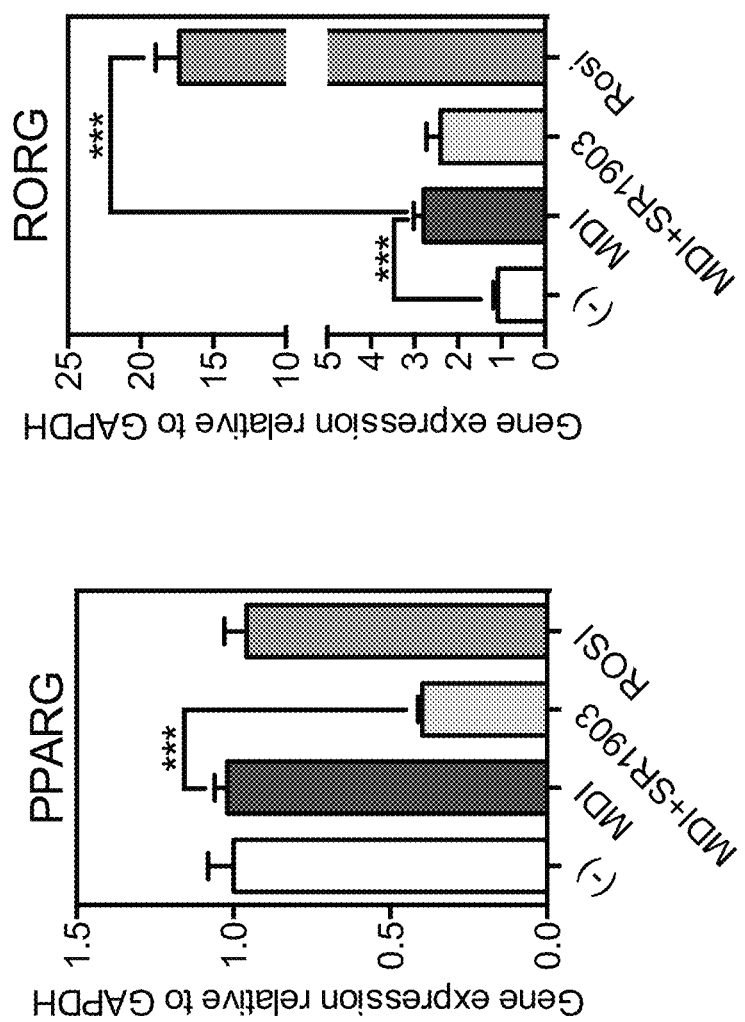
FIG. 5A-5C: PPARγ and RORγ expression during adipogenesis of OP9 cells.
Figure 5B:
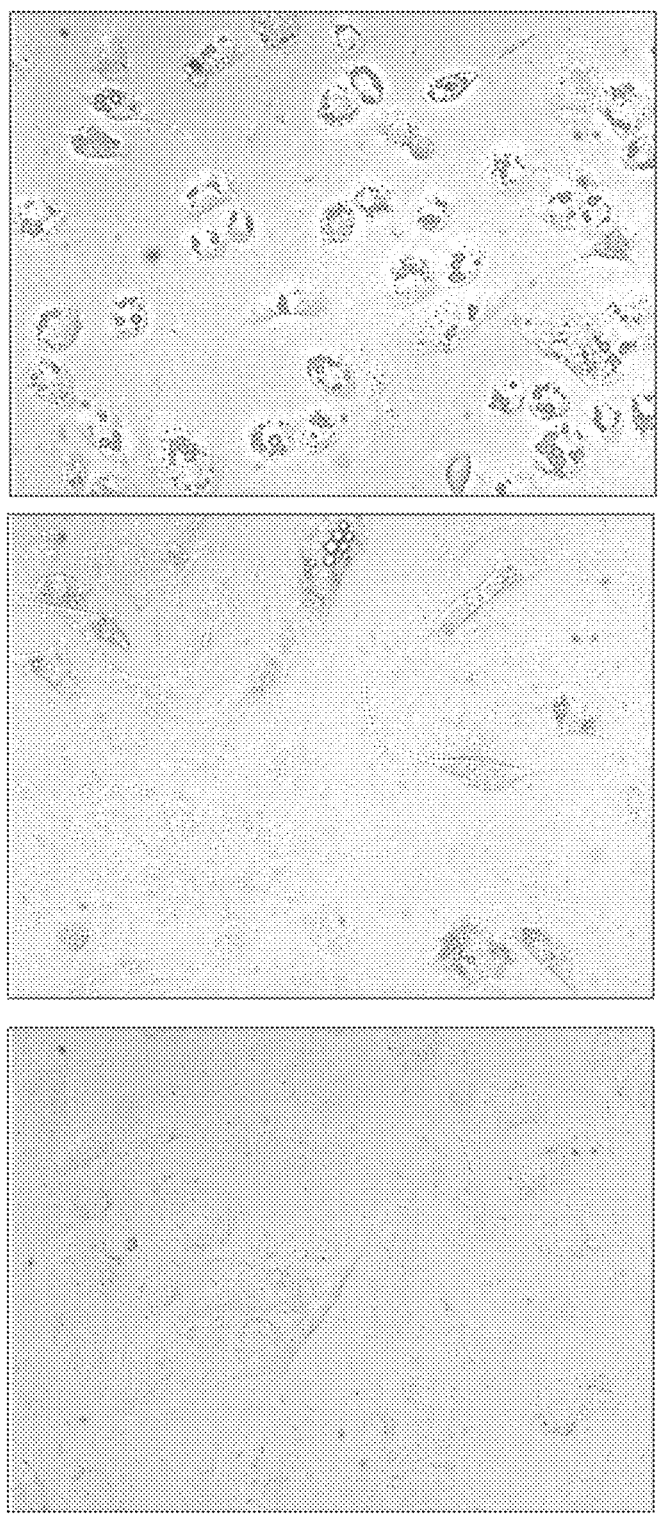
Figure 5C:
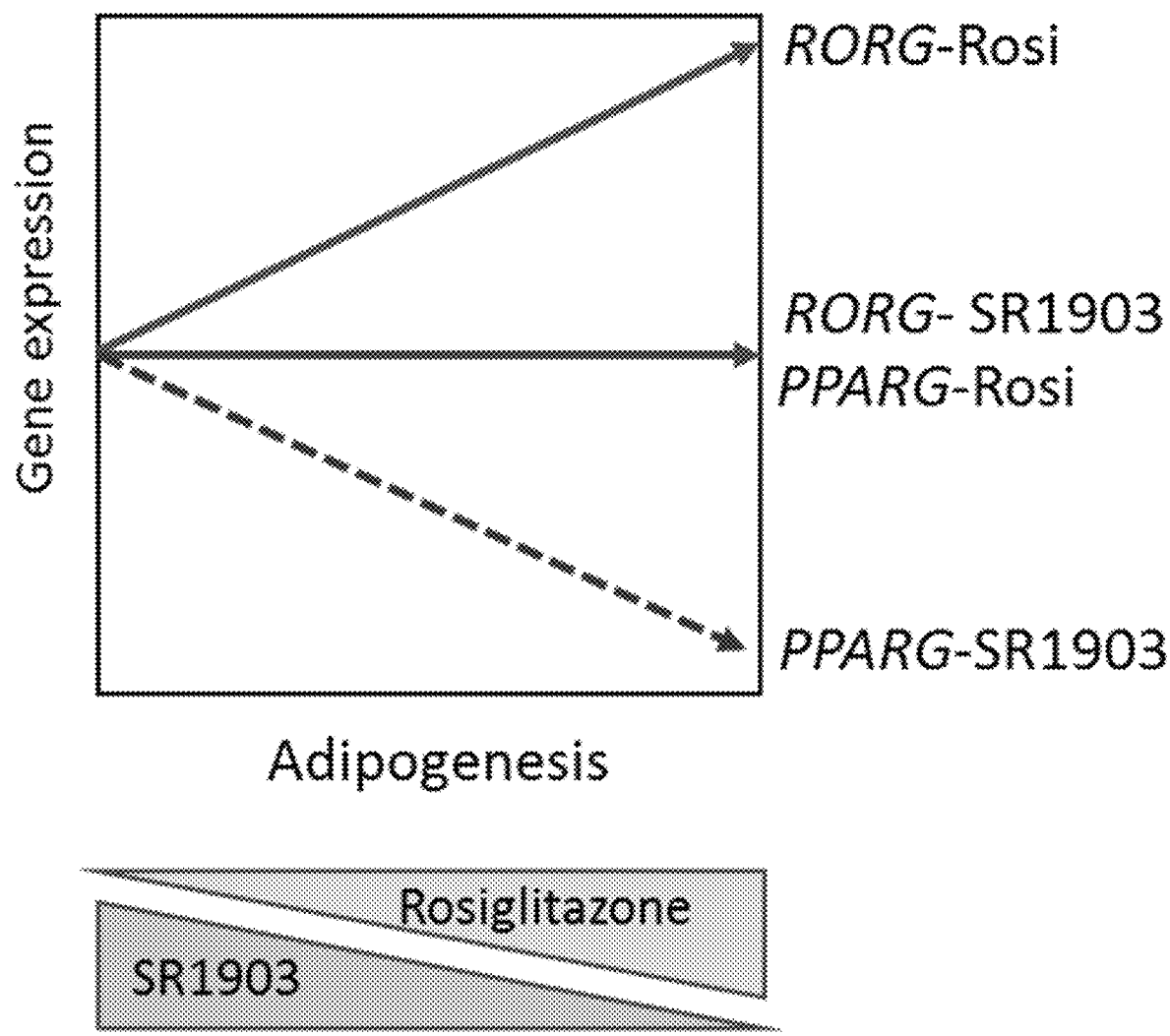

Having observed that SR1903 can repress adipogenic genes, and treatment of obese mice with the compound leads to a reduction in body weight almost exclusively as loss of fat, the relationship of PPARγ and RORγ was investigated during adipogenesis. Thus, bone marrow derived OP9 cells were differentiated towards adipocytes using MDI alone or MDI in combination with SR1903 and rosiglitazone alone as a positive control. Following compound treatment for 3 days, lipid droplet formation was observed. As shown in FIG. 5B, SR1903 showed suppression of lipid droplet formation. While rosiglitazone treatment did not alter the expression levels of PPARγ, it did robustly upregulate the expression of RORγ (FIG. 5A), in contrast to SR1903 treatment. SR1903 had no effect on the expression level of RORγ but treatment with this compound robustly repressed the expression of PPARγ. As summarized in FIG. 5C, these data indicate that these two receptors play opposing roles in adipogenesis.

Nuclear receptors function as ligand-modulated transcription factors controlling gene expression programs involved in numerous biological processes. The activity of NRs can be increased or decreased by administration of exogenous natural or synthetic ligands making them attractive drug targets for treatment of a wide range of diseases[1]. However, pleiotropic effects have limited the clinical utility of several approved NR modulators and ended clinical development of many more. This fact has spurred interest in developing functional selective NR modulators (also referred to as dissociated modulators), where the goal is to design ligands that modulate (activate or repress) a specific sub-set of disease-related genes. RORγ inverse agonists are currently under clinical development for treatment of various auto-immune diseases[38]. LXR agonists have been in clinical development for treatment of dyslipidemia and inflammatory diseases[39]. While PPARγ agonists and partial agonists have been approved and have been in clinical development for metabolic disease, inverse agonists of this receptor conceptually hold promise for a wide range of diseases including osteoporosis and cancer[14]. In this context, the present disclosure relates to methods and uses of the polypharmacological modulator SR1903 which functions as a potent RORγ inverse agonist with modest agonist activity on LXR and mild repression (inverse agonism) of PPARγ in a range of biophysical and cellular models.

Given the unique polypharmacology of SR1903, efficacy studies were warranted. Results presented demonstrate the anti-inflammatory and anti-diabetic properties of SR1903 in the collagen induced arthritis (CIA) and diet-induced obesity (DIO) mouse models, respectively. As expected, SR1903 afforded similar efficacy to that observed for SR2211 in the CIA model in terms of improvement in clinical scores[1]. However, unlike that observed in SR2211 treated mice[40], intrathymic cell number was enriched in SR1903 treated mice and secondary lymphoid organs such as lymph node and spleen had similar cell number to that of the vehicle-only control mice. Treatment of DIO mice with SR1903 resulted in reduction in fat mass resulting in reduced body weight and improvements in both insulin and leptin sensitivity. While food intake was reduced in the context of DIO, the compound had no impact on food consumption and body weight when administered to lean mice, and SR1903 had a null effect in a conditioned taste aversion behavioral paradigm.

Treatment of macrophages with SR1903 resulted in nearly complete blockade of activation of TREM-1 expression and cell surface protein whereas treatment with the selective LRX agonist GW3965 only had modest impact on TREM-1 expression and little effect on cell surface protein levels. Because excessive inflammation can lead to tissue and organ damage, these data position SR1903 a useful therapeutic for innate immune disorders.

Nuclear receptors function as ligand-modulated transcription factors controlling gene expression programs involved in numerous biological processes. The activity of NRs can be increased or decreased by administration of exogenous natural or synthetic ligands making them attractive drug targets for treatment of a wide range of diseases[1]. However, pleiotropic effects have limited the clinical utility of several approved NR modulators and ended clinical development of many more. This fact has spurred interest in developing functional selective NR modulators (also referred to as dissociated modulators), where the goal is to design ligands that modulate (activate or repress) a specific sub-set of disease-related genes. RORγ inverse agonists are currently under clinical development for treatment of various auto-immune diseases[38]. LXR agonists have been in clinical development for treatment of dyslipidemia and inflammatory diseases[39]. While PPARγ agonists and partial agonists have been approved and have been in clinical development for metabolic disease, inverse agonists of this receptor conceptually hold promise for a wide range of diseases including osteoporosis and cancer[14]. In this context, the present disclosure relates to methods and uses of the polypharmacological modulator SR1903 which functions as a potent RORγ inverse agonist with modest agonist activity on LXR and mild repression (inverse agonism) of PPARγ in a range of biophysical and cellular models.

Given the unique polypharmacology of SR1903, efficacy studies were warranted. Results presented demonstrate the anti-inflammatory and anti-diabetic properties of SR1903 in the collagen induced arthritis (CIA) and diet-induced obesity (DIO) mouse models, respectively. As expected, SR1903 afforded similar efficacy to that observed for SR2211 in the CIA model in terms of improvement in clinical scores[1]. However, unlike that observed in SR2211 treated mice[40], intrathymic cell number was enriched in SR1903 treated mice and secondary lymphoid organs such as lymph node and spleen had similar cell number to that of the vehicle-only control mice. Treatment of DIO mice with SR1903 resulted in reduction in fat mass resulting in reduced body weight and improvements in both insulin and leptin sensitivity. While food intake was reduced in the context of DIO, the compound had no impact on food consumption and body weight when administered to lean mice, and SR1903 had a null effect in a conditioned taste aversion behavioral paradigm.

Treatment of macrophages with SR1903 resulted in nearly complete blockade of activation of TREM-1 expression and cell surface protein whereas treatment with the selective LRX agonist GW3965 only had modest impact on TREM-1 expression and little effect on cell surface protein levels. Because excessive inflammation can lead to tissue and organ damage, these data position SR1903 a useful therapeutic for innate immune disorders, for example.

Example 2: Synthesis of SR1903 (1,1,1,3,3,3-hexafluoro-2-(2'-methyl-4'-((4-(pyridin-4-ylmethyl)piperazin-1-yl)methyl)-[1,1'-biphenyl]-4-yl)propan-2-ol)

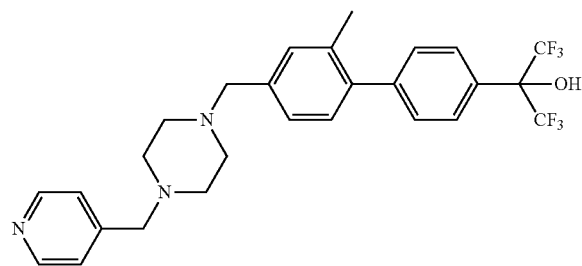 [SMILES: Cc1cc(CN2CCN(Cc3ccncc3)CC2)ccc1-c1ccc(C(O)(C(F)(F)F)C(F)(F)F)cc1]

Step 1: 4'-(1,1,1,3,3,3-hexafluoro-2-hydroxypropan-2-yl)-2-methyl-[1,1'-biphenyl]-4-carbaldehyde

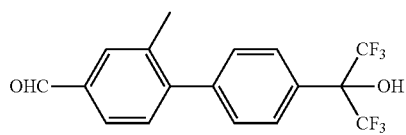 [SMILES: Cc1cc(C=O)ccc1-c1ccc(C(O)(C(F)(F)F)C(F)(F)F)cc1]

A mixture of 1,1,1,3,3,3-hexafluoro-2-(4-iodophenyl)propan-2-ol (1.0 g, 2.7 mmol), (4-formyl-2-methylphenyl)boronic acid (0.52 g, 3.2 mmol), Pd(PPh$_3$)$_4$ (0.31 g, 0.27 mmol), K$_2$CO$_3$ (1.1 g, 8.1 mmol) and dioxane/H$_2$O (4:1, 15 mL) was degassed for 5 min and then heated for 2 h in an 80° C. oil bath. Reaction progress was monitored by reverse-phase analytical HPLC for disappearance of starting materials. When judged complete, the mixture was cooled to rt and diluted with EtOAc and H$_2$O. The layers were separated, and the aqueous layer was extracted with EtOAc (2×). The combined organic layers were washed with saturated NaHCO$_3$, brine (Na$_2$SO$_4$) and concentrated in vacuo. The crude residue was purified by flash chromatography on silica gel (EtOAc/hexanes) to obtain the title compound as a colorless solid.

$^1$H NMR (400 MHz, CDCl$_3$) δ 10.03 (s, 1H), 7.83-7.76 (m, 4H), 7.45-7.40 (m, 3H), 3.91 (br, 1H), 2.36 (s, 3H); $^{13}$C NMR (100 MHz, CDCl$_3$) δ 192.4, 146.9, 142.6, 136.5, 135.6, 131.7, 130.5, 129.1, 128.8, 127.5, 126.6, 124.1, 121.2, 20.4.

Step 2: 1,1,1,3,3,3-hexafluoro-2-(2'-methyl-4'-((4-(pyridin-4-ylmethyl)piperazin-1-yl)methyl)-[1,1'-biphenyl]-4-yl)propan-2-ol A solution of 4'-(1,1,1,3,3,3-hexafluoro-2-hydroxypropan-2-yl)-2-methyl-[1,1'-biphenyl]-4-carbaldehyde (1 eq) and commercially available 1-(pyridin-4-ylmethyl)piperazine (1.1 eq) were stirred for 30 minutes in dry DMF (0.5 mL) at rt. NaBH(OAc)$_3$ (2 eq) was added and the resulting mixture was stirred at rt overnight. The completion of reaction was monitored by analytical HPLC and LC/MS. The reaction was quenched with MeOH. The mixture was purified by prep-HPLC (MeOH/Acetonitrile/water) to obtain the title compound as a TFA salt. Compound 1 was judged to be >95% pure by reverse-phase analytical HPLC.

ESI-MS (m/z): 524 [M+H]; $^1$H NMR (400 MHz, d6-DMSO) δ 8.82 (s, 1H), 8.53 (d, 2H, J=4.0 Hz), 7.77 (d, 2H, J=8.0 Hz), 7.53 (d, 2H, J=8.0 Hz), 7.35 (d, 2H, J=4.0 Hz), 7.26 (s, 1H), 7.22 (s, 2H), 3.54 (s, 2H), 3.50 (s, 2H), 2.45 (broad s, 8H), 2.26 (s, 3H); $^{13}$C NMR (100 MHz, d6-DMSO) 149.48 (2C), 147.45 (2C), 142.86, 138.66, 137.74, 134.41 (2C), 130.85, 129.37, 129.20 (2C), 129.15 (2C), 126.61(2C), 126.50, 123.66 (2C), 61.70, 60.61, 52.66 (2C), 52.61 (2C), 20.12.

Materials and Methods

Chemicals: SR1903

Cell lines: HEK293T cells and EL4 cells (American Type Culture Collection) were maintained in DMEM and RAW264.7 cells (American Type Culture Collection) were maintained in RPMI-1640 with 10% heat inactivated FBS and antibiotics (penicillin, streptomycin; Invitrogen). OP9 cells (American Type Culture collection) were maintained in Alpha minimum essential medium (MEM-alpha) with 20% heat inactivated FBS. Twenty-four hours post-confluence, the OP9 cells were differentiated with IBMX (0.5 nM), dexamethasone (1 μM), Insulin (10 μg/mL) for 48 hrs.

Reporter gene assays: Twenty-four hours before transfection, HEK293T cells were plated in 96-well plates at a density of 15×10$^3$ cells per well. UAS:luciferase reporter and Gal4-RORa, Gal4-RORb, Gal4-RORγ, Gal4-LXRα, or Gal4 PPARγ DNA co-transfections were performed using X-tremeGENE 9 (Roche). Twenty-four hours after transfection, the cells were treated with vehicle or compound. Twenty-four hours after treatment, the luciferase activity was measured using the Dual-Glo luciferase assay system (Promega). Results were analyzed using GraphPad Prism software.

TREM1 promoter cloning and reporter assay: TREM1 promoter region (79555-76200 Mus musculus BAC clone CH25-69K1 from chromosome 17, Sequence ID: AC241601.3) was PCR amplified from genomic DNA (pancreatic tissue) and sub-cloned into pGL3-Basic vector with KpnI/XhoI restriction sites. The 3,356 bp region of mTREM1 promoter was verified by DNA sequencing. Each LXRβ, PPARγ, and RORγ full length plasmid was co-transfected with TREM1/pGL3 using X-tremeGENE 9 into HEK293T cells. After 48 hrs, luciferase activity was measured using BriteLite plus assay system (PerkinElmer).

LanthaScreen: PPARγ competitive-binding assay (Invitrogen) was performed according to the manufacturer's protocol. A mixture of 5 nM glutathione S-transferase fused with the PPARγ ligand-binding domain (GST-PPARγ-LBD), 5 nM Tb-GST-antibody, 5 nM Fluormone Pan-PPAR Green and serial dilutions of compound beginning at 10 μM downwards was added to wells of black 384-well low-volume plates (Greiner) to a total volume of 18 μl. All dilutions were made in Time-resolved (TR)-fluorescence resonance energy transfer (FRET) PPAR assay buffer. DMSO at 2% final concentration was used as a no-ligand control. Experiments were performed in triplicate and incubated for 2 h in the dark before analysis in Perkin Elmer ViewLux ultra HTS microplate reader. The FRET signal was measured by excitation at 340 nm and emission at 520 nm for fluorescein and 490 nm for terbium. The fold change over DMSO was calculated by 520 nm/490 nm ratio. Graphs were plotted in GraphPad Prism as fold change of FRET signal for each compound over DMSO-only control and effector concentration for half-maximum response calculated.

NR box peptide recruitment assay. Tb-anti-His antibody (10 nM; Invitrogen) and indicated ligand (1 uM) were incubated in complete TR-FRET PPAR assay buffer (Invitrogen) containing 10 nM purified His-PPARγ2 for 1 hr at room temperature. 450 nM FITC-labeled peptides p300 (sequence: ASKHKQLSELLRSGSS was added and incubated for additional two hrs at room temperature (in dark). The FRET signal was measured by excitation at 340 nm and emission at 520 nm for fluorescein and 490 nm for terbium in Perkin Elmer ViewLux ultra HTS microplate reader. The fold change over DMSO was calculated by 520 nm/490 nm ratio. Each sample condition has four replicates.

Quantitative RT-PCR: Total RNA was extracted from EL4 or RAW264.7 cells using RNeasy Plus Micro Kit (Qiagen) and the RNA was reverse transcribed using the ABI reverse transcription kit (Applied Biosystems/Thermo Fisher Scientific, Waltham MA). Quantitative PCR was performed with a 7900HT Fast Real Time PCR System (Applied Biosystems) using SYBR green (Roche). A list of primers used for these studies is shown in the table below.

TABLE

| Primer sequences. | |
|---|---|
| Gene name | Primer sequence (5'-3') |
| 18S (F) | GTAACCCGTTGAACCCCATT (SEQ ID NO: 2) |
| 18S (R) | CCATCCAATCGGTAGTAGCCG (SEQ ID NO: 3) |
| ABCG1 (F) | TTC ATC GTC CTG GGC ATC TT (SEQ ID NO: 4) |

TABLE-continued

Primer sequences.

| Gene name | Primer sequence (5'-3') |
|---|---|
| ABCG1 (R) | CGG ATT TTG TAT CTG AGG ACG AA (SEQ ID NO: 5) |
| FASN (F) | GCT GGC ATT CGT GAT GGA GTC GT (SEQ ID NO: 6) |
| FASN (R) | AGG CCA CCA GTG ATG ATG TAA CTC T (SEQ ID NO: 7) |
| GAPDH (F) | ACC CAG AAG ACT GTG GAT GG (SEQ ID NO: 8) |
| GAPDH (R) | ACA CAT TGG GGG TAG GAA CA (SEQ ID NO: 9) |
| IL-33 (F) | TGA GAC TCC GTT CTG GCC TC (SEQ ID NO: 10) |
| IL-33 (R) | CTC TTC ATG CTT GGT ACC CGA T (SEQ ID NO: 11) |
| IL-6 (F) | CCATCAGGGCTGGAAAGGTT (SEQ ID NO: 12) |
| IL-6 (R) | GGGCAGGCAGTAATCCCTTT (SEQ ID NO: 13) |
| PPARG2 (F) | CTC TGT TTT ATG CTG TTA TGG GTG A (SEQ ID NO: 14) |
| PPARG2 (R) | GGT CAA CAG GAG AAT CTC CCA G (SEQ ID NO: 15) |
| RORG (F) | ACC TCC ACT GCC AGC TGT GTG CTG TC (SEQ ID NO: 16) |
| RORG (R) | TCA TTT CTG CAC TTC TGC ATG TAG ACT GTC CC (SEQ ID NO: 17) |
| SCD-1 (R) | CCG GAG ACC CCT TAG ATC GA (SEQ ID NO: 25) |
| SCD-1 (F) | TAG CCT GTA AAA GAT TTC TGC AAA CC (SEQ ID NO: 18) |
| SENP3 (F) | TGACTTGGGCATTGCAGA (SEQ ID NO: 19) |
| SENP3 (R) | CTGACGACGGAGTTTGGG (SEQ ID NO: 20) |
| SOCS3 (F) | GCTCCAAAAGCGAGTACCAGC (SEQ ID NO: 21) |
| SOCS3 (R) | AGTAGAATCCGCTCTCCTGCAG (SEQ ID NO: 22) |
| TREM1 (F) | CGG AAT TCG AGC TTG AAG GAT GAG GAA GGC (SEQ ID NO: 23) |
| TREM1 (R) | AAT CCA GAG TCT GTC ACT TGA AGO TCA GTC (SEQ ID NO: 24) | mRNA sequencing analysis: RAW264.7 cells RNA extraction protocol for RNA seq was derived from Qiagen Kit-74106. Total RNA was quantified using the Qubit 2.0 Fluorometer (Invitrogen, Carlsbad, CA) and run on the Agilent 2100 Bioanalyzer (Agilent Technologies, Santa Clara, CA) for quality assessment. RNA samples of good quality with RNA Integrity Number (RIN)>8.0 were further processed. A RNase-free working environment was maintained and RNase-free tips, Eppendorf tubes and plates were utilized for the subsequent steps. Messenger RNA was selectively isolated from total RNA (300 ng input) using poly-T oligos attached to magnetic beads and converted to sequence-ready libraries using the TruSeq stranded mRNA sample prep protocol (Cat. #: RS-122-2101, Illumina, San Diego, CA). The final libraries were validated on the bioanalyzer DNA chips and qPCR quantified using primers that recognize the illumina adaptors. The libraries were then pooled at equimolar ratios, quantified using qPCR and loaded onto the NextSeq 500 flow cell at 1.8 pM final concentration. They were sequenced using the high-output, paired-end, 75-bp chemistry. Demultiplexed and quality filtered raw reads (fastq) generated from the NextSeq 500 were trimmed (adaptor sequences) using Flexbar 2.4 and aligned to the mouse reference database (mm9) using TopHat version 2.0.9 (Trapnell et al., 2009). HTseq-count version 0.6.1 was used to generate gene counts and differential gene expression analysis was performed using Deseq2 (Anders and Huber, 2010). We then identified genes that were significantly down-regulated or up-regulated (adjusted $P<0.05$) in each comparison.

Mice: All mice were maintained in a specific pathogen-free environment in accordance with institutional protocol. All procedures were reviewed and approved by The Scripps Research Institute animal care and use committee. Male DIO mice, 22 weeks of age, were purchased from Jackson laboratories and fed a high fat diet (60% kCal % fat, Research Diets) for the duration of the study. Female DBA/1J mice were purchased from Taconic. CIA was induced in 8 weeks as previously described[40].

Hydrogen-deuterium exchange (HDX) detected by mass spectrometry (MS): Solution-phase amide HDX experiments were carried out with a fully automated system (CTC HTS PAL, LEAP Technologies, Carrboro, NC; housed inside a 4° C. cabinet) as described previously with the modifications described below[41].

Peptide Identification: Peptides were identified using tandem MS (MS/MS) experiments performed with a QExactive (ThermoFisher, San Jose, CA) over a 70 min gradient. Product ion spectra were acquired in a data-dependent mode and the five most abundant ions were selected for the product ion analysis per scan event. The MS/MS *.raw data files were converted to *.mgf files and then submitted to MASCOT (version 2.3 Matrix Science, London, UK) for peptide identification. The maximum number of missed cleavages was set at 4 with the mass tolerance for precursor ions +/−0.6 Da and for fragment ions +/−8 ppm. Oxidation to methionine was selected for variable modification. Pepsin was used for digestion and no specific enzyme was selected in the MASCOT during the search. Peptides included in the peptide set used for HDX detection had a MASCOT score of 20 or greater. The MS/MS MASCOT search was also performed against a decoy (reverse) sequence and false positives were ruled out if they did not pass a 1% false discovery rate. The MS/MS spectra of all the peptide ions from the MASCOT search were further manually inspected and only the unique charged ions with the highest MASCOT score were included in HDX peptide set.

Hydrogen/deuterium exchange (HDX) analysis: 10 μM of the apo protein (LXRα LBD and PPARγ LBD) was mixed with 1:10 molar excess of ligand and incubated for 2 hours at 4° C. for complex formation before subjecting them to HDX analysis. For the differential HDX experiments, 5 μl of either the apo or the liganded protein complex were mixed with 20 μl of $D_2O$-containing HDX buffer (50 mM HEPES pH 7.5, 1 M NaCl, 3 mM DTT) and incubated at 4° C. for 0 s, 10 s, 30 s, 60 s, 900 s or 3,600 s. Following on-exchange, unwanted forward- or back-exchange was minimized, and the protein was denatured by the addition of 25 μl of a quench solution (1% v/v TFA in 5 M urea and 50 mM TCEP). Samples were then immediately passed through an immobilized pepsin column (prepared in house) at 50 μl min-1 (0.1% v/v TFA, 15° C.) and the resulting peptides were trapped and desalted on a 1.0 mm×10 mm C8 trap column (Hypersil Gold, Thermo Fisher, Grand Island, NY). The bound peptides were then gradient-eluted (5-50% CH3CN v/v and 0.3% v/v formic acid) across a 1.0 mm×50 mm C18 separation column (Hypersil Gold, Thermo Fisher, Grand Island, NY) for 6 min. Sample handling and peptide separation were conducted at 4° C. The eluted peptides were then subjected to electrospray ionization directly coupled to a high resolution Orbitrap mass spectrometer (QExactive or Exactive, ThermoFisher, San Jose, CA). Each HDX experiment was carried out in triplicate with a single preparation of each protein-ligand complex. The intensity weighted mean m/z centroid value of each peptide envelope was calculated and subsequently converted into a percentage of deuterium incorporation. This is accomplished by determining the observed averages of the undeuterated and fully deuterated spectra using the conventional formula described elsewhere[42]. In the absence of a fully deuterated control, 100% deuterium incorporation was calculated theoretically, and corrections for back-exchange were made on the basis of an estimated 70% deuterium recovery and accounting for 80% final deuterium concentration in the sample (1:5 dilution in $D_2O$ HDX buffer). Statistical significance for the differential HDX data is determined by an unpaired t-test for each time point, a procedure that is integrated into the HDX Workbench software[43].

Docking model: The model for SR1903 was generated using PRODRG[44]. The ICM Pro suite (Molsoft) was used to dock SR1903 into the PPARγ LBD structure. PDB 6C5Q with ligands and waters removed was used as the starting model for docking[15]. The receptor was prepared for docking by protonation and energy minimization by means of the ICM force field and distance dependent dielectric potential. PocketFinder within ICM was used to define the ligand binding pocket and was consistent with previously published X-ray structures. Default settings within the ICM docking module were used with a rectangular box centered at the LBP. The top ranked docked result was chosen due to its similarity to previously solved crystal structures of SR10171 and SR11023. Docking studies involving RORγ and LXRβ were performed by using Autodock Vina implemented in UCSF Chimera[45]. The cocrystal structure of LXRβ bound to T0901317 (1PQC[19]) and a cocrystal model of RORγ bound to SR2211 were used for SR1903 docking studies. The dock protocol was performed using default settings within a box that was drawn around the ligand binding pocket. The receptor and SR1903 models were prepared for docking by adding hydrogen atoms to the ligand and receptor models and by removing water, solvent, and ligands.

Flow cytometry and antibodies: For the analysis of macrophage activation, RAW264.7 cells (American Type Culture Collection) were pre-incubated with 5 µM 1903 for 18 h then stimulated with 1 µg/mL LPS (*Escherichia coli* 0127:B8, Sigma-Aldrich (St. Louis, MO)) for 6 h. RAW264.7 cells were stained with APC conjugated anti-TREM-1 antibody (eBioscience). Cell sorting was performed using LSRII (BD Bioscience).

Leptin sensitivity assay: Mice from 18 to 24 weeks of age were individually caged. Murine leptin (Sigma) (1.5 ug/g body weight) were injected intraperitoneally twice daily (7:00 am and 7:00 pm) for 3 days. Body weight and food intake were measured daily.

Glucose tolerance test (GTT): Male mice were used because they are more hormonally stable. For a glucose tolerance test, 24 weeks old mice fed on a HFD were fasted overnight and glucose was administered intraperitoneally (1.5 mg/kg body weight). Glucose levels were measured in blood withdrawn from the tail.

ELISA (Insulin and leptin) and metabolic measurements: The serum insulin and leptin concentration were determined with enzyme-linked immunosorbent assay (ELISA) kits (Millipore Sigma).

Statistical analysis: All data are expressed as the mean±s.e.m. (n=3 or more). Statistical analysis was performed using an unpaired Student's t-test.

REFERENCES

1. Marciano, D. P.; Chang, M. R.; Corzo, C. A.; Goswami, D.; Lam, V. Q.; Pascal, B. D.; Griffin, P. R. (2014) The therapeutic potential of nuclear receptor modulators for treatment of metabolic disorders: PPARgamma, RORs, and Rev-erbs. *Cell metabolism* 19, 193-208.
2. Pearce, D.; Matsui, W.; Miner, J. N.; Yamamoto, K. R. (1998) Glucocorticoid receptor transcriptional activity determined by spacing of receptor and nonreceptor DNA sites. *J Biol Chem* 273, 30081-30085.
3. Miller, S. A.; Weinmann, A. S. (2009) Common themes emerge in the transcriptional control of T helper and developmental cell fate decisions regulated by the T-box, GATA and ROR families. *Immunology* 126, 306-315.
4. Chang, M. R.; Lyda, B.; Kamenecka, T. M.; Griffin, P. R. (2014) Pharmacologic repression of retinoic acid receptor-related orphan nuclear receptor gamma is therapeutic in the collagen-induced arthritis experimental model. *Arthritis Rheumatol* 66, 579-588.
5. Sheridan, C. (2013) Footrace to clinic heats up for T-cell nuclear receptor inhibitors. *Nature biotechnology* 31, 370.
6. Solt, L. A.; Kumar, N.; Nuhant, P.; Wang, Y. J.; Lauer, J. L.; Liu, J.; Istrate, M. A.; Kamenecka, T. M.; Roush, W. R.; Vidovic, D.; Schurer, S. C.; Xu, J. H.; Wagoner, G.; Drew, P. D.; Griffin, P. R.; Burris, T. P. (2011) Suppression of T(H)17 differentiation and autoimmunity by a synthetic ROR ligand. *Nature* 472, 491-494.
7. Saurer, L.; Zysset, D.; Rihs, S.; Mager, L.; Gusberti, M.; Simillion, C.; Lugli, A.; Zlobec, I.; Krebs, P.; Mueller, C. (2017) TREM-1 promotes intestinal tumorigenesis. *Sci Rep* 7, 14870.
8. Dower, K.; Ellis, D. K.; Saraf, K.; Jelinsky, S. A.; Lin, L. L. (2008) Innate immune responses to TREM-1 activation: overlap, divergence, and positive and negative crosstalk with bacterial lipopolysaccharide. *J Immunol* 180, 3520-3534.
9. Zysset, D.; Weber, B.; Rihs, S.; Brasseit, J.; Freigang, S.; Riether, C.; Banz, Y.; Cerwenka, A.; Simillion, C.; Marques-Vidal, P.; Ochsenbein, A. F.; Saurer, L.; Mueller, C. (2016) TREM-1 links dyslipidemia to inflammation and lipid deposition in atherosclerosis. *Nat Commun* 7, 13151.
10. Pascual-Garcia, M.; Rue, L.; Leon, T.; Julve, J.; Carbo, J. M.; Matalonga, J.; Auer, H.; Celada, A.; Escola-Gil, J. C.; Steffensen, K. R.; Perez-Navarro, E.; Valledor, A. F. (2013) Reciprocal negative cross-talk between liver X receptors (LXRs) and STAT1: effects on IFN-gamma-induced inflammatory responses and LXR-dependent gene expression. *J Immunol* 190, 6520-6532.
11. Vucic, E.; Calcagno, C.; Dickson, S. D.; Rudd, J. H.; Hayashi, K.; Bucerius, J.; Moshier, E.; Mounessa, J. S.; Roytman, M.; Moon, M. J.; Lin, J.; Ramachandran, S.; Tanimoto, T.; Brown, K.; Kotsuma, M.; Tsimikas, S.; Fisher, E. A.; Nicolay, K.; Fuster, V.; Fayad, Z. A. (2012) Regression of inflammation in atherosclerosis by the LXR agonist R211945: a noninvasive assessment and comparison with atorvastatin. JACC Cardiovasc Imaging 5, 819-828.
12. Penas, F.; Mirkin, G. A.; Vera, M.; Cevey, A.; Gonzalez, C. D.; Gomez, M. I.; Sales, M. E.; Goren, N. B. (2015) Treatment in vitro with PPARalpha and PPARgamma ligands drives M1-to-M2 polarization of macrophages from T. cruzi-infected mice. Biochim Biophys Acta 1852, 893-904.
13. Choi, J. H.; Banks, A. S.; Kamenecka, T. M.; Busby, S. A.; Chalmers, M. J.; Kumar, N.; Kuruvilla, D. S.; Shin, Y.; He, Y.; Bruning, J. B.; Marciano, D. P.; Cameron, M. D.; Laznik, D.; Jurczak, M. J.; Schurer, S. C.; Vidovic, D.; Shulman, G. I.; Spiegelman, B. M.; Griffin, P. R. (2011) Antidiabetic actions of a non-agonist PPARgamma ligand blocking Cdk5-mediated phosphorylation. Nature 477, 477-481.
14. Stechschulte, L. A.; Czernik, P. J.; Rotter, Z. C.; Tausif, F. N.; Corzo, C. A.; Marciano, D. P.; Asteian, A.; Zheng, J.; Bruning, J. B.; Kamenecka, T. M.; Rosen, C. J.; Griffin, P. R.; Lecka-Czernik, B. (2016) PPARG Post-translational Modifications Regulate Bone Formation and Bone Resorption. EBioMedicine 10, 174-184.
15. Frkic, R. L.; Marshall, A. C.; Blayo, A. L.; Pukala, T. L.; Kamenecka, T. M.; Griffin, P. R.; Bruning, J. B. (2018) PPARgamma in Complex with an Antagonist and Inverse Agonist: a Tumble and Trap Mechanism of the Activation Helix. iScience 5, 69-79.
16. Zheng, J.; Corzo, C.; Chang, M. R.; Shang, J.; Lam, V. Q.; Brust, R.; Blayo, A. L.; Bruning, J. B.; Kamenecka, T. M.; Kojetin, D. J.; Griffin, P. R. (2018) Chemical Cross-linking Mass Spectrometry Reveals the Conformational Landscape of the Activation Helix of PPARgamma; a Model for Ligand-Dependent Antagonism. Structure.
17. Rene, O.; Fauber, B. P.; Boenig Gde, L.; Burton, B.; Eidenschenk, C.; Everett, C.; Gobbi, A.; Hymowitz, S. G.; Johnson, A. R.; Kiefer, J. R.; Liimatta, M.; Lockey, P.; Norman, M.; Ouyang, W.; Wallweber, H. A.; Wong, H. (2015) Minor Structural Change to Tertiary Sulfonamide RORc Ligands Led to Opposite Mechanisms of Action. ACS Med Chem Lett 6, 276-281.
18. Fujita-Sato, S.; Ito, S.; Isobe, T.; Ohyama, T.; Wakabayashi, K.; Morishita, K.; Ando, O.; Isono, F. (2011) Structural basis of digoxin that antagonizes RORgamma t receptor activity and suppresses Th17 cell differentiation and interleukin (IL)-17 production. J Biol Chem 286, 31409-31417.
19. Farnegardh, M.; Bonn, T.; Sun, S.; Ljunggren, J.; Ahola, H.; Wilhelmsson, A.; Gustafsson, J. A.; Carlquist, M. (2003) The three-dimensional structure of the liver X receptor beta reveals a flexible ligand-binding pocket that can accommodate fundamentally different ligands. J Biol Chem 278, 38821-38828.
20. Williams, S.; Bledsoe, R. K.; Collins, J. L.; Boggs, S.; Lambert, M. H.; Miller, A. B.; Moore, J.; McKee, D. D.; Moore, L.; Nichols, J.; Parks, D.; Watson, M.; Wisely, B.; Willson, T. M. (2003) X-ray crystal structure of the liver X receptor beta ligand binding domain: regulation by a histidine-tryptophan switch. J Biol Chem 278, 27138-27143.
21. Fujiwara, N.; Kobayashi, K. (2005) Macrophages in inflammation. Curr Drug Targets Inflamm Allergy 4, 281-286.
22. Barish, G. D.; Downes, M.; Alaynick, W. A.; Yu, R. T.; Ocampo, C. B.; Bookout, A. L.; Mangelsdorf, D. J.; Evans, R. M. (2005) A Nuclear Receptor Atlas: macrophage activation. Mol Endocrinol 19, 2466-2477.
23. Pourcet, B.; Gage, M. C.; Leon, T. E.; Waddington, K. E.; Pello, O. M.; Steffensen, K. R.; Castrillo, A.; Valledor, A. F.; Pineda-Torra, I. (2016) The nuclear receptor LXR modulates interleukin-18 levels in macrophages through multiple mechanisms. Sci Rep 6, 25481.
24. Bouchon, A.; Facchetti, F.; Weigand, M. A.; Colonna, M. (2001) TREM-1 amplifies inflammation and is a crucial mediator of septic shock. Nature 410, 1103-1107.
25. Yvan-Charvet, L.; Welch, C.; Pagler, T. A.; Ranalletta, M.; Lamkanfi, M.; Han, S.; Ishibashi, M.; Li, R.; Wang, N.; Tall, A. R. (2008) Increased inflammatory gene expression in ABC transporter-deficient macrophages: free cholesterol accumulation, increased signaling via toll-like receptors, and neutrophil infiltration of atherosclerotic lesions. Circulation 118, 1837-1847.
26. Tall, A. R.; Yvan-Charvet, L. (2015) Cholesterol, inflammation and innate immunity. Nat Rev Immunol 15, 104-116.
27. Ghisletti, S.; Huang, W.; Ogawa, S.; Pascual, G.; Lin, M. E.; Willson, T. M.; Rosenfeld, M. G.; Glass, C. K. (2007) Parallel SUMOylation-dependent pathways mediate gene- and signal-specific transrepression by LXRs and PPARgamma. Mol Cell 25, 57-70.
28. Lao, Y.; Yang, K.; Wang, Z.; Sun, X.; Zou, Q.; Yu, X.; Cheng, J.; Tong, X.; Yeh, E. T.; Yang, J.; Yi, J. (2018) DeSUMOylation of MKK7 kinase by the SUMO2/3 protease SENP3 potentiates lipopolysaccharide-induced inflammatory signaling in macrophages. J Biol Chem.
29. Liu, X.; Chen, W.; Wang, Q.; Li, L.; Wang, C. (2013) Negative regulation of TLR inflammatory signaling by the SUMO-deconjugating enzyme SENP6. PLoS Pathog 9, e1003480.
30. Andre, E.; Gawlas, K.; Steinmayr, M.; Becker-Andre, M. (1998) A novel isoform of the orphan nuclear receptor ROR beta is specifically expressed in pineal gland and retina. Gene 216, 277-283.
31. Kumar, N.; Solt, L. A.; Conkright, J. J.; Wang, Y.; Istrate, M. A.; Busby, S. A.; Garcia-Ordonez, R. D.; Burris, T. P.; Griffin, P. R. (2010) The benzenesulfoamide T0901317 [N-(2,2,2-trifluoroethyl)-N-[4-[2,2,2-trifluoro-1-hydroxy-1-(trifluoromethyl)ethyl]phenyl]-benzenesulfonamide] is a novel retinoic acid receptor-related orphan receptor-alpha/gamma inverse agonist. Mol Pharmacol 77, 228-236.
32. Chang, M. R.; He, Y.; Khan, T. M.; Kuruvilla, D. S.; Garcia-Ordonez, R.; Corzo, C. A.; Unger, T. J.; White, D. W.; Khan, S.; Lin, L.; Cameron, M. D.; Kamenecka, T. M.; Griffin, P. R. (2015) Antiobesity Effect of a Small Molecule Repressor of RORgamma. Mol Pharmacol 88, 48-56.
33. Meissburger, B.; Ukropec, J.; Roeder, E.; Beaton, N.; Geiger, M.; Teupser, D.; Civan, B.; Langhans, W.; Nawroth, P. P.; Gasperikova, D.; Rudofsky, G.; Wolfrum, C. (2011) Adipogenesis and insulin sensitivity in obesity are regulated by retinoid-related orphan receptor gamma. EMBO Mol Med 3, 637-651.
34. Halatchev, I. G.; Cone, R. D. (2005) Peripheral administration of PYY(3-36) produces conditioned taste aversion in mice. Cell metabolism 1, 159-168.
35. Howard, J. K.; Cave, B. J.; Oksanen, L. J.; Tzameli, I.; Bjorbaek, C.; Flier, J. S. (2004) Enhanced leptin sensitivity and attenuation of diet-induced obesity in mice with haploinsufficiency of Socs3. Nat Med 10, 734-738.
36. Sempowski, G. D.; Gooding, M. E.; Liao, H. X.; Le, P. T.; Haynes, B. F. (2002) T cell receptor excision circle assessment of thymopoiesis in aging mice. Mol Immunol 38, 841-848.

37. Yang, H.; Youm, Y. H.; Vandanmagsar, B.; Rood, J.; Kumar, K. G.; Butler, A. A.; Dixit, V. D. (2009) Obesity accelerates thymic aging. *Blood* 114, 3803-3812.
38. Smith, S. H.; Peredo, C. E.; Takeda, Y.; Bui, T.; Neil, J.; Rickard, D.; Millerman, E.; Therrien, J. P.; Nicodeme, E.; Brusq, J. M.; Birault, V.; Viviani, F.; Hofland, H.; Jetten, A. M.; Cote-Sierra, J. (2016) Development of a Topical Treatment for Psoriasis Targeting RORgamma: From Bench to Skin. *PLoS One* 11, e0147979.
39. Fessler, M. B. (2018) The challenges and promise of targeting the Liver X Receptors for treatment of inflammatory disease. *Pharmacol Ther* 181, 1-12.
40. Chang, M. R.; Lyda, B.; Kamenecka, T. M.; Griffin, P. R. (2013) Pharmacological repression of RORgamma is therapeutic in the collagen-induced arthritis experimental model. *Arthritis and rheumatism*.
41. Chalmers, M. J.; Busby, S. A.; Pascal, B. D.; He, Y.; Hendrickson, C. L.; Marshall, A. G.; Griffin, P. R. (2006) Probing protein ligand interactions by automated hydrogen/deuterium exchange mass spectrometry. *Anal Chem* 78, 1005-1014.
42. Zhang, Z.; Smith, D. L. (1993) Determination of amide hydrogen exchange by mass spectrometry: a new tool for protein structure elucidation. *Protein science: a publication of the Protein Society* 2, 522-531.
43. Pascal, B. D.; Willis, S.; Lauer, J. L.; Landgraf, R. R.; West, G. M.; Marciano, D.; Novick, S.; Goswami, D.; Chalmers, M. J.; Griffin, P. R. (2012) HDX workbench: software for the analysis of H/D exchange MS data. *J Am Soc Mass Spectrom* 23, 1512-1521.
44. Schuttelkopf, A. W.; van Aalten, D. M. (2004) PRODRG: a tool for high-throughput crystallography of protein-ligand complexes. *Acta Crystallogr D Biol Crystallogr* 60, 1355-1363.
45. Trott, O.; Olson, A. J. (2010) AutoDock Vina: improving the speed and accuracy of docking with a new scoring function, efficient optimization, and multithreading. *J Comput Chem* 31, 455-461.
46. Hamilton, B. A.; Frankel, W. N.; Kerrebrock, A. W.; Hawkins, T. L.; FitzHugh, W.; Kusumi, K.; Russell, L. B.; Mueller, K. L.; vanBerkel, V.; Birren, B. W.; Kruglyak, L.; Lander, E. S. (1996) Disruption of the nuclear hormone receptor ROR alpha in staggerer mice. *Nature* 379, 736-739.
47. Andre, E.; Conquet, F.; Steinmayr, M.; Stratton, S. C.; Porciatti, V.; Becker-Andre, M. (1998) Disruption of retinoid-related orphan receptor beta changes circadian behavior, causes retinal degeneration and leads to vacillans phenotype in mice. *Embo Journal* 17, 3867-3877.
48. Medvedev, A.; Yan, Z. H.; Hirose, T.; Giguere, V.; Jetten, A. M. (1996) Cloning of a cDNA encoding the murine orphan receptor RZR/ROR gamma and characterization of its response element. *Gene* 181, 199-206.
49. Kumar, N.; Lyda, B.; Chang, M. R.; Lauer, J. L.; Solt, L. A.; Burris, T. P.; Kamenecka, T. M.; Griffin, P. R. (2012) Identification of SR2211: a potent synthetic RORgamma-selective modulator. *ACS Chem Biol* 7, 672-677.

While this invention has been particularly shown and described with references to preferred embodiments thereof, it will be understood by those skilled in the art that various changes in form and details may be made therein without departing from the scope of the invention encompassed by the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference. The relevant teachings of all patents, published applications and references cited herein are incorporated by reference in their entirety.

What is claimed is:

1. A method of treating an inflammatory disease or autoimmune disease and protecting against loss of thymocytes in a subject in need thereof,
    wherein the inflammatory disease or autoimmune disease is selected from the group consisting of inflammatory bowel disease, rheumatoid arthritis, ankylosing spondylitis, juvenile idiopathic arthritis, gout, lupus-associated arthritis, psoriasis, psoriatic arthritis, multiple sclerosis, and chronic inflammatory demyelinating polyneuropathy,
    the method comprising administering to said subject an effective amount of the compound SR1903:

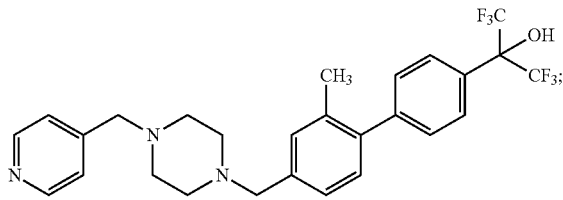 [SMILES: Cc1cc(CN2CCN(Cc3ccncc3)CC2)ccc1-c1ccc(C(O)(C(F)(F)F)C(F)(F)F)cc1]

or a pharmaceutically acceptable salt thereof.

2. The method of claim 1, wherein the inflammatory disease or autoimmune disease is selected from the group consisting of rheumatoid arthritis, ankylosing spondylitis, juvenile idiopathic arthritis, gout, and lupus-associated arthritis.

3. The method of claim 1, wherein the inflammatory disease or autoimmune disease is IBD.

4. The method of claim 3, wherein the IBD is IBD refractory to anti-TNF therapy.

5. The method according to claim 1, wherein the protection against loss of thymocytes is determined by measuring the T-cell count of the subject before the administration of the SR1903 and measuring the T-cell count after the administration of the SR1903, whereby the T-cell counts of the subject are within about 10% of each other.

6. The method of claim 1, wherein the inflammatory disease or autoimmune disease is psoriasis or psoriatic arthritis.

7. The method of claim 1, wherein the inflammatory disease or autoimmune disease is multiple sclerosis or chronic inflammatory demyelinating polyneuropathy.

8. The method of claim 1, wherein the inflammatory disease or autoimmune disease is selected from the group consisting of ankylosing spondylitis, juvenile idiopathic arthritis, gout, and lupus-associated arthritis.

* * * * *